United States Patent [19]

Kerwin, Jr. et al.

[11] Patent Number: 5,346,907

[45] Date of Patent: Sep. 13, 1994

[54] AMINO ACID ANALOG CCK ANTAGONISTS

[75] Inventors: James F. Kerwin, Jr., Mundelein; Mark W. Holladay, Libertyville; Michael J. Bennett, Morton Grove, all of Ill.

[73] Assignee: Abbott Laboratories, Abbott Park, Ill.

[21] Appl. No.: 17,565

[22] Filed: Feb. 16, 1993

Related U.S. Application Data

[63] Continuation-in-part of Ser. No. 793,414, Jun. 26, 1990, abandoned, which is a continuation-in-part of Ser. No. 582,896, Apr. 4, 1989, abandoned, which is a continuation-in-part of Ser. No. 376,778, Jul. 7, 1989, abandoned, which is a continuation-in-part of Ser. No. 177,715, Apr. 5, 1988, abandoned.

[51] Int. Cl.$^5$ .................. A61K 31/47; C07D 215/22; C07D 209/18
[52] U.S. Cl. .................. 514/312; 546/169; 546/201; 546/229; 546/156; 540/467; 540/470; 544/333; 544/373; 544/386; 548/338.1; 548/338.5; 514/19
[58] Field of Search .................. 514/19, 311, 312, 313, 514/210, 233.5, 233.8, 292, 318, 316, 340, 374, 397, 413, 465; 548/311.4, 215, 492, 233, 19 D, 200, 300.4; 544/53, 60, 61, 159, 128, 139, 143, 162, 333, 363, 373, 386; 546/153, 87, 156, 159, 169, 201, 221, 275, 276, 229; 540/467, 470, 544, 553; 549/467

[56] References Cited

U.S. PATENT DOCUMENTS 4,880,938 11/1989 Freidinger .................. 548/492
4,971,978 11/1990 Nadzam et al. .................. 514/312

OTHER PUBLICATIONS

Bohnert, et al. Z. Naturforsch 426, 1159–1166 1987.
Schroff, J. Med. Chem. 1982 25 359–362.
Jensen, et al. Biochemica et Biophys Acta 757 (1983) 250–258.
Bock, et al. J. Med. Chem. 1989, 32, 13–16.
Faris, et al. Science, vol. 226, 1984 pp. 1215–1217.
Hahne, Proc. Natl. Acad. Sci. USA 78(10) pp. 6304–6308, 1981.

*Primary Examiner*—Mukund J. Shah
*Assistant Examiner*—Pavanaram K. Sripada
*Attorney, Agent, or Firm*—Richard A. Elder; Steven R. Crowley; Steven F. Weinstock

[57] ABSTRACT

Analogs of CCK-tetrapeptides, which analogs have the formula

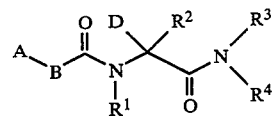

wherein A, B, D, $R^1$, $R^2$, $R^3$, and $R^4$ are specifically defined, having activity as CCK antagonists, useful in the treatment or prevention of disorders of the gastrointestinal, central nervous, appetite regulating or pain regulating systems.

6 Claims, No Drawings

AMINO ACID ANALOG CCK ANTAGONISTS

This is a continuation-in-part of U.S. patent application Ser. No. 793,414, filed Jun. 26, 1990 now abandoned, originally filed through the PCT as patent application Ser. No. PCT/US90/03630, which is a continuation-in-part of U.S. patent application Ser. No. 582,896 filed Apr. 4, 1989, now abandoned, which is a continuation-in-part of U.S. patent application Ser. No. 376,778, filed Jul. 7, 1989, now abandoned originally filed through the PCT as patent application Ser. No. PCT/US89/01412, filed Apr. 4, 1989, which is a continuation-in-part of U.S. patent application Ser. No. 177,715, filed Apr. 5, 1988, now abandoned.

TECHNICAL FIELD

The present invention relates to compounds and compositions which antagonize cholecystokinin and gastrin, processes for making such compounds, synthetic intermediates employed in these processes and a method for treating gastrointestinal disorders, central nervous system disorders, cancers of the gastrointestinal system (i.e., pancreas, gall bladder, etc.), hypoinsulinemia, or potentiating analgesics, or regulating appetite disorders with such compounds.

BACKGROUND OF THE INVENTION

Cholecystokinins (CCK) are a family of polypeptide hormones. CCK and a 33 amino acid fragment of CCK ($CCK_{33}$) were first isolated from hog intestine. (Mutt and Jorpes, Biochem. J., 125,628, 1981). Recently the $CCK_{33}$ fragment has been found in the brain, where it appears to be the precursor of two smaller fragments, an octapeptide $CCK_8$ and a tetrapeptide $CCK_4$ (Dockray, Nature, 264, 4022, 1979).

$CCK_8$, the carboxyl terminal octapeptide fragment of CCK, is the smallest CCK fragment that remains fully biologically-active. (Larsson and Rehfeld, Brain Res. 165,201–218, 1979). The localization of CCK fragments in the cortex of the brain suggests that CCK may be an important neuromodulator of memory, learning and control of primary sensory and motor functions. CCK and its fragments are believed to play an important role in appetite regulation and satiety. (Della-Fera, Science. 206,471, 1979; Gibbs et al., Nature, 289, 599, 1981; and Smith, Eating and Its Disorders, Raven Press, New York, p. 67, 1984).

CCK antagonists (B. J. Gertz in Neurology and Neurobiology, Vol 47, Cholecystokinin Antagonists, Wang and Schoenfeld, eds., Alan R. Liss, Inc., New York, N.Y., pp. 327–342, 1988; Silverman et al., Am J Gastroent, 82(8), 703–8, 1987) are useful in the treatment and prevention of CCK-related disorders of the gastrointestinal (GI) (Lotti et al., J. Pharm Exp Therap, 241(1), 103–9, 1987), central nervous (CNS) (Panerai et al., Neuropharmacology, 26(9), 1285–87, 1987) and appetite regulatory systems of animals, especially man. CCK antagonists are also useful in potentiating and prolonging opiate induced analgesia and thus have utility in the treatment of pain. (Faris et al., Science 226, 1215, 1984; Rovati et al., Clinical Research, 34(2), 406A, 1986; Dourish et al., European J. Pharmacology, 147, 469–72, 1988). Disease states that may be treated with CCK antagonists are disorders of gastric emptying, gastroesophageal reflux disease (Setnikar et al, Arzn Forsch./Drug Research, 37(II) 10, 1168–71, 1987), pancreatitis, pancreatic and gastric carcinomas (Douglas et al., Gastroent, 96, 4629, 1989; Beauchamp et al., Am Surg. 202, 313–9, 1985), disorders of bowel motility, biliary dyskinesia, anorexia nervosa, hypoglycemia (Rossetti, Diabetes, 36, 1212–15, 1987; Reagan, European J. Pharmacology, 144, 241–3, 1987), gallbladder disease, and the like.

Previously four distinct chemical classes of CCK receptor antagonists have been reported. The first class comprises derivatives of cyclic nucleotides as represented by dibutyryl cyclic GMP (Barlos et al., Am, J. Physiol., 242, G161, 1982) and references sited therein). The second class is represented by the C-terminal fragments of CCK (see Jensen et al., Biochem. Biophys. Acta, 757, 250 1983) and Spanarkel, J. Biol. Chem. 258, 6746, 1983). The third class comprises amino acid derivatives of glutamic acid and tryptophan as indicated by proglumide (and its analogs) and benzotript, very simple analogs of CCK (see Hahne et al., Proc. Natl. Acad, Sci. U.S.A., 78, 6304, 1981 and Jensen et al., Biochem. Biophys. Acta. 761,269, 1983). The fourth and most recent class is comprised of 3-substituted benzodiazepines, represented by L-364,718 (see: Evans et al., Proc. Natl, Acad, Sci, U.S.A., 83 4918, 1986).

With the exception of certain substituted benzodiazepines and recently reported analogs of proglumide (Makovec et al., Arzneim.-Forsch./Drug Res. 36,(I), 98–102, 1986; European Patent Application No. 0,272,228; PCT Patent Application No. WO 88/05774) , all of these compounds are relatively weak antagonists of CCK usually demonstrating $IC_{50}$'s between $10^{-4}$ and $10^{-6}$M. The benzodiazepine CCK antagonists or their metabolites may have undesirable effects in vivo due to their interaction with benzodiazepine or other receptors.

The C-terminal pentapeptide fragment of CCK is the same as the C-terminal pentapeptide fragment of another polypeptide hormone, gastrin Gastrin, like CCK, exists in the GI system. Gastrin antagonists are useful in the treatment and prevention of gastrin related disorders of the GI system such as ulcers, Zollinger-Ellison syndrome and central G cell hyperplasia. There are no effective receptor antagonists of the in vivo effects of gastrin. (Morely, Gut Pept. Ulcer Proc., Hiroshima Symp. 2nd, 1, 1983). A recent report (Bock J. Med. Chem., 32, 13–16, 1989) discloses potent in vitro gastrin antagonists.

Analogs of proglumide have also been disclosed by Freidinger (U.S. Pat. 4,860,938) and Nadzan and Kerwin (U.S. Pat. No. 4,971,978), but both require a carboxylate or carboxyalkyl terminal group, respectively, and neither possesses the novel combinations of activity and selectivity of the instant invention.

DISCLOSURE OF THE INVENTION

In accordance with the present invention, there are cholecystokinin antagonists of the formula:

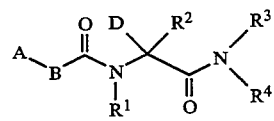

or a pharmaceutically-acceptable salt, ester or amide thereof, wherein:

A is aryl, as defined below; substituted aryl, as defined below; heteroaryl, as defined below; or substituted heteroaryl, as defined below;

B is absent, or is O, N, S, ethylene, or substituted ethylene, as defined below;

$R^1$ is hydrogen or $C_1-C_3$-alkyl, as defined below;

$R^2$ is:
 (1) hydrogen,
 (2) aryl-$C_1-C_3$-alkyl, or
 (3) when $R^3$ is hydrogen, additionally $C_1-C_6$-alkyl, as defined below, $C_3-C_7$-cycloalkyl, as defined below, or $C_2-C_6$-alkenyl, as defined below; or $R^2$ and D are linked together with the atoms to which they are attached to form:
 (a) —$C_4-C_7$-alkylene, as defined below, or
 (b) —$(CH_2)_q$—G—$(CH_2)_q$—, wherein q is independently 1, 2 or 3 at each occurrence and G is O or S;

D is selected from the group consisting of:
 (1) hydrogen,
 (2) $C_1-C_6$-alkyl,
 (3) $C_2-C_6$-alkenyl,
 (4) $C_3-C_7$-cycloalkyl,
 (5) aryl,
 (6) substituted aryl,
 (7) Het, as defined below,
 (8) substituted Het, as defined below,
 (9) aryl-$C_1-C_6$-alkyl-, as defined below,
 (10) Het-$C_1-C_6$-alkyl-, as defined below,
 (11) substituted Het-$C_1-C_6$-alkyl-, as defined below,
 (12) aryl-(mono-substituted-$C_1-C_6$-alkyl)-, as defined below,
 (13) Het-(mono-substituted-$C_1-C_6$-alkyl)-, as defined below,
 (14) $R^6$—O—$C_1-C_6$-alkyl-, wherein: $R^6$ is:
  (i) hydrogen,
  (ii) $C_1-C_6$-alkyl,
  (iii) aryl-$C_1-C_6$-alkyl-,
  (iv) substituted aryl-$C_1-C_6$-alkyl-, as defined below, or
  (v) $R^7$—E—C(O)—, wherein: $R^7$ is:
   (a) $C_1-C_6$-alkyl,
   (b) aryl,
   (c) substituted aryl,
   (d) Het,
   (e) aryl-$C_1-C_6$-alkyl-,
   (f) substituted aryl-$C_1-C_6$-alkyl-, or
   (g) Het-$C_1-C_6$-alkyl-; or
  when E is N—$R^8$, as defined below, $R^7$ and $R^8$ may be linked together with the atoms to which they are attached to form N—$C_4-C_7$-alkylene or N—$(CH_2)_q$—G—$(CH_2)_q$—, wherein q and G are as defined above; and
  E is absent, O, or N—$R^8$, wherein: $R^8$ is:
   (a) hydrogen,
   (b) $C_1-C_6$ alkyl,
   (c) aryl,
   (d) substituted aryl, or
   (e) aryl-$C_1-C_6$-alkyl-; or
  when E is N—$R^8$, additionally $R^7$ and $R^8$ may be linked together with the atoms to which they are attached to form N—$C_4-C_7$-alkylene or N—$(CH_2)_q$—G—$(CH_2)_q$—, wherein q and G are as defined above;
 (15) $R^9$—S—$C_1-C_6$-alkyl-, wherein: $R^9$ is:
  (i) $C_1-C_6$-alkyl,
  (ii) $C_2-C_6$-alkenyl,
  (iii) aryl-$C_1-C_6$-alkyl-,
  (iv) substituted aryl-$C_1-C_6$-alkyl-, or
  (v) $R^7$—E—C(O)—, wherein $R^7$ and E are as defined above;
 (16) $R^{10}$—S(O)$_n$—$C_1-C_6$-alkyl-, wherein:
  n is 1 or 2, and
  $R^{10}$ is $C_1-C_6$-alkyl, aryl-$C_1-C_6$-alkyl-, or substituted aryl-$C_1-C_6$-alkyl-;
 (17) $R^{11}$—NH—$C_1-C_6$-alkyl-, wherein: $R^{11}$ is:
  (i) hydrogen,
  (ii) N-protecting group, as defined below, or
  (iii) $R^7$—J—CO—, wherein $R^7$ is as defined above, and J is:
   (a) absent,
   (b) ethylene,
   (c) substituted ethylene,
   (d) O,
   (e) O—$CH_2$,
   (f) S,
   (f) S—$CH_2$,
   (h) NH, or
   (i) N($C_1-C_3$-alkyl); and
 (18) when $R^2$ is hydrogen and $R^3$ and $R^4$ are linked to form

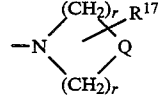

wherein Q, $R^{17}$ and r are as defined below, —$C_1-C_6$-alkyl-CO—N($R^{12}$)($R^{13}$), wherein: $R^{12}$ is hydrogen or $C_1-C_3$-alkyl, and $R^{13}$ is $C_1-C_3$-alkyl, aryl, or aryl-$C_1-C_3$-alkyl, or $R^{12}$ and $R^{13}$ are linked together with the N to which they are attached to form $C_4-C_7$-alkylene or —$(CH_2)_q$—G—$(CH_2)_q$—, wherein q and G are as defined above; or
 (19) D is linked together with $R^2$ and atoms to which they are attached to form $C_4-C_7$-alkylene or —$(CH_2)_q$—G—$(CH_2)_q$—, wherein q and G are as defined above; or
 (20) D is linked together with $R^3$ and atoms to which they are attached to form —CO—N—$C_3-C_6$-alkylene or —CO—N—$(CH_2)_q$—G—$(CH_2)_q$—, wherein q and G are as defined above;

$R^3$ is hydrogen or if $R^2$ or D is hydrogen, then additionally:
 (1) $C_1-C_6$-alkyl,
 (2) $C_1-C_3$-alkyl-O—$C_1-C_3$-alkyl,
 (3) $C_2-C_6$-alkenyl,
 (4) aryl-$C_1-C_6$-alkyl-,
 (5) $C_3-C_7$-cycloalkyl, or
 (6) —$C_1-C_6$-alkylene-$CO_2$-$R^{14}$, wherein $R^{14}$ is $C_1-C_6$-alkyl or $C_3-C_7$-cycloalkyl;

or, $R^3$ and D may be linked together to form —CO—N—$C_3-C_5$-alkylene or —CO—N—$(CH_2)_q$—G—$(CH_2)_q$—, wherein q and G are as defined above;

$R^4$ is selected from the group consisting of:
 (1) $C_1-C_3$-alkyl,
 (2) $C_1-C_3$-alkyl-O—$C_1-C_3$-alkyl,
 (3) $C_2-C_4$-alkenyl,
 (4) aryl,
 (5) aryl-$C_1-C_6$-alkyl-,
 (6) $C_3-C_7$-cycloalkyl,
 (7) cyano-$C_1-C_6$-alkyl, or (8) —$C_1$–$C_3$-alkylene-$CO_2$-$R^{14}$, wherein $R^{14}$ is $C_1$–$C_6$-alkyl, $C_3$–$C_7$-cycloalkyl, aryl, or aryl-$C_1$–$C_6$-alkylene;

or, if $R^2$ is hydrogen, then $R^3$ and $R^4$ may be additionally linked to form:

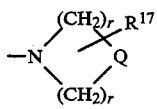

wherein:

r is independently at each occurrence 1 or 2, Q is $CH_2$ or 0, and $R^{17}$ represents one or two substituents independently selected from the group consisting of:
(1) hydrogen,
(2) $C_1$–$C_6$-alkyl,
(3) aryl, and
(4) —C(O)—$R^{18}$, wherein $R^{18}$ is:
(i) aryl,
(ii) substituted aryl,
(iii) heteroaryl,
(iv) aryl-$C_1$–$C_3$-alkyl-,
(v) substituted aryl-$C_1$–$C_3$-alkyl, or
(vi) N—$R^{19}R^{20}$, wherein:
$R^{19}$ is H or $C_1$–$C_3$ alkyl, and
$R^{20}$ is aryl, aryl-$C_1$–$C_6$-alkyl-, or heteroaryl-$C_1$–$C_6$ alkyl-.

Alkyl refers to straight- or branched-chain alkyl radicals containing the indicated number of carbon atoms, for example, $C_1$–$C_6$-alkyl, which contains from 1-to-6 carbon atoms including, but not limited to, methyl, ethyl, n-propyl, iso-propyl, n-butyl, iso-butyl, sec-butyl, n-pentyl, 2-methylbutyl, 2,2-dimethylpropyl, n-hexyl, 2-methylpentyl, 2,2-dimethylbutyl, and the like.

Mono-substituted-$C_1$–$C_6$-alkyl refers to a $C_1$–$C_6$-alkyl chain substituted by one of: methyl, ethyl, oxo, hydroxyl, O-(hydroxyl protecting group), halo, halo-$C_1$–$C_6$-alkyl, cyano, $CO_2H$, and $CO_2$-$C_1$–$C_6$-alkyl, or $CO_2$-$C_1$–$C_6$-alkyl-aryl.

Substituted ethylene refers to an ethylene group substituted with one or two substituents independently selected from $C_1$–$C_6$alkyl, halo, halo-$C_1$–$C_6$-alkyl and cyano.

$C_2$–$C_6$-alkenyl refers to a straight- or branched-chain of 2-lo-6 carbon atoms containing one carbon-carbon double bond including, but not limited to, vinyl, allyl, butenyl and the like.

$C_1$–$C_2$-alkylene refers to a straight- or branched-chain spacer group containing one or two carbon atoms including —$CH_2$—, —CH($CH_3$)—, and —$CH_2$–$CH_2$—.

$C_1$–$C_3$-alkylene refers to a straight- or branched-chain spacer group containing 1-to-3 carbon atoms including, but not limited to, —($CH_2$)—, —($CH_2$)$_2$—, —CH($CH_3$)$CH_2$—, and the like.

$C_4$–$C_6$-alkylene refers to a straight- or branched-chain spacer group containing 4-to-6 carbon atoms including, but not limited to, —($CH_2$)$_4$—, —($CH_2$)$_2$—CH($CH_3$)—, —CH($CH_2CH_3$)$CH_2$—, and the like.

Aryl refers to a monocyclic or bicyclic aromatic carbocyclic ring system of 6–11 carbon atoms including, but not limited to, phenyl, naphthyl, indanyl, (1,2,3,4)-tetrahydronaphthyl, indenyl, isoindenyl and the like.

Substituted aryl refers to an aryl group substituted with one or two substituents, independently selected from $C_1$–$C_6$-alkyl, $C_1$–$C_6$-alkoxy, $C_1$–$C_6$-thioalkoxy, aryl-C(O)—O, aryl-$C_1$–$C_6$-alkyl-C(O)—O—, —C(O)O—$C_1$–$C_6$-alkyl, —$OSO_3H$, cyano, halo, haloalkyl, nitro, hydroxy, —C(O)$NH_2$, —C(O)—NH($C_1$–$C_6$-alkyl), —C(O)N($C_1$–$C_6$-alkyl )$_2$, —C(O)NH($C_3$–$C_6$-alkenyl), —NH($C_1$–$C_6$-alkyl), and —N($C_1$–$C_6$-alkyl)$_2$.

$C_3$–$C_7$-cycloalkyl refers to an alicyclic ring having 3-to-7 carbon atoms including, but not limited to, cyclopropyl, cyclopentyl, cyclohexyl and the like.

$C_3$–$C_7$-cycloalkyl-$C_1$–$C_6$-alkyl- refers to a $C_3$–$C_7$-cycloalkyl group appended to a $C_1$–$C_6$-alkyl radical including, but not limited to, cyclopropylmethyl, cyclohexylethyl, and the like.

Halo refers to F, Cl, Br, or I.

Halo-$C_1$–$C_3$ alkyl refers to a $C_1$–$C_3$ alkyl radical in which one or more hydrogen atoms have been substituted by halo groups, and including but not limited to fluoromethyl, trifluoromethyl, chloroethyl, 2,2-difluoroethyl, 2,3-dibromopropyl, and the like.

Heteroaryl refers to thienyl, pyridyl, pyrazinyl, benzofuranyl, indolyl, oxyindolyl, isoindolyl, indazolyl, indolinyl, 7-azaindolyl, isoindazolyl, benzothiofuranyl, benzopyranyl, quinolyl, isoquinolyl, napthiridinyl, cinnolinyl, quinazolinyl, pyridopyridyl, quinoxadinyl, or tetrahydrocarbolinyl.

Substituted heteroaryl refers to a heteroaryl group substituted with one or two substituents independently selected from methyl, halo, trifluoromethyl, hydroxy, oxo, cyano, phenyl, and protected hydroxyl.

Het refers to thienyl, furanyl, pyrrolyl, imidazolyl, pyrazolyl, thiazolyl, pyrrolidinyl, pyrrolinyl, imidazolidinyl, imidazolinyl, pyrazolidinyl, tetrahydrofuranyl, pyranyl, pyronyl, pyridyl, piperidyl, piperazinyl, benzofuranyl, indazolyl, 7-azaindolyl, isoindazolyl, benzopyranyl, quinolyl, isoquinolyl, or carbolinyl.

Substituted Het refers to a Het heterocycle, as defined above, substituted with one or two substituents independently selected from $C_1$–$C_6$-alkyl, haloalkyl, oxo, hydroxy, protected hydroxyl, alkoxy, thioalkoxy, amino, —C(O)$NH_2$, —C(O)NH($C_1$–$C_6$-alkyl), —C(O)N($C_1$–$C_6$-alkyl)$_2$, —NH($C_1$–$C_6$-alkyl), —N($C_1$–$C_6$-alkyl)$_2$, N-protected amino. protected hydroxyl, —$CO_2H$, aryl-S(O)$_2$-, substituted aryl-S(O)$_2$-, cyano, nitro, and phenyl.

N-protecting group refers to those groups intended to protect the N-terminus of an amino acid or peptide or to protect an amino group against undesirable reactions during synthetic procedures or to prevent the attack of exopeptidases on the compounds or to increase the solubility of the compounds and includes, but is not limited to, sulfonyl, acyl, acetyl, pivaloyl, t-butyloxycarbonyl (Boc), carbobenzyloxy (Cbz), benzoyl or an a-aminoacyl residue, which may itself be N-protected similarly.

Hydroxy-protecting group or O-protecting group refers to a substituent which protects hydroxyl groups against undesirable reactions during synthetic procedures and includes, but is not limited to, substituted methyl ethers, for example methoxymethyl, benzyloxymethyl, 2-methoxyethoxymethyl, 2-(trimethylsilyl)ethoxymethyl, benzyl, and triphenylmethyl; terahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

Exemplary compounds of the present invention include:

N-(3'-Quinolylcarbonyl)-R-valine-di-n-pentylamide;
N-(2'-Indolylcarbonyl)-R-valine-di-n-pentylamide;
N-(4',8'-Dihydroxy-2'-quinolylcarbonyl)-R-valine-di-n-pentylamide;
N-(4'-Hydroxy-2'-quinolylcarbonyl)-R-valine-di-n-pentylamide;
N-(2'-Naphthoyl)-R-valine-di-n-pentylamide;
N-(3'-Quinolylcarbonyl)-R-norleucine-di-n-pentylamide;
N-(2'-Indolylcarbonyl)-R-norleucine-di-n-pentylamide;
N-(4',8'-Dihydroxy-2'-quinolylcarbonyl)-R-norleucine-di-n-pentylamide;
N-(3'-Quinolylcarbonyl)-R-(O-benzyl)serine-di-n-pentylamide;
N-(4'-Hydroxy-2'-quinolylcarbonyl)-R-(O-benzyl)serine-di-n-pentylamide;
N-(3'-Quinolylcarbonyl)-(2R,3S)-(O-benzyl)threonine-di-n-pentylamide;
N-(4'-Hydroxy-2'-quinolylcarbonyl)-(2R,3 S)-(O-benzyl)threonine-di-n-pentylamide;
N-(3'-Quinolylcarbonyl)-(2R,3S)-threonine-di-n-pentylamide;
N-(4'-Hydroxy-2'-quinolylcarbonyl)-(2R,3S)-threonine-di-n-pentylamide;
N-(3'-Quinolylcarbonyl)-(2R,3S)-(O-acetyl)threonine-di-n-pentylamide;
N-(3'-Quinolylcarbonyl)-(2R,3S)-(O-methyl)threonine-di-n-pentylamide;
N-(3'-Quinolylcarbonyl)-3-(2'-thienyl)-R-alanine-di-n-pentylamide;
N-(4'-Hydroxy-2'-quinolylcarbonyl)-3-(2'-thienyl)-R-alanine-di-n-pentylamide;
N-(2'-Indolylcarbonyl)-R-histidine-di-n-pentylamide;
N-(3'-Quinolylcarbonyl)-R-histidine-di-n-pentylamide;
N-(4'-Hydroxy-2'-quinolylcarbonyl)-R-histidine-di-n-pentylamide;
$N^a$-(3'-Quinolylcarbonyl)-N$\epsilon$-(benzyloxycarbonyl)-R-lysine-di-n-pentylamide;
N-(3'-Quinolylcarbonyl)-R-phenylalanine-di-n-pentyl amide;
N-(4'-Hydroxy-2'-quinolylcarbonyl)-R-phenylalanine-di-n-pentylamide;
$N^a$-(3'-Quinolylcarbonyl)-N$^\epsilon$-(2'-chlorobenzyloxycarbonyl)-R-lysine-di-n-pentylamide;
N-(3'-Quinolylcarbonyl)-R-(4'-hydroxyphenyl)glycine-di-n-pentylamide;
$N^a$-(3'-Quinolylcarbonyl)-N$^\epsilon$-(acetyl)-R-lysine-di-n-pentylamide;
N-(2'-Indolylcarbonyl)-R-tyrosine-di-n-pentylamide;
N-(3',4'-Dichlorobenzoyl)-R-tyrosine-di-n-pentylamide;
N-(2'-Naphthoyl)-R-tyrosine-di-n-pentylamide;
N-(3'-Quinolylcarbonyl)-R-tyrosine-di-n-pentylamide;
N-(4'-Hydroxy-2'-quinolylcarbonyl)-R-tyrosine-di-n-pentylamide;
Methyl N-(3'-quinolylcarbonyl)-R-tyrosyl-S-phenylglycinate;
Methyl N-(4'-Hydroxy-2'-quinolylcarbonyl)-R-tyrosyl-S-phenylglycinate;
N-(2'-Indolylcarbonyl)-R-homoserine-di-n-pentylamide;
N-(3'-Quinolylcarbonyl)-R-homoserine-di-n-pentylamide;
N-(4'-Hydroxy-2'-quinolylcarbonyl)-R-homoserine-di-n-pentylamide;
N-(2'-Indolylcarbonyl)-R-methionine-di-n-pentylamide;
N-(2'-Indolylcarbonyl)-R-methioninesulfoxide-di-n-pentylamide;
N-(3'-Quinolylcarbonyl)-R-methionine-di-n-pentylamide;
N-(4'-Hydroxy-2'-quinolylcarbonyl)-R-methionine-di-n-pentylamide;
N-(3'-Quinolylcarbonyl)-R-ioninesulfoxide-di-n-pentylamide;
$N^a$-(3'-Quinolylcarbonyl)-N$^\epsilon$-phenylthiolcarbonyl-R-lysine-di-n-pentylamide;
N-(3'-Quinolylcarbonyl)-R-tyrosine-di-n-pentylamide hydrochloride;
N-(3'-Quinolylcarbonyl)-R-histidine-di-n-pentylamide dihydrochloride;
N-(2'-Indolylcarbonyl)-glycine-di-n-pentylamide;
N-(3'-Quinolylcarbonyl)-glycine-di-n-pentylamide;
N-(3'-Quinolylcarbonyl)-R-phenylglycine-di-n-pentylamide;
N-(4',8'-Dihydroxy-2'-quinolylcarbonyl)-R-Phenylglycine-di-n-pentylamide;
N-(5'-Fluoroindolylcarbonyl)-R-phenylglycine-di-n-pentylamide;
N-(5'-Chloroindolylcarbonyl)-R-phenylglycine-di-n-pentylamide;
N-(4',8'-Dihydroxy-2'-quinolylcarbonyl)-glycine-di-n-pentylamide;
N-(2'-Naphthoyl)-glycine-di-n-pentylamide;
N-(3'- Methylphenylaminocarbonyl)-glycine-di-n-pentylamide;
N-(4',8'-Dihydroxy-2'-quinolylcarbonyl)-R-(4'-hydroxyphenyl)-glycine-di-n-pentylamide;
N-(4',8'-Dihydroxy-2'-quinolylcarbonyl)-(2R,3S)-(O-benzyl)-threonine-di-n-pentylamide;
Methyl N-(2'-Indolylcarbonyl)-R-methionine-S-(p-hydroxy)-phenylglycinate;
Methyl N-(3'-Quinolylcarbonyl)-R-methionine-S-(p-hydroxy)-phenylglycinate;
Methyl N-(4',8'-Dihydroxy-2'-quinolylcarbonyl)-R-methionine-S-(p-hydroxy)-phenylglycinate;
N-(3'-Quinolylcarbonyl)-R-serine-di-n-pentylamide;
N-(4',8'-Dihydroxy-2'-quinolylcarbonyl)-R-serine-di-n-pentylamide;
N-(8'-Hydroxy-2-quinolylcarbonyl)-glycine-di-n-pentylamide;
N-Methyl-N-(3'-quinolylcarbonyl)-glycine-di-n-pentylamide;
N-(3'-Iodo-2'-indolylcarbonyl)-glycine-di-n-pentylamide;
N-(3'-Quinolylcarbonyl)-R-alanine-di-n-pentylamide;
N-(2'-Indolylcarbonyl)-R-alanine-di-n-pentylamide;
N-(4',8'-Dihydroxy-2'-quinolylcarbonyl)-R-alanine-di-n-pentylamide;
N-(m-Toluylaminocarbonyl)-($\beta$-O-benzyl)-R-serine-4'-benzoylpiperidide;
N-(m-Toluylaminocarbonyl)-($\beta$-O-benzyl)-R-aspartyl-4'-benzoylpiperidide;
N-(m-Toluylaminocarbonyl)-($\gamma$-pyrrolidin-1-yl)-R-glutamyl-4'-benzoylpiperidide;
N-(m-Methoxyphenylaminocarbonyl)-($\gamma$-pyrrolidin-1-yl)-R-glutamyl-4'-benzoylpiperidide;
N-(Phenylaminocarbonyl)-($\beta$-O-benzyl)-R-serine-4'-benzoylpiperidide;

N-(m-Methoxyphenylaminocarbonyl)-(β-O-benzyl)-R-serine-4'-benzoylpiperidide;
N-(m-chlorophenylaminocarbonyl)-(β-O-benzyl)-R-serine-4'-benzoylpiperidide;
N-(m-acetylphenylaminocarbonyl)-(β-O-benzyl)-R-serine-4'-benzoylpiperidide;
N-(m-Toluylaminocarbonyl)-(S-benzyl)-S-cysteine-4'-benzoylpiperidide;
N-(m-Toluylaminocarbonyl)-(S-benzyl-S,S-dioxo)-S-cysteine-4'-benzoylpiperidide;
N-(m-Toluylaminocarbonyl)-(S-benzyl-S-oxo)-S-cysteine-4'-benzoylpiperidide;
N-(m-Toluylaminocarbonyl)-(β-O-benzyl)-R-serine-4'-(4-fluorobenzoyl)piperidide;
N-(m-Toluylaminocarbonyl)-(β-O-benzyl)-R-serine-piperidine-4'-carboxanilide;
N-(m-Toluylaminocarbonyl)-(γ-pyrrolidin-1-yl)-R-glutamylpiperidine-4'-carboxanilide;
N-(m-Toluylaminocarbonyl)-(β-O-pyrrolidinecarbamoyl)-R-serine-piperidine-4'-carboxanilide;
N-(m-Toluylaminocarbonyl)-(β-O-benzylcarbamoyl)-R-serine-piperidine-4'-carboxanilide;
N-(m-Toluylaminocarbonyl)-(β-O-(N,N-dimethylaminocarbamoyl))-R-serine-piperidine-4'-carboxanilide;
N-(m-Toluylaminocarbonyl)-(β-O-(N,N-diethylaminocarbamoyl))-R-serine-piperidine-4'-carboxanilide;
N-(m-Toluylaminocarbonyl)-(β-O-pyrrolidinecarbamoyl)-R-serine-4'-benzoylpiperidide;
N-(m-Toluylaminocarbonyl)-(β-O-morpholinecarbamoyl)-R-serine-4'-benzoylpiperidide;
N-(m-Toluylaminocarbonyl)-(β-O-anilinecarbamoyl)-R-serine-4'-benzoylpiperidide;
(m-Toluylaminocarbonyl)-(β-O-benzyl)-R-serine-piperidine-4'-m-bromocarboxanilide; or
N-(3'-Quinolylcarbonyl)-2-allyl-R,S-phenylalanine-n-pentylamide.

Exemplary of the preferred compounds of the invention are:
N-(3'-Quinolylcarbonyl)-(2R,3S)-(O-methyl)threonine-di-n-pentylamide;
N-(3'-Quinolylcarbonyl)-(2R,3S)-threonine-di-n-pentylamide;
N-(3'-Quinolylcarbonyl)-R-histidine-di-n-pentylamide dihydrochloride;
N-(3'-Quinolylcarbonyl)-R-phenylglycine-di-n-pentylamide;
N-(4',8'-Dihydroxy-2'-quinolylcarbonyl)-R-phenylglycine-di-n-pentylamide;
N-(3'-Quinolylcarbonyl)-R-serine-di-n-pentylamide;
Methyl N-(3'-quinolylcarbonyl)-R-tyrosyl-S-phenylglycinate;
N-(3'-Quinolylcarbonyl)-R-(4'-hydroxyphenyl)glycine-di-n-pentylamide;
N-(2'-Indolylcarbonyl)-R-histidine-di-n-pentylamide;
N-(4',8'-Dihydroxy-2'-quinolylcarbonyl)-R-valine-di-n-pentylamide;
N-(2'-Quinolylcarbonyl)-R-valine-di-n-pentylamide;
N-(3'-Quinolylcarbonyl)-R-valine-di-n-pentylamide;
N-(m-Toluylaminocarbonyl)-(γ-pyrrolidin-1-yl)-R-glutamyl-4'-benzoylpiperidide;
N-(m-Methoxyphenylaminocarbonyl)-(γ-pyrrolidin-1-yl)-R-glutamyl-4'-benzoylpiperidide;
N-(m-Toluylaminocarbonyl)-(S-benzyl-S-oxo)-(S)-cysteine-4'-benzoylpiperidide;
N-(m-Toluylaminocarbonyl)-(β-O-pyrrolidinecarbamoyl)-R-serine-piperidine-4'-carboxanilide; or
N-(m-Toluylaminocarbonyl)-(β-O-pyrrolidinecarbamoyl)-R-serine-4'-benzoylpiperidide The compounds of the invention may be made as shown in the following scheme(s). The compounds of the invention having one asymmetric center can exist as separate enantiomers or as mixtures of enantiomers. The compounds of the invention which contain two or more asymmetric carbon atoms can exist as pure diastereomers, mixtures of distereomers, diastereomeric racemates or mixtures of diastereomeric racemates. The present invention includes within its scope all of the isomeric forms.

A number of synthetic pathways exist for the production of α-amino acids and their derivatives. The invention is not limited to those methods discussed here for the synthesis of α-amino acids but is meant to include those variations and methods encompassed by the prior art as discussed in the chemical literature in its entirety. α-Amino acids (refer to Scheme 1) can be produced directly by the displacement of α-halogenated esters (1, X is halo) and the like or other α-situated leaving groups by ammonia and or other substituted amines ($R_1$ is hydrogen, loweralkyl, carboxyester-substituted alkyl) and/or their analogs (e.g., carbamates, hydrazines, azides) (e.g., Marvel, *Org. Synth*, 20, 81, 1940; 106, 1940; 21, 60, 1941; 74, 1941; Birnbaum, *J. Biol, Chem.*, 333, 1953). The antino group is then unmasked, for example by reduction, and the ester group (amide, etc.) is saponified to the acid in a standard fashion.

A second method involves the condensation of an α-ketoester (amide, etc) with an amine or amine equivalent (e.g., hydroxylamine, hydrazine, carbamate, etc.) and the subsequent reduction of this product (2) to the α-aminoester (amide, acid, etc. (e.g., *Can, J. Chem.*, 29, 427, 1951; *J. Org. Chem.*, 38, 822, 1973; *J. Org. Chem.*, 6, 878, 1941)). Alternatively, an organometalic reagent can be added to the oxime 2 (imine, etc.) to provide as final products either monosubstituted α-amino acids in the case where D is hydrogen, or disubstituted amino acids in the case where D is other than hydrogen (e.g., *Tetrahedron Lett.*, 28(42), 4973, 1987).

A third method is the alkylation of a carbanion resulting from compound (3) with an electrophilic nitrogen source (e.g. diethylazodicarboxylate). The intermediate product can subsequently be unmasked to provide the desired α-amino acid. A similar method involves alkylation of the carbanion derived from compound (4) with an appropriate alkylating agent. This method also allows for the possibility of disubstitution of the α center.

A fifth route involves the Strecker reaction and its modifications. Reaction of cyanide and ammonium on aldehydes and ketones (5) provides the amino acid.

A last method involves the direct reduction of unsaturated heterocyclic carboxylic acids (6) to directly provide the cyclic amino acids (7), (wherein D and $R^1$ are encompassed in a ring).

With suitably available α-amino acids (8) (Scheme 2) the amino group is protected with an N protecting group (most frequently Boc or Cbz) and, if the carboxylic acid has not been unmasked, it is saponified with base to provide the parent carboxylic acid (9). The N-protected intermediate is then coupled with the amine $HNR^3R^4$ using any of a number of standard coupling techniques (carbodiimide, BOPCl, chloroformates, oxalylchloride, etc.). Preferred secondary amines are of the type where $R^3$ and $R^4$ are alkyl, arylalkyl, aryl, are connecting such as to form a cyclic secondary amine when taken together with the adjacent nitrogen, or represent another amino acid. The resulting product (10) is then N-deprotected using HCl or trifluoroacetic acid (TFA) to remove a Boc group and hydrogenolysis or HBr to remove a Cbz group. The resultant amine (11) is then coupled with aromatic carboxylic acids, aromatic acid halides, heteroaromatic carboxylic acids, aromatic isocyanates, and the like using standard coupling techniques to provide the desired products (12), (13), and (14). Preferred acyl coupling partners groups include: quinoline carboxylic acids, indole carboxylic acids, substituted benzoic acids and benzoyl chlorides, arylisocyanates and naphthoic acids, benzothiofuranyl carboxylic acids and the like.

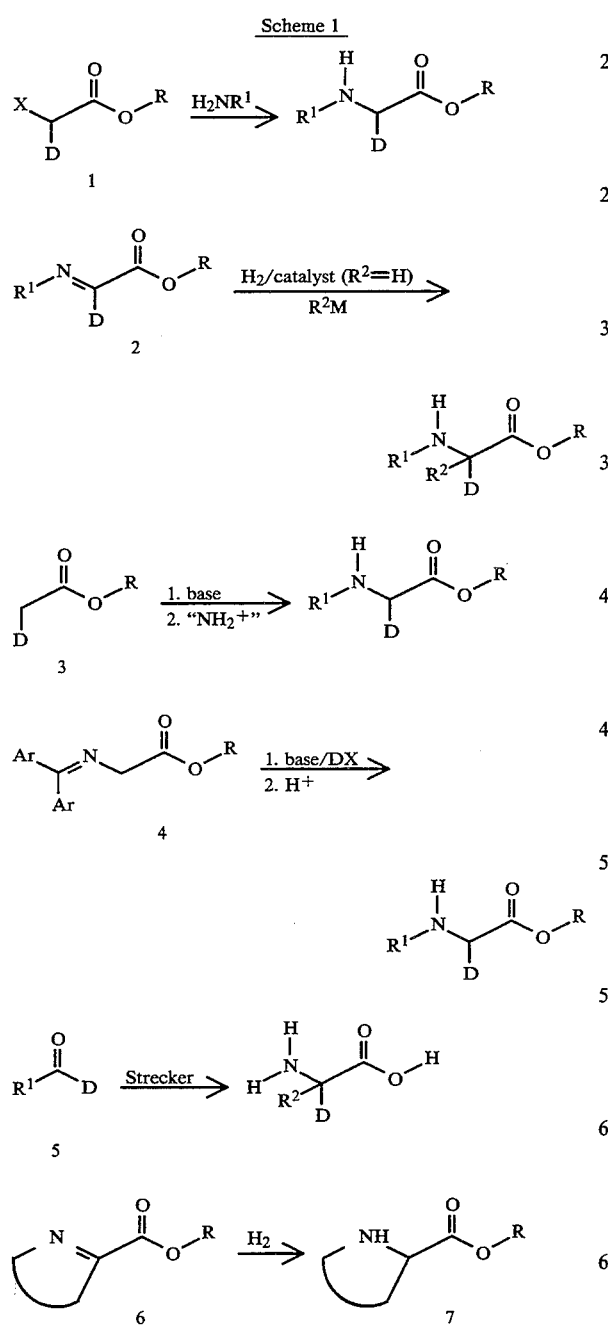

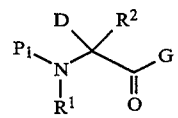

Intermediates for the preparation of the compounds of formula I include compounds of the formula:

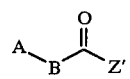

wherein D, $R^1$, $R^2$, $R^3$, and $R^4$ are as defined above, and $P^1$ is hydrogen or an N-protecting group.

Other intermediates for the preparation of compounds of the formula I include compounds of the formula:

$$\underset{B}{\overset{A}{\diagdown}}\overset{O}{\underset{\|}{C}}\underset{Z'}{\diagup}$$

wherein A and B are as defined above, Z' is an activating group; or B—C(O)—Z' taken together represent —N=C=O, or —CH$_2$—N=C=O.

Activating groups are those functional groups which activate a carboxylic acid group toward coupling with an amine to form an amide. Activating groups Z' include, but are not limited to, —OH, —SH, alkoxy, thioalkoxy, halogen, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 4-nitrophenol derived esters, 2,4,5-trichlorophenol derived esters and the like.

The following examples will serve to further illustrate preparation of the novel compounds of this invention.

EXAMPLE 1

N-(3'-Quinolylcarbonyl)-R-valine-di-n-pentylamide

Step 1a.
N-(t-Butyloxycarbonyl)-R-valine-di-n-pentylamide

N-t-Butyloxycarbonyl-R-valine (2.5 g, 11.5 mmol) was stirred at 0° C. in 30 mL of methylene chloride ($CH_2Cl_2$) with bis(2-oxo-3-oxazolidinyl)phosphinic chloride (BOPCl, 3.5 g, 13.8 mmol) and 1.5 mL (11.5 mmol) of triethylamine (TEA). To this reaction mixture was added di-n-pentylamine (11.6 mL, 58 mmol). The mixture was stirred overnight and allowed to warm to room temperature. An additional equivalent of BOPCl was added after 18 hrs and the reaction mixture was stirred an additional day at ambient temperature. The solvents were evaporated in vacuo and the residue taken up in ethylacetate (EtOAc) and washed with water, 1N hydrochloric acid (HCl) solution, saturated sodium bicarbonate solution ($NaHCO_3$), water. The organic solution was dried over magnesium sulfate ($MgSO_4$). After filtration and concentration of the filtrate in vacuo, the residue was chromatographed using EtOAc-hexane as the solvent system in the ratio (1:4). The product was isolated as an oil 79% yield (3.25 g). $[\alpha]_D = +21.2°$ (c=1.5, MeOH). MS(CI) m/e 357(m+H)+. $^1$H NMR($CDCl_3$,300 MHz) δ 0.85–1.0(m,12H), 1.32(m,8H), 1.4–1.5(m,4H), 1.5(s,9H), 1.84(m,1H), 3.05(m,1H), 3.2(m,1H), 3.35(m,1H), 3.55(m,1H), 4.42(m,1H), 5.25(d,J=7 Hz,1H).

Step 1b. R-Valine-di-n-pentylamide hydrochloride

The product of example 1a (0.2 g, 0.6 mmol) was dissolved in 4N HCl in dioxane (10 mL) and stirred under inert atmosphere ($N_2$) for an hour. When the reaction was complete by tlc the solvents were evaporated in vacuo and hexane and diethylether were added. The residue was triturated with these two solvents and the solvents again evaporated in vacuo. This procedure was repeated several times until product was obtained as a glass in quantitative yield. MS(CI) m/e 293(m+H)+.

Step 1c.
N-(3'-Quinolylcarbonyl)-R-valine-di-n-pentylamide

The hydrochloride of example 1b (150 mg, 0.5 mmol), 1-ethyl-3-(3-dimethylaminopropyl) carbodiimide (EDCI, 100 mg), HOBt (135 mg) and quinoline-3-carboxylic acid (88 mg) were stirred at 0° C. under nitrogen in 5 mL of anhydrous $CH_2Cl_2$. To this mixture was added 120 µL of N-methylmorpholine (NMM) and the mixture was stirred overnight (warming to ambient temperature). The reaction mixture was poured into EtOAc and water and the organic extract was washed successively with water, 10% citric acid solution, and saturated aqueous $NaHCO_3$. The solution was dried over $MgSO_4$, filtered and concentrated. The residue was chromatographed using ethylacetate (EtOAc) and hexane as the elutant mixture to provide 110 mg of an oil (54% yield) after removal of the volatiles. $[\alpha]_D = -14.8°$ (c=0.5, MeOH). MS(CI) m/e 412(m+H)+. $^1$H NMR($CDCl_3$,300 MHz) δ 0.92(m,6H), 1.05(m,6H), 1.35(m,8H), 1.5–1.7(m,4H), 2.15(m,1H), 3.05(m,1H), 3.3–3.4(m,1H), 3.5(m,1H), 3.65(m,1H), 5.08(dd,J=3,9 Hz,1H), 7.25(d,J=9 Hz,1H), 7.62(t,J=7 Hz, 1H), 7.8(t,J=7 Hz,1H), 7.91(d,J=10 Hz, 1H), 8.16(d,J=10 Hz,1H), 8.6(d, J=3 Hz,1H), 9.35(d,J=3 Hz,1H). Analysis calculated for $C_{25}H_{37}N_3O_2$: C 72.95, H 9.06, N 10.21; found: $C_{72.61}$, H 9.21, N 9.97.

EXAMPLE 2

N-(2'-Indolylcarbonyl)-R-valine-di-n-pentylamide

The hydrochloride of example 1b (130 mg, 0.45 mmol), EDCI (90 mg), HOBt (120 mg) and indole-2-carboxylic acid (75 mg) were stirred at 0° C. under nitrogen in 5 mL of anhydrous $CH_2Cl_2$. To this mixture was added 100 µL of NMM and the mixture was stirred overnight (warming to ambient temperature). The reaction mixture was poured into EtOAc and water and the organic extract was washed successively with water, 10% citric acid solution, and saturated aqueous $NaHCO_3$. The solution was dried over $MgSO_4$, filtered and concentrated. The residue was chromatographed using EtOAc and hexane as the elutant mixture to provide 36 mg of product (75% yield) after evaporation of the volatiles. mp=132°–4° C. $[\alpha]_D = -9.2°$ (c=0.5, MeOH). MS(CI) m/e 400(m+H)+. $^1$H NMR($CDCl_3$,300 MHz) δ 0.9(t,J=7 Hz,6H), 1.0(m,6H), 1.2–1.4(m,8H), 1.5–1.6(m,4H), 2.12(m, 1H), 3.05(m,1H), 3.3(m,1H), 3.42(m,1H), 3.63(m,1H), 5.0(q,J=3,6 Hz,1H), 7.0(m,1H), 7.1(d,J=9 Hz, 1H), 7.25(t,J=7.5 Hz,1H), 7.3(t,J=7.5 Hz,1H), 7.41(d,J=7 Hz,1H), 7.65 (d,J=7 Hz,1H), 9.3(bs,1H). C,H,N analysis calculated for $C_{24}H_{37}N_3O_2$: C 72.14, H 9.34, N 10.52; found: C 72.52, H 9.25, N 10.49.

EXAMPLE 3

N-(2'-Quinolylcarbonyl)-R-valine-di-n-pentylamide

The reaction was performed in a similar manner to that in example 1c utilizing 0.2 g of the hydrochloride salt of example 1b, quinoline-2-carboxylic acid (0.12 g), EDCI (0.15 g), HOBt (0.1 g), and NMM (6.18 mL). The product was isolated in 80% yield (0.225 g). mp=78°–79° C. $[\alpha]_D = -13.1°$ (c=1.1, MeOH). MS(CI) m/e 412(M+H)+. $^1$H NMR($CDCl_3$,300 MHz) δ 0.9(m,6H), 1.05(m,6H), 1.2–1.4(m,8H), 1.55(m,4H), 2.22(m,1H), 3.08(m,1H), 3.4(m,2H), 3.64(m,1H), 5.0(dd,J=3,7 Hz,1H), 7.62(t,J=7 Hz,1H), 7.78(t,J=7 Hz,1H), 7.85(d,J=9 Hz,1H), 8.15(d,J=9 Hz,1H), 8.35(m,2H), 8.85(d,J=10 Hz,1H). C,H,N analysis calculated for $C_{25}H_{37}N_3O_2$, $H_2O$: C72.17, H 8.96, N 10.10; found: C72.36, H 8.93, N 10.03.

EXAMPLE 4

N-(2'-Benzothiofuranylcarbonyl)-R-valine-di-n-pentylamide

The reaction was performed in a similar manner to that in example 1c utilizing 0.3 g of the hydrochloride salt of example 1b, benzothiofuran-2-carboxylic acid (0.205 g), EDCI (0.22 g) HOBt (0.28 g), and NMM (0.22 mL). The oily product was isolated in 58% yield, 0.28 g $[\alpha]_D = -5.85°$ (c=2.0, MeOH). MS(CI) m/e 417(m+H)+, 158. $^1$H NMR($CDCl_3$,300 MHz) δ 0.9–1.1(m,12H), 1.2–1.3(m,8H), 1.5–1.6(m,4H), 2.15(m,1H), 3.05(m,1H), 3.3(m,1H), 3.42(m,1H), 3.65(m,1H), 5.0(q,J=3,6 Hz,1H), 7.00(d,J=9 Hz,1H), 7.41(m,2H), 7.80(s,1H), 7.86(m,2H). C,H,N analysis calculated for $C_{24}H_{36}N_2O_2S$, 0.25 $H_2O$: C 68.45, H 8.74, N 6.65; found: C68.73, H 8.48, N 6.71.

EXAMPLE 5

N-(4',8'-Dihydroxy-2'-quinolylcarbonyl)-R-valine-di-n-pentylamide

The hydrochloride salt of example 1b (0.95 g, 3.22 mmol) was stirred in 25 mL of $CH_2Cl_2$ with NMM (0.7 mL) under nitrogen at 0° C. EDCI (0.7 g) and HOBt (0.11 g) were added followed by the addition of 4,8-dihydroxyquinoline-2-carboxylic acid (0.66 g, 3.22 mmol). The reaction mixture was stirred overnight (warming to ambient temperature). The solvents were evaporated in vacuo and the residue taken up in EtOAc and washed successively with water, 0.1N solution of HCl, water and brine. The organic solution was dried over $MgSO_4$ and then filtered. Solvents were evaporated in vacuo and the crude product subjected to flash chromatography using EtOAc, hexane and methanol (MeOH) as the elutant mixture. The product was crystallized from MeOH-water to provide 0.82 g (56%). mp=233°-235° C. $[\alpha]_D=-15.6°$ (c=0.5, MeOH). MS(CI) m/e 444(m+H)+. $^1$H NMR(DMSO$d_6$,300 MHz) δ 0.84(m,6H), 0.92(m,6H), 1.1–1.35(m,8H), 1.4–1.6(m,4H), 2.33(m,1H), 3.1–3.45(m,2H), 3.55(m,2H), 4.67(m,1H), 7.1(d,J=9 Hz,1H), 7.42(t,J=7 Hz,1H), 7.55(m,2H), 9.62(d,J=9 Hz,1H), 10.3(s,1H), 11.75(s,1H). C,H,N calculated for $C_{25}H_{37}N_3O_4$: C 67.69 H 8.41, N 9.47; found: C 67.47 H 8.45, N 9.39.

EXAMPLE 6

N-(2'-Benzofuranylcarbonyl)-R-valine-di-n-pentylamide

The reaction was performed in a similar manner to that in example 5 utilizing 0.3 g of the hydrochloride salt of example 1b, benzofuran-2carboxylic acid (0.19 g), EDCI (0.22 g), HOBt (0.28 g), and NMM (0.22 mL). Product was isolated in 56% yield (0.225 g). $[\alpha]_D=-29.2°$ (c=1.1, MeOH). MS(CI) m/e 401(m+H)+. $^1$H NMR (CDCl$_3$,300 MHz) δ 0.9–1.0(m,6H), 1.05(m,6H), 1.25–1.4(m,8H), 1.5–1.68(m,4H), 2.15(m,1H), 3.1(m,1H), 3.28–3.5(m,2H), 3.62(m,1H), 5.0(dd,J=3,6 Hz,1H), 7.28(t,J=5 Hz,1H), 7.4(t,J=8 Hz,2H), 7.45(s,1H), 7.52(d,J=9 Hz,1H), 7.65(d,J=9 Hz,1H). C,H,N analysis calculated for $C_{24}H_{36}N_2O_3$: C71.96, H 9.06, N 6.99; found: C72.09, H 9.08, N 6.99.

EXAMPLE 7

N-[4'-Hydroxy-2'-phenyl-3'-quinolylcarbonyl]-R-valine-di-n-pentylamide

The reaction was performed in a similar manner to that in example 5 utilizing 0.2 g of the hydrochloride salt of example 1b, 4-hydroxy-2-phenyl-quinoline-3-carboxylic acid (0.18 g), EDCI (0.16 g), HOBt (0.19 g), and NMM (0.16 mL). Product was isolated in 64% yield (0.22 g). mp=154°-155° C. $[\alpha]_D=-30.0°$ (c=0.4, MeOH). MS(CI) m/e 504(m+H)+. $^1$H NMR(DMSO$d_6$,300 MHz) δ 0.82(m, 14H), 1.2(m,8H), 1.38(m,4H), 1.94(m,1H), 3.02(m,2H), 3.2(m,1H), 3.4(m,1H), 4.55(m,1H), 7.43(m,5H), 7.7(m,2H), 8.2 (d,J=7 Hz,1H), 12.02(s,1H). C,H,N analysis calculated for $C_{31}H_{41}N_3O_3$: C73.93, H 8.21, N 8.34; found: C73.73, H 8.18, N 8.34.

EXAMPLE 8

N-(7'-Chloro-4'-hydroxy-3'-quinolylcarbonyl)-R-valine-di-n-pentylamide

The reaction was performed in a similar manner to that in example 5 utilizing 5.0 g of the hydrochloride salt of example 1b, 4-hydroxy-7-chloro-quinoline-3-carboxylic acid (3.8 g), EDCI (3.5 g), HOBt (4.6 g), and NMM (3.8 mL) and 10 mL DMF. Product was isolated in 54% yield, 4.25 g. mp=205°-206° C. $[\alpha]D=-93.8°$ (c=0.5, MeOH). MS(CI) m/e 463(m+H)+. $^1$H NMR(DMSO$d_6$, 300 MHz) δ 0.95(m,6H), 1.15(d,J=8 Hz,3H), 1.26(d,J=8 Hz,3H), 1.38 (m,8H), 1.65(m,2H), 1.8(m,1H), 2.0(m,1H), 2.23(m,1H), 3.15(m,1H), 3.35(m,1H), 3.48(m,1H), 3.72(m,1H), 4.6(t,J=6 Hz,1H), 7.2(dd, J=3,9 Hz, 1H), 7.6(d,J=9 Hz,1H) 7.68(d,J=2 Hz,1H), 8.26(d, J=7 Hz,1H), 10.25(d,J=6 Hz,1H), 12.25(d,J=9 Hz,1H). C,H,N analysis calculated for $C_{25}H_{36}Cl_1N_3O_3$: C 64.98, H 7.85, N 9.09, Cl 7.67; found: C 65.16, H 8.04, N 8.94, Cl 7.91.

EXAMPLE 9

N-(4'-Hydroxy-2'-quinolylcarbonyl)-R-valine-di-n-pentylamide

The reaction was performed in a similar manner to that in example 5 utilizing 0.2 g of the hydrochloride salt of example 1b, 4-hydroxyquinoline-2-carboxylic acid (0.13 g), EDCI (0.14 g), HOBt (0.19 g), and NMM (0.15 mL). Product was isolated in 71% yield (0.207 g). mp=70°-71° C. $[\alpha]_D=-13.3°$ (c=0.6, MeOH). MS(CI) m/e 428(m+H)+. $^1$H NMR(DMSO$d_6$,300 MHz) δ 0.85–1.1 (m,12H), 1.2–1.4(m,SH), 1.5–1.7(m,4H), 2.15(m,1H), 3.02(m,1H), 3.25(m,1H), 3.45(m,1H), 3.64(m,1H), 4.95(dd,J=3,6 Hz, 1H), 6.7(bs, 1H), 7.35–7.5(m,2H), 7.65(t,J=7 Hz,2H), 8.35(d,J=8 Hz, 1H), 10.4(bs, 1H). C,H,N analysis calculated for $C_{25}H_{37}N_3O_3$: C 70.22, H 8.72, N 9.83; found: C 69.91, H 8.71, N 9.68.

EXAMPLE 10

N-[Z-2'-Fluoro-3'-phenylprop-2'-enoyl]-R-valine-di-n-pentylamide

The reaction was performed in a similar manner to that in example 1c utilizing 0.27 g of the hydrochloride salt of example 1b, α-fluorocinnamic acid (0.16 g), EDCI (0.19 g), HOBt (0.25 g), and NMM (0.21 mL). The oily product was isolated in an 68% yield, 0.25 g $[\alpha]_D=+7.1°$ (c=1.1, MeOH). MS(CI) m/e 405(m+H)+. $^1$H NMR(CDCl$_3$,300 MHz) δ 0.82–1.0(m,12H), 1.2–1.5(m,8H), 1.5–1.7(m,4H), 2.1(m,1H), 3.05(m,1H), 3.25(m,1H), 3.4(m,1H), 3.6 (m1H), 4.85(m,1H), 7.05(d,J=42 Hz,1H), 7.1(d,J=10 Hz,1H), 7.3–7.45(m,3H), 7.62(d,J=9 Hz,2H). C,H,N analysis calculated for $C_{24}H_{37}FO_2N_2$: C 71.25, H 9.22, N 6.93; found: 70.99, H 9.14, N 6.95.

EXAMPLE 11

N-(2'-Naphthoyl)-R-valine-di-n-pentylamide

The reaction was performed in a similar manner to that in example 1c utilizing 0.2 g of the hydrochloride salt of example 1b, 2-naphthoic acid (0.12 g), EDCI (0.13 g), HOBt (0.18 g), and NMM (0.16 mL). The product was isolated as an oil in 72% yield, 0.2 g. $[\alpha]_D=-13.0°$ (c=1.0, MeOH). MS(CI) m/e 411(m+H)+. $^1$H NMR (CDCl$_3$,300 MHz) δ 0.8–0.9(m,6H), 1.1(m,6H), 1.2–1.4(m,8H), 1.55–1.67(m,4H), 2.13(m,1H), 3.0–3.1(m,1H), 3.25–3.3(m,1H), 3.5 (m, 1H), 3.65(m,1H), 5.08(dd,J=3,6 Hz,1H), 7.11(d,J=9 Hz,1H), 7.52 (m, 2H), 7.9(m,4H), 8.33(s,1H). C,H,N analysis calculated for $C_{26}H_{38}N_2O_2$: C 76.05, H 9.33, N 6.82; found: C 76.20, H 9.32, N 6.98.

EXAMPLE 12

N-[3'-(3''-Pyridyl)prop-2'-enoyl]-R-valine-di-n-pentylamide

The reaction was performed in a similar manner to that in example 1c utilizing 0.3 g of the hydrochloride salt of example 1b, 3-(3'pyridyl)acrylic acid (0.17 g), EDCI (0.22 g), HOBt (0.28 g), and NMM (0.22 mL). An oil was isolated in 76% yield, 0.3 g. $[\alpha]_D = +10.0°$ (c=0.85, MeOH). MS(CI) m/e 388(m+H)+. $^1$H NMR (CDCl$_3$,300 MHz) 0.8–1.05(m,12H), 1.2–1.4(m,8H), 1.45–1.72 (m,4H), 2.06(m,1H), 3.1(m,1H), 3.2–3.5(m,2H), 3.5–3.65(m,1H), 4.92(dd,J=2,6 Hz,1H), 6.6(d,J=15 Hz,1H), 7.28(d,J=9 Hz,1H), 7.3(m, 1H), 7.6(d,J=15Hz,1H), 7.8(d,J=9 Hz,1H), 8.58(d,J=6 Hz,1H), 8.74(d, J=2 Hz,1H). C,H,N analysis calculated for $C_{23}H_{37}N_3O_2$, 0.75 H$_2$O: C 68.88, H 9.68, N 10.48; found: C 68.74, H 9.31, N 10.21.

EXAMPLE 13

N-(1',2',(3'S),4'-Tetrahydrocarbolinyl-3'-carbonyl)-R-valine-di-n-pentylamide

The reaction was performed in a similar manner to that in example 1c utilizing 250 mg of the hydrochloride salt of example 1b, N-L-1,2,3,4-tetrahydroharman-3-carboxylic acid (270 mg), EDCI (160 mg), HOBt (235 mg), and NMM (190 mL). The oily product was isolated in 38% yield (148 mg). $[\alpha]D = -5.5°$ (c=0.2, MeOH). MS(CI) m/e 455(m+H)+. $^1$H NMR(CDCl$_3$,300 MHz) δ 0.8–1.0(m,12H), 1.2–1.35(m,8H), 1.5(m,4H), 1.6(m,1H), 2.05(m,1H), 2.55–2.82(m,1H), 3.1–3.4(m,4H), 3.55(m,2H), 4.1(m,1H), 4.75(m, 1H), 7.0–7.15(m,2H), 7.25(d,J=9 Hz,1H), 7.45(d,J=9 Hz,1H), 7.8(bs,1H), 7.85(bs,1H), 8.26(s,1H). C,H,N analysis calculated for $C_{27}H_{42}N_4O_2$, 0.75 H2O: C 9.27, H 9.36, N 11.97; found: C 69.58, H 9.16, N 11.91.

EXAMPLE 14

N-(1'-Hydroxy-2'-naphthoyl)-R-valine-di-n-pentylamide

The reaction was performed in a similar manner to that in example 1c utilizing 250 mg of the hydrochloride salt of example 1b, 1-hydroxy-2-naphthoic acid (160 mg), EDCI (180 mg), HOBt (240 mg), and NMM (200 μL). Product was isolated in 85% yield (310 mg). mp=85°–86° C. $[\alpha]_D = +90.5°$ (c=0.6, MeOH). MS(CI) m/e 427(m+H)+. $^1$H NMR(CDCl$_3$,300 MHz) δ 0.9(m,6H), 1.05(m, 6H), 1.25–1.4(m,gH), 1.5–1.7(m,4H), 2.15(m,1H), 3.05(m, 1H), 3.25(m,1H), 3.5(m,1H), 3.65(m,1H), 5.06(dd,J=3,9 Hz, 1H), 7.2(d, J=9 Hz,1H), 7.35(d,J=10 Hz,1H), 7.45(d,J=10 Hz,1H), 7.5(dd,J=3,6 Hz, 1H), 7.6(dd,J=3,6 Hz,1H), 7.75(d,J=7 Hz,1H), 8.4(d,J=9 Hz,1H), 10.6 (bs,1H). C,H,N analysis calculated for $C_{26}H_{38}N_2O_3$: C 73.20, H 8.98, N 6.57; found: C 73.24, H 9.02, N 6.55.

EXAMPLE 15

N-(3'-Quinolylcarbonyl)-R-norleucine-di-n-pentylamide

Step 15a, N-(t-Butyloxycarbonyl)-R-norleucine-di-n-pentylamide

N-(t-Butyloxycarbonyl)or-nor-leucine (1.2 g, 5.2 mmol) was stirred at 0° C. in 40 mL of CH$_2$Cl$_2$ with BOPCl (1.5 g, 5.9 mmol), and TEA (0.7 mL, 5.2 mmol). To this reaction mixture was added di-n-pentylamine (2.5 mL, 10.5 mmol). The mixture was stirred overnight and allowed to warm to room temperature. An additional equivalent of BOPCl was added after 18 hrs and the reaction stirred an additional day at ambient temperature. The solvents were evaporated in vacuo and the residue taken up in EtOAc and washed with water, 1N HCl, saturated NaHCO$_3$ solution, water and then the organic solution was dried over MgSO$_4$. After filtration and concentration of the filtrate in vacuo, the residue was chromatographed using EtOAc-hexane as the solvent system in the ratio (1:4). The product was isolated as an oil in 75% yield (1.45 g). MS(CI) m/e 371(m+H)+, $^1$H NMR(CDCl$_3$, 300 MHz) a 0.9–1.2(m,9H), 1.24–1.35(m,12H), 1.5(s,9H), 1.55–1.6 (m,4H), 1.88(m,2H), 3.1(m,1H), 3.32(m,1H), 3.42(m,1H), 3.6(m,1H), 5.15(m,1H), 6.9(d,J=10 Hz,1H).

Step 15b. R-Norleucine-di-n-pentylamide hydrochloride

The product of example 15a (1.4g, 3.8 mmol) was dissolved in 4N HCl in dioxane (25 mL) and stirred at room temperature for an hour. When the reaction was complete by tlc the solvents were evaporated in vacuo and hexane and diethylether were added. The residue was triturated with these solvents and the solid product was filtered away in quantitative yield. $[\alpha]_D = -1.4°$ (c=0.6, MeOH). MS(CI) m/e 27 1(m+H)+. $^1$H NMR(DMSO$_{d6}$, 300 MHz) δ 0.87(m,9H), 1.2–1.4(m,12H), 1.42–1.6(m,4H), 1.7(m,2H), 3.0(m,1H), 3.1–3.3(m,2H), 3.53(m,1H), 4.14(bs,1H), 8.25(bs,2H).

Step 15c. N-(3'-Quinolylcarbonyl)-R-norleucine-di-n-pentylamide

The hydrochloride of example 15b (240 mg, 0.87 mmol), EDCI (170 mg), HOBt (240 mg) and quinoline-3-carboxylic acid (150 mg) were stirred at 0° C. under nitrogen in 20 mL anhydrous CH$_2$Cl$_2$. To this mixture was added 200 μL of NMM and the mixture was stirred overnight (warming to ambient temperature). The reaction mixture was poured into EtOAc and water and the organic extract was washed successively with water, 10% citric acid solution, and saturated aqueous NaHCO$_3$. The solution was dried over MgSO$_4$, filtered and concentrated. The residue was purified by chromatography using EtOAc and hexane as the elutant mixture to provide 200 mg of the glassy product (54% yield) after evaporation of the volatiles. $[\alpha]_D = -10.5°$ (c=1.0, MeOH). MS(CI) m/e 426(m+H)+. $^1$H NMR(CDCl$_3$, 300 MHz) δ 0.9(m,9H), 1.35(m,12H), 1.55(m,2H), 1.65–1.80(m,4H), 3.10(m,1H), 3.25–3.35(m,1H), 3.4(m,1H), 3.55–3.6(m,1H), 5.15(m,1H), 7.4(d, J=9 Hz,1H), 7.6(dd,J=3,7 Hz,1H), 7.8(dd,J=3,7 Hz,1H), 7.9(d,J=9 Hz,1H), 8.15(d,J=9 Hz,1H), 8.6(d,J=2 Hz,1H), 9.35(d,J=3 Hz, 1H). C,H,N analysis calculated for C$_{26}$H$_{39}$N$_3$O$_2$, 0.3 EtOAc: C 72.27, H 9.23, N 9.27; found: C 72.26, H 9.01, N 9.54.

EXAMPLE 16

N-(2'-Indolylcarbonyl)-R-norleucine-di-n-pentylamide

The hydrochloride salt of example 15b (0.30 g, 1.0 mmol) was stirred in 10 mL of CH$_2$Cl$_2$ with NMM (0.2 mL, 2.0 mmol) under nitrogen at 0° C. EDCI (0.2 g, 1.1 mmol) and HOBt (0.27 g, 2.0 mmol) were added followed by the addition of indole-2-carboxylic acid (0.162 g, mmol). The reaction mixture was stirred overnight (warming to ambient temperature). The solvents were evaporated in vacuo, and the residue taken up in EtOAc and washed successively with water, saturated NaHCO$_3$, a saturated solution of citric acid, water and brine. The organic solution was dried over MgSO$_4$ and then filtered. Solvents were evaporated in vacuo and the crude product subjected to flash chromatography using EtOAc and hexane as the elutant mixture. The product was crystallized from EtOAc and hexane to provide a glass 0.285 g (69%). [α]$_D$= −10.6° (c=0.8, MeOH). MS(CI) m/e 414(m+H)+. $^1$H NMR(CDCl$_3$, 300 MHz) δ 0.9(m,9H), 1.2–1.4 (m,10H), 1.5–1.7(m,6H), 1.86(m,2H), 3.15(m,1H), 3.3–3.4(m,2H), 3.58(m,1H), 5.1(m,1H), 7.0(d,J=2 Hz, 1H), 7.15(dd,J=3,7 Hz,1H), 7.3(m,2H), 7.4(d,J=9 Hz,1H), 7.67(d,J=9 Hz, 1H), 9.4(s,1H). C,H,N analysis calculated for C$_{25}$H$_{39}$N$_3$O$_2$, 0.75 H$_2$O: C 70.30, H 9.55, N 9.84; found: C 70.38, H 9.20, N 9.85.

EXAMPLE 17

N-(3'-Quinolylcarbonyl-R-(O-benzyl)serine-di-n-pentylamide

Step 17a.
N-(t-Butyloxycarbonyl)-R-(O-benzyl)serine-di-n-pentylamide

N-(t-Butyloxycarbonyl)-R-(O-benzyl)serine (3.0 g, 10.15 mmol) was stirred at 0° C. in 50 mL of CH$_2$Cl$_2$ with BOPCl (2.8 g, 11 mmol) and 2.0 mL (1.5 mmol) of TEA. To this reaction mixture was added di-n-pentylamine (7 mL, 35 mmol). The mixture was stirred overnight and allowed to warm to room temperature. An additional equivalent of BOPCl was added after 18 hrs and the reaction stirred an additional day at ambient temperature. The solvents were evaporated in vacuo and the residue taken up in EtOAc and washed with water, 1N HCl solution, saturated NaHCO$_3$, water and then the organic solution was dried over MgSO$_4$. After filtration and concentration of the titrate in vacuo, the residue was purified by chromatography using EtOAc-hexane as the elutant system in the ratio (1:4). The product was isolated as an oil in 44% yield (1.9 MS(CI) m/e 435(m+H)+. $^1$H NMR (CDCl$_3$,300 MHz) δ 0.89(m,6H), 1.28(m,8H), 1.4(s,9H), 1.55(m,4H), 3.05–3.2(m,2H), 3.4–3.65(m,4H). 4.5(m,2H), 4.85(m,1H), 5.35(d, J=7 Hz,1H), 7.31(m,5H).

Step 17b. R-(O-Benzyl)serine-di-n-pentylamide hydrochloride

The product of example 17a (0.43 g, 1.0 mmol) was dissolved in 4N HCl in dioxane (10 mL) and stirred under inert atmosphere (N$_2$) for an hour. When the reaction was complete by tlc the solvents were evaporated in vacuo and hexane and diethylether were added. The residue was triturated with these two solvents and the solvents again removed in vacuo. This procedure was repeated several times until the product was obtained as a glassy solid in 93% yield (0.35 g). [α]$_D$= +1.6° (c=0.5, MeOH). MS(CI) m/e 335(m+H)+.

Step 17c.
N-(3'-Quinolylcarbonyl-R-(O-benzyl)serine-di-n-pentylamide

The hydrochloride salt of example 17b (0.35 g, 0.95 mmol) was stirred in 25 mL of CH$_2$Cl$_2$ with NMM, (0.22 mL, 2 mmol) under N$_2$ at 0° C. EDCI (0.19 g, 1.0 mmol) and HOBt (0.27, 2 mmol) were added followed by the addition of quinoline-3-carboxylic acid (0.165 g, 0.95 mmol). The reaction mixture was stirred overnight (warming to ambient temperature). The solvents were evaporated in vacuo and the residue taken up in EtOAc and washed successively with water, saturated NaHCO$_3$, a saturated solution of citric acid, water and brine. The organic solution was dried over MgSO$_4$ and then filtered. Solvents were evaporated in vacuo and the crude product subjected to flash chromatography using EtOAc and hexane as the elutant mixture. The product was crystallized from EtOAc and hexane to provide a semisolid, 0.44 g (94%). [α]$_D$= −4.0° (c=0.45, MeOH). MS(CI) m/e 490(m+H)+. $^1$H NMR(CDCl$_3$,300 MHz) δ 0.9(m,6H), 1.2–1.4(m,SH), 1.5–1.6(m,4H), 3.05–3.28(m,2H), 3.5–3.7(m,2H), 3.8(m,2H), 4.57(m,2H), 5.4(m, 1H), 7.3(m,5H), 7.4(d,J=9 Hz,1H), 7.62(dd,J=2,7 Hz,1H), 7.81(dd, J=2,7 Hz,1H), 7.9(d,J=8 Hz,1H), 8.15(d,J=9 Hz,1H), 8.58(d,J=3 Hz,1H), 9.3(d,J=3 Hz,1H). C,H,N analysis calculated for C$_{30}$H$_{39}$N$_3$O$_3$, 0.75 H$_2$O: C71.61, H 8.11, N 8.35; found: C 71.73, H 8.01, N 8.21.

EXAMPLE 18

N-(3'-Quinolylcarbonyl)-R-phenylalanine-di-n-pentylamide

Step 18a,
N-(t-Butyloxycarbonyl)-R-phenylalanine-di-n-pentylamide

The reaction was performed in a similar manner to that in example 1b utilizing N-(t-Butyloxycarbonyl)-R-phenylalanine (0.8 g, 3.1 mmol), BOPCl (1.2, 4.06 mmol), dipentylamine (3.1 mL, 15 mmol), and TEA (0.4 mL, 3.1 mmol). The oily product was isolated in 65.5% yield (0.87 g). [α]$_D$= +7.0° (c=1.0, MeOH). MS(CI) m/e 405(m+H)+. $^H$ NMR(CDCl$_3$,300 MHz) δ 0.85(m,6H), 1.15–1.45(m,8H), 1.5(s,9H), 1.55–1.6(m,4H), 2.9–3.1(m,5H), 3.5(m,1H), 4.25(m,1H), 5.3(d,J=9 Hz,1H), 7.25(m,5H).

Step 18b. R-Phenylalanine-di-n-pentylamide hydrochloride

The compound was prepared in similar manner to example 1b via deprotection of N-t-Butyloxycarbonyl-R-phenylalanine-di-n-pentylamide, the product of example 18a, using 4N HCl in dioxane. The product was isolated in quantitative yield. MS(CI) m/e 305(m+H)+.

Step 18c.
N-(3'-Quinolylcarbonyl)-R-phenylalanine-di-n-pentylamide

The hydrochloride of example 18b (870 mg, 2.46 mmol), EDCI (550 mg), HOBt (300 mg), and quinoline-3-carboxylic acid (430 mg) were stirred at 0° C. under N$_2$ in 25 mL of anhydrous CH$_2$Cl$_2$. To this mixture was added 550 μL of NMM and the mixture was stirred overnight (warming to ambient temperature). The reaction mixture was poured into EtOAc and water and the organic solution was separated. The organic extract was washed successively with water, 10% citric acid solution, and saturated aqueous NaHCO$_3$. The solution was dried over MgSO$_4$, filtered and concentrated. The residue was purified by chromatography using EtOAc and hexane as the elutant mixture to yield 870 mg of product (77%) after removal of the volatiles. [α]D= +12.9° (c=1.05, MeOH). MS(CI) m/e 460(m+H)+. $^1$H NMR(CDCl$_3$, 300 MHz) δ 0.9(m,6H), 1.15–1.4(m,8H), 1.5–1.55(m,4H), 2.9–3.12 (m,3H), 3.2(m,2H), 3.48–3.6(m,1H), 5.35(m,1H), 7.27(m,5H), 7.48 (d,J=10 Hz,1H), 7.62(t,J=8 Hz,1H), 7.8(t,J=8 Hz,1H), 7.9(d,J=9 Hz, 1H), 8.15(d,J=9 Hz,1H), 8.55(d,J=3 Hz,1H), 9.38(d,J=3 Hz,1H). C,H,N analysis calculated for C$_{29}$H$_{37}$N$_3$O$_2$, 0.5 H$_2$O: C 74.32, H 8.39, N 8.97; found: C 73.92, H 8.05, N 8.83.

EXAMPLE 19

N-(3'-Quinolylcarbonyl)-(2R,3S)-(O-benzyl)threonine-di-n-pentylamide

Step 19a.
N-(t-Butyloxycarbonyl)-(2R,3S)-(O-benzyl)threonine-di-n-pentylamide

The reaction was performed in a similar manner to that in example 1a utilizing N-(t-Butyloxycarbonyl)-D-(O-benzyl)- threonine (5 g, 16.2 mmol), BOPCl (8.2 g, 16.2 mmol), dipentylamine (16 mL, 78.5 mmol), and TEA (2.1 mL, 16.2 mmol). The product was isolated in 58% yield (4.15 g). MS(CI)449(m+H)+. $^1$H NMR(CDCl$_3$,300 MHz) δ 0.85(t,J=6 Hz,6H), 1.18(d, J=6 Hz,3H), 1.2–1.35(m,8H), 1.45(s,9H), 1.5–1.6(m,4H), 3.0–3.18 (m,2H), 3.41–3.63(m,2H), 3.75(m,1H), 4.57(dd,J=12,18 Hz,2H), 4.65(m,1H), 5.5(d,J=9 Hz,1H), 7.30(m,5H).

Step 19b.
(2R,3S)-(O-Benzyl)threonine-di-n-pentylamide hydrochloride

The product of example 19a (1 g, 2.22 mmol) was deprotected and isolated in a similar manner to that in example 1b. The product was isolated as an oil. [α]$_D$= +13.3° (c=1.1, MeOH). MS(CI) m/e 359(m+H)+. $^1$H NMR(DMSO$_{d6}$,300 MHz) δ 0.86(m,6H), 1.08–1.32(m, 11H), 1.48(m,4H), 3.03(m,2H), 3.42(m,2H), 3.88(m, 1H), 4.2(d,J=6 Hz,1H), 4.56(m,2H), 7.35(m,5H), 8.35(bs,2H).

Step 19c.
N-(3'-Quinolylcarbonyl)-(2R,3S)-(O-benzyl)threonine-di-n-pentylamide

The hydrochloride salt of example 19b (0.25 g, 0.65 mmol) was stirred in 15 mL of CH$_2$Cl$_2$ with NMM (0.175 mL, 1.3 mmol) under nitrogen at 0° C. EDCI (0.15 g, 0.8 mmol) and HOBt (0.18 g, 1.3 mmol) were added followed by the addition of quinoline-3-carboxylic acid (0.115 g, 0.65 mmol). The reaction mixture was stirred overnight (warming to ambient temperature). The solvents were evaporated in vacuo and the residue taken up in EtOAc and washed successively with water, saturated NaHCO$_3$, a saturated solution of citric acid, water and brine. The organic solution was dried over MgSO$_4$ and then filtered. Solvents were evaporated in vacuo and the crude product subjected to flash chromatography using EtOAc and hexane as the elutant mixture. The oily product was isolated in 62% yield (0.2 g). [α]$_D$= −4.1° (c=1.0, MeOH). MS(CI) m/e 504(m+H)+. $^1$H NMR(CDCl$_3$,300 MHz) δ 0.9(m,6H), 1.2–1.45(m, 11H), 1.5–1.7(m,4H), 3.0–3.25(m,2H), 3.56–3.7(m,2H), 3.9(m,1H), 4.5(m,2H), 5.3(apparent q,J=4.5 Hz,1H), 7.2–7.3(m,5H), 7.56(d,J=6 Hz,1H), 7.65(t,J=7 Hz,1H), 7.8(t,J=7 Hz,1H), 7.92(d,J=9 Hz,1H) 8.15(d,J=9 Hz,1H), 8.63(d,J=2 Hz,1H), 9.35(d,J=3 Hz, 1H). C,H,N analysis calculated for C$_{31}$H$_{41}$N$_3$O$_3$, 1.6 H$_2$O: C 69.92, H 7.89, N 8.37; found: C 69.81, H 7.78, N 8.08.

EXAMPLE 20

N-(3'-Quinolylcarbonyl)-(2R,3S)-threonine-di-n-pentylamide

The product of example 19c (1 g, 2 mmol) was stirred in 20 mL of CH$_2$Cl$_2$ and 7 mL of borontristrifluoroacetate (1.0M solution in TFA) was added at 0° C. The mixture was stirred approximately 1 hour The tlc revealed some starting material therefore another 5 mL of borontristrifluoroacetate and 5 mL TFA were added. The reaction proceeded overnight to completion by tlc analysis. The reaction mixture was diluted with MeOH and then concentrated in vacuo. The residue was purified by chromatography using EtOAc and hexane as the elutant mixture. The pure fractions were pooled together and the desired product characterized as the di-TFA salt. mp=84°–6° C. [α]$_D$= −11.6° (c=0.55, MeOH). MS(CI) m/e 414(m+H)+. $^1$H NMR(CDCl$_3$,300 MHz) δ 0.85(m,6H), 1.13(d,J=7 Hz, 3H), 1.15–1.38(m,8H), 1.48(m,2H), 1.6(m,2H), 3.1(m,1H), 3.32–3.53(m,4H), 4.05(m,1H), 4.9(t,J=6 Hz,1H), 7.7(t,J=6 Hz,1H), 7.88(t, J=7 Hz,1H), 8.1(d,J=9 Hz,1H), 8.8(d,J=9 Hz,1H), 8.93(bs,1H), 9.31(bs, 1H), 10.02(bs,1H). C,H,N analysis calculated for C$_{24}$H$_{35}$N$_3$O$_3$, 2 CF$_3$CO$_2$H: C 52.42, H 5.81, N 6.55; found: C52.31, H 5.62, N 6.66.

EXAMPLE 21

N-(3'-Quinolylcarbonyl)-(2R,3S)-(O-acetyl)threonine-di-n-pentylamide

Pyridine (20 μL) and acetic anhydride (60 μL) were added to the product of example 20 (51 mg, 0.125 mmol) which was dissolved in acetonitrile (2 mL). The reaction mixture was stirred overnight at room temperature. EtOAc was added and this solution was washed successively with water and brine. The organic solution was dried over MgSO$_4$. After filtration and concentration of the filtrate in vacuo, the residue was purified by chromatography using EtOAc and hexane as the elutant system in the ratio (4:1). The product was isolated as a glass in 44% yield (25 mg). MS(CI) m/e 456(m+H)+. $^1$H NMR(CDCl$_3$, 300 MHz) δ 0.9(m,6H), 1.25–1.45(m, 11H), 1.52(m,2H), 1.7(m,2H), 2.05(s,3H), 3.1(m,2H), 3.3–3.6 (m,3H), 5.28(m,1H), 5.44(m,1H), 7.35(d,J=9 Hz, 1H), 7.65(t,J=7 Hz,1H), 7.82(t,J=7 Hz,1H), 7.95(d,J=7 Hz, 1H), 8.18(d, J=9 Hz,1H), 8.6(d,J=3 Hz,1H), 9.35(d,J=3 Hz,1H). C,H,N analysis calculated for C$_{26}$H$_{37}$N$_3$O$_4$, 0.4 H$_2$O: C 67.48, H 8.23, N 9.08; found: C67.69, H 8.20, N 8.60.

EXAMPLE 22

N-(3'-Quinolylcarbonyl)-(2R,3S)-(O-methyl)threonine-di-n-pentylamide

Lithium bis(trimethylsilyl)amide in tetrahydrofuran (THF) (0.15 mL of 1.0 M solution in THF) was added to a cooled (−10° C.) solution of the product of example 20 (55 mg, 0.14 mmol) in 2 mL THF and then methyl iodide (0.015 mL) was added. The reaction mixture was stirred approximately 1 hour and slowly warmed to room temperature. Tlc revealed some starting material therefore another equivalent of methyl iodide (0.01 mL) was added. The reaction then proceeded to completion by tlc. The reaction mixture was concentrated in vacuo. EtOAc was added to the residue, which was then washed with water and brine. The EtOAc extract was dried over $MgSO_4$. Filtration and concentration of the filtrate in vacuo, provided a residue which was purified by chromatography using EtOAc and hexane as the elutant mixture. An oil was isolated in 47% yield (28 mg). MS(CI) m/e 428(m+H)+. $^1$H NMR(CDCl$_3$,300 MHz) δ 0.92(m,6H), 1.25(d, J=6 Hz,3H), 1.25–1.4(m,8H), 1.55–1.6(m,4H), 3.05(m,1H), 3.2–3.3 (m,2H), 3.35(s,3H), 3.58–3.82(m,2H), 5.25(m,1H), 7.45(d,J=9 Hz, 1H), 7.65(t,J=6 Hz,1H), 7.8(t,J=6 Hz,1H), 7.9(d,J=9 Hz,1H), 8.18(d, J=9 Hz,1H), 8.6(d,J=3 Hz,1H), 9.35(d,J=3 Hz,1H).

EXAMPLE 23

N-(3'-Quinolylcarbonyl)-3-(2'-thienyl)-R-alanine-di-n-pentylamide

Step 23a.
N-(t-Butyloxycarbonyl)-3-(2'-thienyl)-R-alanine-di-n-pentylamide

N-(t-Butyloxycarbonyl)-R-3-(2'-thienyl)-alanine (0.78 g, 3.25 mmol) was stirred at 0° C. in 25 mL of $CH_2Cl_2$ with BOPCl (0.44 g, 3.25 mmol) and 0.5 mL, (3.25 mmol) of TEA. To this reaction mixture was added di-n-pentylamine (2 mL, 10 mmol). The mixture was stirred overnight and allowed to warm to room temperature. An additional equivalent of BOPCl was added after 18 hrs and the reactions stirred an additional day at ambient temperature. The solvents were evaporated in vacuo and the residue taken up in EtOAc and washed with water, 1N HCl solution, saturated $NaHCO_3$ solution, water and then the organic solution was dried over $MgSO_4$. After filtration and concentration of the titrate in vacuo, the residue was purified by chromatography using EtOAc-hexane as the solvent system in the ratio (1:4). The product was isolated as an oil in 57% yield (0.76 g). $[\alpha]_D = -2.27°$ (c=0.66, MeOH). MS(CI) m/e 411(m+H)+, 355, 311. $^1$H NMR(CDCl$_3$,300 MHz) δ 0.85(m,6H), 1.15–1.38(m,10H), 1.45(s,9H), 1.51(m,2H), 3.1(m,4H), 3.22(m,1H), 3.4(m,1H), 4.75 (apparent q,J=10 Hz,1H), 5.45(d,J=9 Hz,1H), 6.83(d,J=6 Hz,1H), 6.9(t,J=4 Hz,1H), 7.15(d,J=6 Hz,1H).

Step 23b. R-3-(2'-Thienyl)-alanine-di-n-pentylamide hydrochloride

The product of example 23a (0.22 g, 0.54 mmol) was deprotected and isolated in the same manner as that in example 1b in quantitative yield. MS(CI) m/e 327(M+H)+.

Step 23c.
N-(3'-Quinolylcarbonyl)-3-(2'-thienyl)-R-alanine-di-n-pentylamide The reaction was performed in a similar manner to that in example 1 c utilizing (80 mg, 0.23 mmol) of the hydrochloride salt of example 23b, quinoline-3-carboxylic acid (40 mg), EDCI (50 mg), HOBt (62 mg), and NMM (51 μL). An oil was isolated in 45% yield (48 mg). MS(CI) m/e 466(m+H)+. $^1$H NMR(CDCl$_3$,300 MHz) δ 0.9(m,6H), 1.2–1.4(m,8H), 1.45–1.65(m,4H), 3.05–3.4(m,4H), 3.45 –3.6(m,2H), 5.35(dd,J=6,7 Hz,1H), 6.87(d,J=3 Hz,1H), 6.94 (m,1H), 7.18(d,J=6 Hz,1H), 7.4(d,J=9 Hz,1H), 7.63(dd,J=3,7 Hz,1H), 7.8(dd, J=3,7 Hz,1H), 7.9(d,J=8 Hz,1H), 8.15(d,J=8 Hz,1H), 8.6(d, J=3 Hz,1H), 9.32(d,J=3 Hz,1H). C,H,N analysis calculated for $C_{27}H_{35}N_3O_2S$, 0.9 $H_2O$: C 67.29, H 7.70, N 8.72; found: C67.60, H 7.47, N 8.98.

EXAMPLE 24

N-(3'-Quinolylcarbonyl)-S-valine-di-n-pentylamide

Step 24a, N-(t-Butyloxycarbonyl)-S-valine-di-n-pentylamide The reaction and product isolation were performed in a similar manner to that in example 1a utilizing N-(t-Butyloxycarbonyl)-S-valine (2.5 g, 11.5 mmol), BOPCl (3.5 g, 13.8 mmol) and dipentylamine (11.6 mL, 58 mmol), and TEA (1.6 mL, 12 mmol). The oily product was isolated in 55% yield (2.25 g). $[\alpha]_D = -21.1°$ (c=1.0, MeOH). MS(CI) m/e 357(m+H)+. $^1$H NMR(CDCl$_3$,300 MHz) 8–0.9(m,6H), 1.05(m,6H), 1.25–1.35(m,SH), 1.45(s,9H), 1.5–1.55 (m,4H), 1.95(m,1H), 3.0(m,1H), 3.2(m,1H), 3.36(m,1H), 3.6(m,1H), 4.4(dt,J=3,7 Hz,1H), 5.24(d,1=9 Hz,1H).

Step 24b. S-Valine-di-n-pentylamide hydrochloride

The product of example 24a (0.2 g, 0.57 mmol) was deprotected and the product isolated as in example 1b in quantitative yield. MS(CI) m/e 257(m+H)+.

Step 24c,
N-(3'-Quinolylcarbonyl)-S-valine-di-n-pentylamide

The reaction sequence was performed in a similar manner to that in example 1c utilizing 175 mg of the hydrochloride salt of example 24b, quinoline-3-carboxylic acid (110 mg), EDCI (125 mg), HOBt (165 mg), and NMM (75 μL). The glassy product was isolated in 80% yield, (198 mg). $[\alpha]_D = +12.95°$ (c=0.8, MeOH). MS(CI) m/e 412(m+H)+$^1$. $^1$H NMR(CDCl$_3$,300 MHz) δ 0.8–1.05 (m,12H), 1.2–1.44(m,8 H), 1.55(m,4H), 2.15(m,1H), 3.1(m,1H), 3.3 (m,1H), 3.5(m,1H), 3.65(m,1H), 5.1(dd,J=3,6 Hz,1H), 7.25(d,J=7 Hz, 1H), 7.62(t,J=7 Hz,1H), 7.8(t,J=7 Hz,1H), 7.9(d,J=8 Hz,1H), 8.15(d, J=9 Hz,1H), 8.61(d,J=3 Hz,1H), 9.35(d,J=3 Hz,1H). C,H,N analysis calculated for $C_{25}H_{37}N_3O_2$, 0.25 $H_2O$: C72.16, H 9.09, N 10.10; found: C72.41, H 9.21, N 9.97.

EXAMPLE 25

N-(2'-Indolylcarbonyl)-R-histidine-di-n-pentylamide

Step 25a.
N-(t-Butyloxycarbonyl)-(N$^{im}$-tosyl)-R-histidine-di-n-pentylamide N-(t-Butyloxycarbonyl)-R-(N$^{im}$-tosyl)-histidine, (4.95 g, 12.6 mmol) was stirred at 0° C. in 50 mL of $CH_2Cl_2$ with BOPCl (3.2 g, 12.6 mmol) and 1.65 mL (12.6 mmol) TEA. To this reaction mixture was added di-n-pentylamine (7.7 mL, 38 mmol). The mixture was stirred overnight and allowed to warm to room temperature. An additional equivalent of BOPCl was added after 18 hrs and the reaction stirred an additional day at ambient temperature. The solvents were evaporated in vacuo and the residue was taken up in EtOAc and washed with water, 1N HCl solution, saturation NaHCO$_3$, water. The organic solution was dried over $MgSO_4$. After filtration and concentration of the filtrate in vacuo, the residue was purified by chromatography using EtOAc-hexane as the solvent system in the ratio (1:4). The product was isolated as an oil in 75% yield (5.1 g). $[\alpha]_D = +8.8°$ (c=1.0, MeOH). MS(CI) m/e 549(m+H)+. 1H NMR(DMSO$_{d6}$, 300 MHz) δ 0.85(m,6H), 1.05-1.46(m,21H), 2.42(s,3H), 2.67(m,2H), 3.03-3.15(m,4H), 4.52(m,1H), 7.0(s,1H), 7.28(d,J=7 Hz,1H), 7.49(d, J=7 Hz,2H), 7.9(d,J=7 Hz,2H), 8.28(s,1H). C,H,N analysis calculated for C$_{28}$H$_{44}$N$_4$O$_5$S: C61.28, H 8.08, N 10.21; found: C 61.04, H 8.05, N 10.10.

Step 25b. (N$^{im}$-Tosyl)-R-histidine-di-n-pentylamide

To a solution of the product of example 25a (6.7 g, 12.21 mmol) in CH$_2$Cl$_2$ (100 mL) was added TFA (40-50 mL). The reaction mixture was stirred at room temperature 60 minutes. When reaction was complete by tlc, the solvents were evaporated several times in vacuo and CH$_2$Cl$_2$ was added with a saturated solution of NaHCO$_3$. The reaction mixture was stirred vigorously another 1 hr and after separation of layers, the organic layer was washed several times with water and brine. The CH$_2$Cl$_2$ layers and washings were dried over MgSO$_4$. The product was then concentrated in vacuo. The semisolid product was isolated and dried in a vacuum oven over P$_2$O$_5$ at room temperature, 5.1 g (93% yield). $[\alpha]_D = -9.4°$ (c=1.0, MeOH). MS(CI) m/e 449(m+H)+, 264, 295. 1H NMR(CDCl$_3$, 300 MHz) δ 0.85(m,6H), 1.1-1.35(m,8H), 1.47-1.6(m,4H), 2.45(s,3H), 2.9-3.2(m,6H), 3.4-3.55(m,2H), 4.5(m,1H), 7.18(s,1H), 7.35(d,J=8 Hz,2H), 7.82(d,J=8 Hz,2H), 7.95(s,1H).

Step 25c.
N-(2'-Indolylcarbonyl)-R-histidine-di-n-pentylamide

The compound of example 25b (170 mg, 0.5 mmol), EDCI (105 mg), HOBt (135 mg) and indole-2-carboxylic acid (85 mg) were stirred at 0° C. under nitrogen in 10 mL of anhydrous CH$_2$Cl$_2$. To this mixture was added 110 μL of NMM and the mixture was stirred overnight (warming to ambient temperature). The reaction mixture was poured into EtOAc and water and the organic extract was washed successively with water, 10% citric acid solution, and saturated aqueous NaHCO$_3$. The solution was dried over MgSO$_4$, filtered and concentrated. The residue was purified by chromatography using chloroform (CHCl$_3$)/MeOH/ammonia as the elutant mixture to provide 98 mg of the semisolid product (45% yield) after evaporation of the volatiles. $[\alpha]_D = +9.8°$ (c=0.46, MeOH). MS(CI) m/e 438(m+H)+, 253, 281. 1H NMR (CDCl$_3$, 300 MHz) δ 0.75-0.95(m,6H), 1.2(m,8H), 1.5(m,4H), 3.13 (m,4H), 3.3(m,1H), 3.4(m,1H), 3.5(m,2H), 5.32(m,1H), 6.8(s,1H), 6.9(s,1H), 7.1(t,J=7 Hz,2H), 7.2(t,J=7 Hz,2H), 7.35(d,J=9 Hz,1H), 7.59 (d,J=9 Hz, 1H), 9.8(s,1H). C,H,N analysis calculated for C$_{25}$H$_{35}$N$_5$O$_2$, 0.5 H$_2$O: C 67.23, H 8.13, N 15.68; found: C 67.24 H 8.06, N 15.24.

EXAMPLE 26

N$^\alpha$-(3'-Quinolylcarbonyl)-N$^\epsilon$-(benzyloxycarbonyl)-R-lysine-di-n-pentylamide Step 26a.
N$^\alpha$-(t-Butyloxycarbonyl)-N$^\epsilon$-(benzyloxycarbonyl)-R-lysine-di-n-pentylamide The reaction was performed in a similar manner to that in example 1a utilizing N$^\alpha$-t-Butyloxycarbonyl-R-(N$^\epsilon$-benzyloxycarbonyl)Lysine (5 g, 13.15 mmol), BOPCl (6.7 g, 26.3 mmol), di-n-pentylamine (26 mL, 131 mmol) and TEA (1.8 mL, 13.5 mmol) in CH$_2$Cl$_2$ (25 mL). The oily product was isolated in 64.5% yield (4.4 g). $[\alpha]_D = +65.3°$ (c=0.15, MeOH). MS(CI) m/e 520(m+H)+. 1H NMR(CDCl$_3$,300 MHz) δ 0.9(m,6H), 1.2-1.35(m, 12H), 1.41(s,9H), 1.5-1.66(m,4H), 3.05-3.25(m,4H), 3.3(m,2H), 3.5(m,2H), 4.53(m,1H), 4.9(m,1H), 5.1(s,2H), 5.38(d,J=9 Hz,1H), 7.3(m,5H).

Step 26b.
N$^\epsilon$-(Benzyloxycarbonyl)-R-lysine-di-n-pentylamide hydrochloride The compound was prepared in similar manner to example 1b via deprotection of the product of example 26a using 4N HCl in dioxane. The product was isolated in quantitative yield. MS(CI) m/e 420(m+H)+.

Step 26c,
N$\alpha$-(3'-Quinolylcarbonyl)-N$^\epsilon$-(benzyloxycarbonyl)-R-lysine di-n-pentylamide The reaction was performed in the similar manner to that in example 1c utilizing 1.0 g of hydrochloride salt of example 26b quinoline-3-carboxylic acid (0.38 g), EDCI (0.45 g), HOBT (0.6 g), and NMM (0.48 mL). The oily product was isolated in 72% yield. $[\alpha]_D = +2.7°$ (c=0.7, MeOH). MS(CI) m/e 575(m+H)+. 1H NMR (CDCl$_3$,300 MHz) δ 0.9(m,6H), 1.3-1.62(m,8H), 1.53(m,6H), 1.65(m, 2H), 1.85(m,2H), 3.05-3.55(m,1H), 5.05(m,11H), 5.15(m,2H), 7.28 (m,5H), 7.55(t,J=8 Hz,1H), 7.8(m,3H), 8.18(d,J=9 Hz,1H), 8.58(d, J=2 Hz,1H), 9.32(d,J=2 Hz,1H). C,H,N calculated for C$_{34}$H$_{46}$N$_4$O$_4$: C71.05, H 8.07, N 9.75; found: C71.00, H 8.18, N 9.68.

EXAMPLE 27

N-(3'-Quinolylcarbonyl)-3-(1'-Naphthyl)-R-alanine-di-n-pentylamide

Step 27a.
N-(t-Butyloxycarbonyl)-3-(1',naphthyl)-R-alanine-di-n-pentylamine

N-(t-Butyloxycarbonyl)-3-(1'-naphthyl)-R-alanine (0.35 g, 1.1 mmol) was stirred at 0° C. in 25 mL of CH$_2$Cl$_2$ with BOPCl, (0.3 g, 1.2 mmol), and 0.15 mL of TEA (1.2 mmol). To this reaction mixture was added di-n-pentylamine (0.8 mL, 4 mmol). The mixture was stirred overnight and allowed to warm to room temperature. An additional equivalent of BOPCl was added after 18 hrs and the reaction stirred an additional day at ambient temperature. The solvents were evaporated in vacuo and the residue taken up in EtOAc and washed with water, 1N HCl solution, saturated NaHCO$_3$, water and then the organic solution was dried over MgSO$_4$. After filtration and concentration of the titrate in vacuo, the residue was purified by chromatography using EtOAc-hexane as the solvent system in the ratio (1:4). The product was isolated as an oil in 65% yield (0.25 g). MS(CI) m/e 455(m+H)+. 1H NMR(CDCl$_3$,300 MHz) α 0.7-0.8(m,6H), 0.9(m,8H), 1.2-1.3(s,4H), 1.35(s,9H), 3.0(m,2H), 3.35(m,2H), 3.5-3.6(m,2H), 4.3(m,1H), 7.4(m,1H), 7.45-7.55(m,2H), 7.6(m,1H), 7.8 (d,J=9 Hz, 1H), 7.85(d,J=9 Hz,1H), 8.35(d,J=9 Hz,1H), 8.9(bs,1H).

Step 27b. 3-(1'-Naphthyl)-R-alanine-di-n-pentylamide hydrochloride

The product of example 27a (0.32 g, 0.72 mmol) was dissolved in 4N HCl in dioxane (10 mL) and stirred under inert atmosphere (N$_2$) for an hour. When the reaction was complete by tlc the solvents were evaporated in vacuo and hexane and diethylether added. The residue was triturated with these two solvents until the product was obtained as a glassy solid in quantitative yield. MS(CI) m/e 391(m+H)+. ¹H NMR(CDCl₃,300 MHz): δ 0.63(m,3H), 0.85(m,3H), 1.05-1.45(m,10H), 1.5-1.72(m,2H), 2.62(m,1H), 2.85(m,1H), 3.6-3.92(m,4H), 4.85(m,1H), 4.73(m,2H), 7.36(m,1H), 7.5(m,1H), 7.7(d,J=6 Hz,1H), 7.75(d,J=6 Hz,1H), 8.35(d,J=8 Hz,1H), 8.92(bs,2H), 9.4(s,1H).

Step 27c.
N-(3'-Quinolylcarbonyl)-3-(1'-Naphthyl)-R-alanine-di-n-pentylamide

The hydrochloride of example 27b (200 mg, 0.52 mmol), EDCI, HOBt (70 mg) and quinoline-3-carboxylic acid (90 mg) were stirred at 0° C. under N₂ in 5 mL of anhydrous CH₂Cl₂. To this mixture was added 10 µL of NMM and the mixture was stirred overnight (warming to ambient temperature). The reaction mixture was poured into EtOAc and water and then the separated organic extract was washed successively with water, 10% citric acid solution, and saturated aqueous NaHCO₃. The solution was dried over MgSO₄, filtered and concentrated. The residue was purified by chromatography using EtOAc and hexane as the elutant mixture to provide 180 mg of the oily product (68% yield) after removal of the volatiles. MS(CI) m/e 510(m+H)+, 280. 1H NMR(CDCl₃,300 MHz) δ 0.72(m,3H), 0.9(m,3H), 1.1-1.45(m,10H), 1.5.1-6(m,2H), 2.38-2.6(m,2H), 2.85(m,1H), 3.47(m,2H), 3.9(m,1H), 5.6(m,1H), 7.35(d,J=6 Hz,2H), 7.52(t,J=7 Hz,2H), 7.6-7.7(m,3H), 7.72-7.93(m,3H), 8.15(d,J=9 Hz,1H) 8.55(d,J=9 Hz,1H), 8.6(d,J=3 Hz,1H), 9.4(d,J=3 Hz,1H).

EXAMPLE 28

N-(3'-Quinolylcarbonyl)-3-(2'-Naphthyl)-R-alanine-di-n-pentylamide

Step 28a.
N-(t-Butyloxycarbonyl)-3-(2'-naphthyl)-R-alanine-di-n-pentylamide

N-(t-Butyloxycarbonyl)-3-(2'-naphthyl)-R-alanine (0.31 g, 1.0 mmol) was stirred at 0° C. in 25 mL of CH₂Cl₂ with BOPCl, (0.38 g, 1.5 mmol) and 0.2 mL of TEA (1.5 mmol). To this reaction mixture was added di-n-pentylamine (0.7 mL, 3.5 mmol). The mixture was stirred overnight and allowed to warm to room temperature. An additional equivalent of BOPCl was added after 18 hrs and the reaction stirred an additional day at ambient temperature. The solvents were evaporated in vacuo and the residue taken up in EtOAc and washed with water, 1N HCl solution, saturated NaHCO₃, and water. The organic solution was dried over MgSO₄. After filtration and concentration of the filtrate in vacuo, the residue was purified by chromatography using EtOAc-hexane as the solvent system in the ratio (1:4). The product was isolated as an oil in 62% yield (0.28 g). MS(CI) m/e 455(m+H)+, 355.

Step 28b. 3-(2'-Naphthyl)-R-alanine-di-n-pentylamide hydrochloride

The product of example 28a (0.28 g, 0.6 mmol) was dissolved in 4N HCl in dioxane (10 mL) and stirred under N₂ for an hour. When the reaction was complete by tlc the solvents were evaporated in vacuo and then hexane and diethylether were added. The residue was triturated with these two solvents until the product was obtained as a glassy solid in 93% yield. MS(CI) m/e 355(m+H)+.

Step 28c.
N-(3'-Quinolylcarbonyl)-3-(2'-Naphthyl)-R-alanine-di-n-dipentylamide

The reaction was performed in a similar manner to that in example 1c utilizing 75 mg of hydrochloride salt of example 28b, quinoline-3carboxylic acid (34 mg), EDCI (40 mg), HOBt (50 mg), and NMM (22 µL). The oily product was isolated in 31% yield, (32 mg). MS(CI) m/e 510 (m+H)+. ¹H NMR(CDCl₃,300 MHz) δ 0.85(m,6H), 1.06-1.35 (m,12H), 2.85(m,1H), 3.0(m,2H), 3.35(m,2H), 3.55(m,1H), 5.45(apparent q,J=7 Hz,1H), 7.32-7.5(m,4H), 7.62(t, J=6 Hz,1H), 7.68-7.82(m,5H), 7.88(d,J=7 Hz,1H), 8.15(d,J=7z, 1H), 8.52(d,J=2 Hz,1H).

EXAMPLE 29

N-(3'-Quinolylcarbonyl)-R-histidine-di-n-pentylamide

The free base of example 25b (3.7 g, 9.26 mmol), EDCI, (1.7 g, 9 mmol), HOBt (3.65 g) and 1.5 g quinoline-3-carboxylic acid were stirred at 0° C. in 50 mL of anhydrous dimethylformamide (DMF) and CH₂Cl₂ in 1:1 ratio. After reaction was complete by tlc, solvents were evaporated under vacuum and the residue dissolved in large excess of EtOAc (300 mL). Water was added and the organic extract was washed with 10% citric acid solution, and saturated NaHCO₃. The solution was dried over MgSO₄, filtered and concentrated. The residue was purified by chromatography using CHCl₃-MeOH arid ammonium hydroxide as the elutant mixture to provide 1.98 g (68.3%) product. [α]D=−6.4° (c=0.25, MeOH). MS(CI) m/e 450(m+H)+, 156. ¹H NMR (CDCl₃,300 MHz) δ 0.9(m,6H), 1.29(m,8H), 1.45-1.6(m,4H), 3.08-3.2(m,3H), 3.23-3.4(m,2H), 3.5-3.6(m,1H), 5.3(apparent q,J=9 Hz, 1H), 6.85(s,1H), 7.6(m,3H), 7.(t,J=6H,1H), 7.88(d,J=8 Hz,1H), 7.97(d, J=8 Hz,1H), 8.15(d,J=5 Hz,1H), 8.6(d,J=3 Hz,1H), 9.3(d,J=3 Hz,1H). N-(3'-Quinolylcarbonyl)-(N$^{im}$-tosyl)-R-histidine-di-n-pentylamide (0.2 g) also was isolated refer to example 30.

EXAMPLE 30

N-3'-Quinolylcarbonyl-(N$^{im}$-tosyl)-R-histidine-di-n-pentylamide

The title compound of example 30 was isolated as a side product in the procedure in example 29. [α]$_D$=+13.3° (c=1.05, MeOH). MS(CI) m/e 604(m+H)+, 450. ¹H NMR(CDCl₃,300 MHz) δ 0.9(m,6H), 1.3(m,8H), 1.45-1.7(m,4H), 2.25(s,3H), 3.0-3.13(m,3H), 3.25(m,1H), 3.35(m,1H), 3.5(m,1H), 5.36(apparent q,J=6 Hz,1H), 7.15(m,3H), 7.6(t,J=7 Hz,1H), 7.7(d,J=9 Hz,2H), 7.8-7.9(m,2H), 7.95(d,J=2 Hz,1H), 8.13(d,J=7 Hz,1H), 8.45(d,J=3 Hz,1H), 9.18(d, J=3 Hz,1H). C,H,N analysis calculated for C₃₃H₄₁N₅O₄S: C 65.64, H 6.85, N 11.60; found: C 65.58, H 6.84, N 11.50.

EXAMPLE 31

N-(3'-Quinolylcarbonyl )-R-lysine-di-n-pentylamide

To a suspension of 0.5 g 10% Pd/C in MeOH (25 mL) and cyclohexadiene (3 mL) under N₂ was added a solution of the product of example 26c (0.51 g, 0.89 mmol) in MeOH via cannula. The reaction mixture was stirred overnight at ambient temperature. Cyclohexadiene (2 mL) was added and the reaction was continued overnight. The mixture was filtered through celite and washed several times with MeOH. The flitrate and washings were combined and concentrated in vacuo. The residue was subjected to flash chromatography using CHCl3-MeOH and ammonium hydroxide 90:10:1 as the elutant mixture. Lyophilization provided product in 64% yield (0.25 g). MS(CI) m/e 441(m+H)+. $^1$H NMR(DMSO$_{d6}$,300 MHz) δ 0.85(m,6H), 1.15–1.35(m,8H), 1.4–1.65(m,4H), 1.7(m,2H), 1.75(m,2H), 2.7(m,2H), 3.1–3.5(m,8H), 4.9(m,1H), 7.7(t,J=6 Hz,1H), 7.88(t,J=6 Hz,1H), 8.1(d,J=8 Hz,2H), 8.9(d,J=3 Hz,1H), 9.0(d,J=3 Hz,1H), 9.3(d,J=3 Hz,1H). C,H,N analysis calculated for C$_{26}$H$_{40}$N$_4$O$_2$, H$_2$O: C 69.45, H 8.97, N 12.46; found: C 69.48, H 8.76, N 12.03.

EXAMPLE 32

N-(3'-Quinolylcarbonyl)-R-(4'-hydroxyphenyl)glycine-di-n-pentylamide

Step 32a.
N-(t-Butyloxycarbonyl)-R-(4'-Hydroxyphenyl)glycine-di-n-pentylamide

The reaction was performed in a similar manner to that in example 1a utilizing N-(t-Butyloxycarbonyl)-R-4'-hydroxy phenylglycine (5 g, 18.7 mmol), BOPCl (5.1 g, 20 mmol), dipentylamine (8 mL, 37 mmol), and TEA (2.6 mL). The product was isolated in 78% yield (5.9 g). MS(CI) m/e 407(m+H)+. $^1$H NMR(CDCl$_3$,300 MHz) δ 0.85(m,6H), 1.1–1.35(m,8H), 1.3(s,9H), 1.45–1.58(m,4H), 3.0(m,1H), 3.15(m,2H), 3.45(m,1H), 5.42(d,J=9 Hz,1H), 6.02(d,J=9 Hz,1H), 6.5(s,1H), 6.75(d,J=9 Hz,2H), 7.18(d,J=9 Hz,2H).

Step 32b.
R-(4'-Hydroxyphenyl)-glycine-di-n-pentylamide hydrochloride

The compound was prepared in similar manner to example 1b via deprotection of the product of example 32a, using 4N HCl in dioxane. The oily product was isolated in 90% yield. [α]$_D$=−87.0° (c=0.2, MeOH). MS(CI) m/e 307(m+H)+. $^1$H NMR(DMSO$_{d6}$, 300 MHz) δ 0.82(m,6H), 1.02–1.2(m,8H), 1.3–1.5(m,4H), 3.05–3.3(m,2H), 3.32–3.4(m,2H), 5.22(bs,1H), 6.83(d,J=9 Hz,2H), 7.25(d,J=9 Hz,2H), 8.4(bs,3H).

Step 32c.
N-(3'-Quinolylcarbonyl)-R-(4'-hydroxyphenyl)glycine-di-n-pentylamide

The reaction was performed in a similar manner to that in example 1c utilizing (300 mg, 2.6 mmol) of hydrochloride salt of example 32b, quinoline-3-carboxylic acid (450 mg), EDCI (550 mg), HOBt (380 mg), and NMM (0.62 mL). Product was isolated in 53% yield (0.78 g). mp=79°–80° C. [α]$_D$=−99.6° (c=1.0, MeOH). MS(CI) m/e 462(m+H)+. $^1$H NMR(CDCl$_3$,300 MHz) δ 0.85(t,J=7 Hz, 6H), 1.1–1.3(m,10H), 1.4–1.5(m,2H), 3.1–3.2(m,2H), 3.25–3.5 (m,2H), 5.9(d,J=9 Hz,1H), 6.6(d,J=9 Hz,2H), 7.25(d,J=9 Hz,2H), 7.7(t,J=7 Hz,1H), 7.85(t,J=7 Hz,1H), 8.08(d,J=9 Hz,2H), 8.9(d,J=3 Hz, 1H), 9.1(d,J=6 Hz,1H), 9.25(d,J=3 Hz, 1H), 9.53(s,1H). C,H,N analysis calculated for C$_{28}$H$_{35}$N$_3$O$_3$: C 72.85, H 7.64, N 9.10; found: C 72.65, H 7.65, N 9.08.

EXAMPLE 33

N-(8'-Hydroxy-2'-quinolylcarbonyl)-R-valine-di-n-pentylamide

The title compound was prepared in a similar fashion to that in example 1c. mp=143°–4° C. MS(CI) m/e 428(m+H)+, 243, 158. $^1$H NMR(CDCl$_3$,300 MHz) δ 8.58(d,J=10 Hz,1H), 8.31(s,2H), 8.09(s,1H), 7.54(m,1H), 7.39(dd,J=1,8 Hz,1H), 7.24(m,1H), 5.01(dd,J=7,10 Hz, 1H), 3.65(dt,J=7,16 Hz,1H), 3.28–3.55(m,2H), 3.06(dt,J=7,14 Hz,1H), 2.22(septet,J=7 Hz,1H), 1.50–1.75(m,4H), 1.25–1.42(m,8H), 1.06(d,J=7 Hz,3H), 1.03(d,J=7 Hz,3H), 0.92(t,J=7 Hz,3H), 0.89(t,J=7 Hz,3H). C,H,N analysis calculated for C$_{25}$H$_{37}$N$_3$O$_3$, 0.1 H$_2$O: C 69.93, H 8.73, N 9.79; found: C 69.78, H 8.51, N 9.61.

EXAMPLE 34

N-(2'-Methylphenylaminocarbonyl)-R-valine-di-n-pentylamide

A solution of hydrochloride of example 1b (0.15 g, 0.52 mmol), 2-methyl-phenylisocyanate (0.1 g) and TEA (0.1 mL) was allowed to react at ambient temperature. The solvent was removed in vacuo and the residue dissolved in EtOAc. Water was added and the mixture extracted several times with EtOAc. The combined EtOAc extracts were washed with brine and dried over MgSO$_4$. The volatiles were removed in vacuo and the residue purified by chromatography. The oily product was isolated in 80% yield. 1.5° (c=0.4, MeOH). MS(CI) m/e 390(m+H)+. $^1$H NMR (CDCl$_3$,300 MHz) δ 0.8–1.0(m,12H), 1.12–1.41(m,8H), 1.42–1.78 (m,4H), 2.01(m,1H), 2.22(s,3H), 3.25(m,1H), 3.35(m,2H), 3.51(m, 1H), 4.7(m,1H), 6.5(m,1H), 6.7(s,1H), 7.04(t,J=6 Hz,1H), 7.16(m,2H), 7.53(d,J=9 Hz,1H). C,H,N analysis calculated for C$_{23}$H$_{39}$N$_3$O$_2$: C 70.91, H 10.09, N 10.79; found: C 70.57, H 9.46, N 10.57.

EXAMPLE 35

N$^α$-(3'-Quinolylcarbonyl)-N$^ε$-(2'-Chlorobenzyloxycarbonyl)-R-lysine-di-n-pentylamide Step 35a. N$^α$-(t-Butyloxycarbonyl)-N$^{-68}$ (2'-Chlorobenzyloxycarbonyl)-R-lysine-di-n-pentylamide N$^α$-(t-Butyloxycarbonyl)-N$^ε$-(2'-chlorobenzyloxycarbonyl)-R-lysine (1.0 g, 2.4 mmol) was stirred at 0° C. in 25 mL of CH$_2$Cl$_2$ with BOPCl, (0.65 g, 2.6 mmol), and TEA (0.35 mL, 2.4 mmol). To this reaction mixture was added di-n-pentylamine (2.5 mL, 12 mmol). The mixture was stirred overnight and allowed to warm to room temperature. An additional equivalent of BOPCl was added after 18 hrs and the reaction stirred an additional day at ambient temperature. The solvents were evaporated in vacuo and the residue taken up in EtOAc and washed with water, 1 N HCl soution, saturated NaHCO$_3$, and water. The organic solution was dried over MgSO$_4$. After filtration and concentration of the filtrate in vacuo, the residue was purified by chromatography using EtOAc-hexane as the solvent system in the ratio (1:4). The product was isolated as an oil in 53% yield (0.7 g). MS(CI) m/e 554(m+H)+, 326. $^1$H NMR(CDCl$_3$,300 MHz) δ0.9(m,6H), 1.2–1.38 (m,12H), 1.42(s,9H), 1.5–1.7(m,4H), 3.02–3.45(m,4H), 3.48(m,4H), 4.5(m,1H), 5.01(m,1H), 5.2(s,2H), 5.4(d,J=9 Hz,1H), 7.25(m,2H), 7.3–7.45(m,2H).

Step 35b.
$N^\epsilon$-(2'-Chlorobenzyloxycarbonyl)-R-lysine-di-n-pentylamide hydrochloride The compound was prepared in similar manner to example 1b via deprotection of the product of example 35a, using 4 N HCl in dioxane. The product was isolated in quantitative yield. MS(CI) m/e 454(m+H)+, free base.

Step 35c.
$N^\epsilon$-(3'-Quinolylcarbonyl)-$N^\epsilon$-(2'-chlorobenzyloxycarbonyl)-R-lysine-di-n-pentylamide The hydrochloride salt of example 35b (0.5 g, 1.02 mmol) was stirred in 15 mL of $CH_2Cl_2$ with NMM (0.24 mL, 2.2 mmol) under $N_2$ at 0° C. EDCI (0.25 g, 1.3 mmol) and HOBt (0.3 g, 2.2 mmol) were added followed by the addition of quinoline-3-carboxylic acid (0.1 g, 1.1 mmol). The reaction mixture was stirred overnight and allowed to slowly warm to ambient temperature. The solvents were evaporated in vacuo and the residue taken up in EtOAc and washed successively with water, saturated $NaHCO_3$, a saturated solution of citric acid, water and brine. The organic solution was dried over $MgSO_4$ and then filtered. Solvents were evaporated in vacuo and the crude product subjected to flash chromatography using EtOAc and hexane as the elutant mixture. The product was isolated as an oil, 0.46 g (74%). MS(CI) m/e 609(m+H)+. $^1$H NMR(CDCl$_3$,300 MHz) δ 0.8–0.96(m,6H) 1.16–1.42(m,12H), 1.45–1.6(m,2H), 1.8–2.0(m,2H), 2.7(m,2H), 3.07–3.45(m,4H), 3.5–3.65(m,2H), 5.15(m,3H), 6.85(d,J=12 Hz,1H), 7.2 (d,J=9 Hz,2H), 7.4(d,J=9 Hz,2H), 7.6(m,2H), 7.8(t,J=7 Hz,1H), 7.9(t, J=7 Hz,1H), 8.15(d,J=9 Hz,1H), 8.6(s,1H), 9.35(d,J=3 Hz,1H). C,H,N analysis calculated for $C_{34}H_{45}ClN_4O_4$, 0.6 $H_2O$: C 65.86, H 7.41, N 9.04; found: C 65.63, H 7.29, N 9.42.

EXAMPLE 36
$N^\alpha$-(3'-Quinolylcarbonyl)-$N^\epsilon$-(acetyl)-R-lysine-di-n-pentylamide The reaction was performed in a similar manner to that in example 21 utilizing 60 mg of the product of example 31 and pyridine with acetic anhydride. The oily product was purified by standard chromatography and isolated in 33% yield (22 mg). [α]$_D$= −1.3° (c=0.5, MeOH). MS(CI) m/e 483(m+H)+. $^1$H NMR (CDCl$_3$,300 MHz) δ 0.92(m,6H), 1.23–1.4(m,8H), 1.45–1.7(m,8H), 1.8(m,2H), 1.98(s,3H), 3.1(m,1H), 3.25(m,2H), 3.32(m,1H), 3.6 (m,2H), 5.15(m,1H), 5.85(bs,1H), 7.5(d,J=8 Hz,1H), 7.65(t,J=6 Hz, 1H), 7.82(t,J=6 Hz,1H), 7.94(d,J=8 Hz,1H), 8.18(d,J=8 Hz,1H), 8.62(d, J=2 Hz,1H), 9.36(d,2 Hz,1H).

EXAMPLE 37
N-(5'-Hydroxyindolyl-2'-carbonyl),R-valine-di-n-pentylamide

The 5-hydroxyindole-2-carboxylic acid (95 mg), hydrochloride of example 1b (150 mg), NMM (0.12 mL), HOBt (70 mg), and EDCI (105 mg) reacted under similar conditions to those described in example 1c. The product was isolated in 74% yield. MS(CI) m/e 416(m+H)+. $^1$H NMR(CDCl$_3$,300 MHz) δ 0.9(m,6H), 1.0(apparent q,J=7 Hz,6H), 1.32(m,8H), 1.62(m,4H), 2.11(m,1H), 3.15(m,1H), 3.2(m,1H), 3.43(m,1H), 3.62(m,1H), 4.95(m,1H), 5.6(s,1H), 6.78(m, 1H), 6.88(dd,J=2,9 Hz,1H), 6.98(d,J=9 Hz,1H), 7.02(d,J=2 Hz, 1H), 7.25(d,J=9 Hz,1H), 9.3(s,1H).

EXAMPLE 38
$N^\alpha$-(3'-Quinolylcarbonyl)-$N^\epsilon$-[E-3'-(4''-chlorophenyl)-prop-2'-enoyl]-R-lysine-di-n-pentylamide

Step 38a. 4-Chlorocinnamic acid N-hydroxysuccinimide ester

To a solution of 4-chlorocinnamic acid (0.8g, 4.38 mmol) in $CH_2Cl_2$ was added N-hydroxysuccinimide (0.55 g, 4.8 mmol) and EDCI and the reaction mixture was stirred at ambient temperature overnight. The solvents were removed in vacuo and the residue dissolved in EtOAc and water. Combined EtOAc extracts were dried over $MgSO_4$ and the solution concentrated in vacuo. The residue was crystallized from a mixture of EtOAc and hexane. The product was isolated in 72% yield (0.88g). mp=192°–193° C. MS(CI) m/e 297(m+NH$_4$+). $^1$H NMR(DMSOd$_6$,300 MHz) δ 2.87(s,4H), 7.05(d,J=17 Hz,1H), 7.56(d,J=9 Hz,2H), 7.92(d,J=9 Hz,2H), 7.99(d,J=17 Hz,1H).

Step 38b.
$N^\alpha$-(3'-Quinolylcarbonyl)-$N^\epsilon$-[E-3'-(4''-Chlorophenyl)-prop-2'-enoyl]-R-lysine-di-n-pentylamide To a solution of example 31 (60 mg, 0.14 mmol) in DMF (8 mL) cooled to 0° C. were added NMM (35 μL) and the active ester of example 38a (40 mg,0.14 mmol). The mixture was stirred overnight with warming to ambient temperature. The DMF was removed in vacuo and the residue was chromatographed on silica using EtOAc-hexane as the elutant mixture. The oily product was isolated in 40% yield (35 mg). MS(CI) m/e 605(m+H)+. $^1$H NMR (CDCl$_3$,300MHz) δ 0.92(m, 6H), 1.3(m,8H), 1.62(m,8H), 1.83(m,2H), 3.14(m,1H), 3.35(m,4H), 3.58(m,1H), 5.15(m,1H), 6.18(m,1H), 6.35 (d,J=17 Hz,1H), 7.25(m, 6H), 7.48(d,J=17 Hz,1H), 7.62(t,J=8 Hz,1H), 7.83(t,J=8 Hz,1H), 8.15(d,J=9 Hz,1H), 8.62(d,J=2 Hz,1H), 9.37(d,J=2 Hz, 1H).

EXAMPLE 39
N,O-Di-(3'-Quinolylcarbonyl)-R-tyrosine-di-n-pentylamide

Step 39a,
N-(t-Butyloxycarbonyl)-R-tyrosine-di-n-pentylamide

N-t-Butyloxycarbonyl-R-tyrosine (4.5 g, 15.4 mmol) was stirred with BOPCl (3.92 g, 15.4 mmol) and dipentylamine (7.9 mL, 39 mmol) in 100 mL of THF at 4° C. and allowed to warm to room temperature overnight. After one day, additional BOPCl (800 mg) was added and, after two days, the volatiles were evaporated. The residue, dissolved in EtOAc, was extracted with 0.1M citric acid solution, 0.1M sodium carbonate ($Na_2CO_3$) solution, and water; then dried over $MgSO_4$, filtered and concentrated in vacuo to yield an oil, 5.67 g, 13.4 mmol (87.4%). R$_f$=0.45 (2:1 hexanes-EtOAc). [α]$_D$= +2.8° (c=0.76, MeOH). MS(CI) m/e 421(m+H)+. $^1$H NMR(CDCl$_3$,300 MHz) δ 0.88(apparent q,J=7 Hz,6H), 1.15–1.32(m, 10H), 1.36–1.47(m,11H), 2.80–3.07(m,5H), 3.38–3.48(m,1H), 4.72 (apparent q,J=6 Hz,1H), 5.41(d,J=8 Hz,1H), 6.70(d,J=8 Hz,2H), 7.02(d, J=8 Hz,2H).

Step 39b. R-Tyrosine-di-n-pentylamide hydrochloride

The product of example 39a (2.0 g, 4.75 mmol) was dissolved in 4N HCl in dioxane (20 mL, 80 mmol) that was precooled to 4° C. After 3 hours, the excess reagent was evaporated and the oily residue was placed under high vacuum overnight to yield a glass, 1.5 g, 4.2 mmol (87%). $[\alpha]_D = -42.8°$ (c=1.2, MeOH). MS(CI) m/e 321 (m+H)+. $^1$H NMR(DMSO$_{d6}$,300 MHz) δ 0.82–0.89(m,6H), 1.1–1.4(m,12H), 2.70–3.04(m,5H), 3.37–3.50(m,1H), 4.22(dd,J=5,7 Hz, 1H), 6.70(d,J=8 Hz,2H), 6.99(d,J=8 Hz,2H), 8.37(bs,3H), 9.48(s,1H).

Step 39c.
N,O-Di-(3'-Quinolylcarbonyl)-R-tyrosine-di-n-pentylamide

The product of example 39b (357 mg, 1 mmol), quinoline-3-carboxylic acid (173 mg, 1 mmol), HOBt (13 mg, 0.1 mmol), and TEA (279 μL, 2 mmol) were dissolved in 10 mL CH$_2$Cl$_2$ and EDCI (191 mg, 1 mmol) was then added in one portion. After 3 days, the volatiles were evaporated and the residue, in EtOAc, was extracted as in example 41a. The residue was then purified by chromatography on silica gel eluted with 1% ethanol (EtOH) in CHCl$_3$ to provide first the mono-acylated material (19 mg, see example 46) followed by an oily product, (108 mg, 0.17 mmol, 17% yield). R$_f$=0.36 (18:1 CHCl$_3$-EtOH). $[\alpha]_D = +5.8°$ (c=0.5, CHCl$_3$). $[\alpha]_D = +53.2°$ (c=0.73 MeOH). MS(CI) m/e 631(m+H)+, 518, 458, 446, 368. $^1$H NMR(CDCl$_3$,300 MHz) δ 0.88–0.94(m,6H), 1.22–1.41(m,10H), 1.50–1.59(m,2H), 2.96–3.30(m,5H), 3.52–3.62 (m,1H), 5.33–5.42(m,1H), 7.22(d,J=8 Hz,1H), 7.30(d,J=8 Hz,1H), 7.37 (d,J=8 Hz,2H), 7.63(dt,J=1,7 Hz,1H), 7.68(dt,J=1,7 Hz,1H), 7.79–7.93 (m,3H), 8.0(dd,J=1,8 Hz,1H), 8.16(d,J=8 Hz,1H), 8.22(d,J=8 Hz,1H), 8.56(d,J=2 Hz,1H), 9.02(d,J=2 Hz,1H), 9.32(d,J=2 Hz,1H), 9.54(d, J=2 Hz,1H). C,H,N analysis calculated for C$_{39}$H$_{42}$N$_4$O$_4$, H$_2$O: C 72.20, H 6.84, N 8.64; found: C 72.38, H 6.62, N 8.50.

EXAMPLE 40

N-(2'-Indolylcarbonyl)-R-tyrosine-di-n-pentylamide

The product of example 39b (200 mg, 0.56 mmol), indole-2-carboxylic acid (97 mg, 0.6 mmol) and TEA (84 μL, 0.6 mmol) were dissolved in 5 mL CH$_2$Cl$_2$ and treated with EDCI (115 mg, 0.6 mmol) at room temperature. After 3 days, the solvent was evaporated and the residue was extracted as in example 39a. Column chromatography on silica gel eluted with 1% EtOH in CH$_2$Cl$_2$ provided product. R$_f$=0.38 (18:1 CH$_2$Cl$_2$-EtOH). mp=124°–7° C. $[\alpha]_D = +21.4°$ (c=1.17, MeOH). MS(CI) m/e 464(m+H)+. $^1$H NMR(CDCl$_3$,300 MHz) δ 0.88(apparent q,J=8 Hz,6H), 1.15–1.56(m, 12H), 2.46–3.22(m,5H), 3.48–3.54(m,1H), 5.23–5.32(m,1H), 6.12(s, 1H), 6.70(d,J=8 Hz,2H), 6.95(d,J=1Hz,1H), 7.05(d,J=8 Hz,2H), 7.13(dt, J=1,7 Hz,1H), 7.18(d,J=8 Hz,1H), 7.27(dt,J=1,7 Hz,1H), 7.40(d,J=8 Hz,1H), 7.64(d, J=8 Hz,1H), 9.22(s,1H). C,H,N analysis calculated for C$_{28}$H$_{37}$N$_3$O$_3$: C 72.54, H 8.05, N 9.06; found: C 72.37, H 8.10, N 8.80.

EXAMPLE 41

N-(3',4'-Dichlorobenzoyl)-R-tyrosine-di-n-pentylamide

The product of example 39b (103 mg, 0.29 mmol) was dissolved in 5 mL CH$_2$Cl$_2$ and treated with 3,4-dichlorobenzoylchloride (126 mg, 0.6 mmol) and TEA (84 gL, 0.6 mmol) at room temperature. After 2 hours, additional acid chloride (13 mg) and TEA (8 μL) were added and the reaction was stirred overnight. The volatiles were evaporated and the residue, in EtOAc, was extracted with 0.1% citric acid, H$_2$O; then dried over MgSO$_4$, filtered and concentrated in vacuo. The resulting diacylated product residue was dissolved in 10 mL of 1:1 THF-MeOH and treated with 1 N NaOH (290 mL, 0.29 mmol). After 1 hour, tlc revealed complete reaction and the solvent was evaporated in vacuo. The residue was dissolved in EtOAc and acidified with 0.1M citric acid. The EtOAc layer was then washed until neutral, dried over MgSO$_4$, filtered and concentrated in vacuo. The residue was warmed with 80% aqueous EtOH and cooled overnight to provide a solid, 64 mg, 0.13 mmol (45% yield). mp=148°–52° C. $[\alpha]_D = +15.6°$ (c=1.0, MeOH). MS(CI) m/e 493(m+H)+. $^1$H NMR(CDCl$_3$,300 MHz) δ 0.88–0.92(m,6H), 1.2–1.6(m,12H), 2.93–3.22(m,5H), 3.50–3.60(m, 1H), 5.21–5.28(m,1H), 6.29(s,1H), 6.68(d,J=8 Hz,2H), 7.02(d,J=8 Hz, 2H), 7.15(d,J=8 Hz,1H), 7.47(d,J=8 Hz,1H), 7.59(dd,J=2,8 Hz,1H), 7.91 (d,J=2 Hz,1H). C,H,N analysis calculated for C$_{26}$H$_{34}$Cl$_2$N$_3$: C 63.28, H 6.94, N 5.68; found: C 63.39, H 7.00, N 5.54.

EXAMPLE 42

N-(2'-Naphthoyl)-R-tyrosine-di-n-pentylamide

The product of example 39b (100 mg, 0.28 mmol) was acylated with 2-naphthoic acid (52 mg, 0.30 mmol) in the presence of TEA (39 μL, 0.28 mmol) and EDCI (57 mg, 0.30 mmol) in 5 mL CH$_2$Cl$_2$. The reaction and extractive workup were performed as in example 41a to yield 120 mg, 0.25 mmol (89%). mp=128°–133° C. $[\alpha]_D = +11.8°$ (c=0.68, MeOH). MS(CI) m/e 475(m+H)+, 303, 290. $^1$H NMR(CD$_3$OD,300 MHz) δ 0.88–0.93(m,6H), 1.19–1.38(m,9H), 1.44–1.62(m,3H), 2.99(dd,J=7,13 Hz,1H), 3.08–3.29(m,4H), 3.37–3.47(m,1H), 5.22(dd,J=7,9 Hz,1H), 6.72(d,J=8 Hz,2H), 7.13(d,J=8 Hz, 2H), 7.53–7.62(m,2H), 7.84(dd,J=2,9 Hz,1H), 7.90–7.99(m,3H), 8.37 (s,1H). C,H,N analysis calculated for C$_{30}$H$_{38}$N$_2$O$_3$: C 75.91, H 8.07, N 5.90; found: C 75.57, H 7.97, N 5.83.

EXAMPLE 43

N-(3'-Quinolylcarbonyl)-(O-benzyl)-R-tyrosine-di-n-pentylamide

Step 43a.
N-t-Butyloxycarbonyl-(O-benzyl)-R-tyrosine-di-n-pentylamide

N-t-Butyloxycarbonyl-(O-benzyl)-R-tyrosine (3.71 g, 10 mmol) was stirred with di-n-pentylamine (5.1 mL, 25 mmol), HOBt (1.4 g, 10 mmol) and TEA (1.4 mL, 10 mmol) in 150 mL CH$_2$Cl$_2$ at 4° C. and then BOPCl (2.6 g, 10 mmol) was added. The reaction was allowed to reach room temperature overnight. After one day, additional BOPCl (260 mg) and TEA (140 μL) were added. After 2 days, the volatiles were evaporated and the residue (in EtOAc) was extracted with 0.1 M H$_3$PO$_4$, 0.1M Na$_2$CO$_3$, H$_2$O; then dried over MgSO$_4$, filtered and concentrated in vacuo. The residue was chromatographed on silica gel eluted with 2:1 hexanes-EtOAc to yield an oil, 1.3 g, 2.55 mmol (25%). $[\alpha]_D = +5.8°$ (c=1.5, MeOH). MS(CI) m/e 511 (m+H)+, 456, 393. $^1$H NMR(CDCl$_3$,300 MHz) δ 0.84–0.93(m,6H), 1.1–1.35(m, 12H), 1.41(s,9H), 2.81–3.04(m,5H), 3.36–3.46(m,1H), 4.15–4.23(m,1H), 5.03(s,2H), 5.32(d,J=8 Hz,1H), 6.87(d,J=8 Hz,2H), 7.11(d,J=8 Hz,2H), 7.32–7.43(m,5H).

Step 43b. (O-Benzyl)-R-tyrosine-di-n-pentylamide hydrochloride

The product of example 43a (1.3 g, 2.55 mmol) was treated with 5 mL of 4 N HCl in dioxane, precooled to 4° C. The reaction mixture was then allowed to reach room temperature. After 1 hour tlc revealed complete reaction and the excess reagent was evaporate. The residue was placed under high vacuum overnight to yield an oil, 1.2 g. $R_f$=0.59 (80:20:1 CHCl$_3$-MeOH-ammonium hydroxide). $[\alpha]_D$= −32.5° (c=2.2, MeOH). MS(CI) m/e 411(m+H)$^+$. $^1$H NMR(DMSO$_{d6}$,300 MHz) δ 0.85(apparent q,J=7 Hz,6H), 1.07–1.38(m,12H), 2.68–2.97(m,4H), 3.05(dd, J=5,13 Hz,1H), 3.32–3.42 (m,2H), 4.27(dd,J=5,8 Hz,1H), 5.09(s,2H), 6.93(d,J=8 Hz,2H), 7.12(d, J=8 Hz,2H), 7.32–7.43(m,5H), 8.37(s,3H).

Step 43c. N-(3'-Quinolylcarbonyl )-(O-benzyl )-R-tyrosine-di-n-pentylamide

EDCI (290 mg, 1.5 mmol) was added to a cooled (4° C.) solution of quinoline-3-carboxylic acid (260 mg, 1.5 mmol), the product of example 43b (650 mg, 1.35 mmol), and TEA (418 μL, 3.0 mmol) in 5 mL CH$_2$Cl$_2$. The stirred reaction mixture was allowed to warm to room temperature overnight. After evaporation of the volatiles, the residue was dissolved in EtOAc and extracted with 0.1M H$_3$PO$_4$ (3×), 0.1M Na$_2$CO$_3$ (3×), brine (3×); then dried over MgSO$_4$, filtered and concentrated in vacuo to yield an oil, 650 mg, 1.15 mmol (85%). $R_f$=0.77 (18:1 CHCl$_3$-EtOH), 0.40 (1:1 hexanes-EtOAc). $[\alpha]_D$= +0.21° (c=0.47, CHCl$_3$). MS(FAB) m/e 566(m+H)$^+$, 393, 381. $^1$H NMR(CDCl$_3$,300 MHz) δ 0.91(apparent q,J=7 Hz,6H), 1.17–1.38(m,10H), 1.43–1.6(m,2H), 2.86–3.17(m,5H), 3.49–3.59(m, 1H), 5.03(s,2H), 5.26–5.33(m,1H), 6.90(d,J=8 Hz,2H), 7.16(d,J=8 Hz, 2H), 7.28–7.43(m,6H), 7.62(dt,J=1,7 Hz,1H), 7.82(dt,J=1,8 Hz,1H), 7.90(d,J=8 Hz,1H), 8.18(d,J=8 Hz,1H), 8.54(d,J=2 Hz,1H), 9.32(d, J=2 Hz,1H). C,H,N analysis calculated for C$_{36}$H$_{43}$N$_3$O$_3$: C 76.55, H 7.88, N 7.29; found: C 76.43, H 7.66, N 7.43.

EXAMPLE 44

N-(3'-Quinolylcarbonyl)-R-tyrosine-di-n-pentylamide

The product of example 43c (614 mg, 1.09 mmol) was dissolved in 30 mL MeOH and treated with 10% Pd/C (200 mg, pre-wetted with solvent under nitrogen) under 1 atmosphere hydrogen gas. Another 200 mg of catalyst was added after 4 hours and the reaction mixture was stirred overnight. The mixture was then filtered and the filtrate concentrated in vacuo. Silica gel column chromatography of the residue (eluted with a 2:1 to 1:1 hexane-EtOAc step gradient) provided 270 mg, 0.57 mmol (52% yield). mp=135°–37° C. $[\alpha]_D$= +12.6° (c=0.5, MeOH). MS(CI) m/e 476(m+H)$^+$, 347, 321,291. $^1$H NMR(CDCl$_3$,300 MHz) δ 0.91(t, J=7 Hz,6H), 1.24–1.38(m,8H), 1.48–1.62(m,4H), 3.0–3.28 (m,5H), 3.51–3.61(m,1H), 5.30–5.38(m,1H), 6.72(d,J=8 Hz,2H), 6.78(s,1H), 7.06(d,J=8 Hz,2H), 7.38(d,J=8 Hz,1H), 7.60(t,J=7 Hz,1H), 7.80(dt, J=1,7 Hz,1H), 7.88(d,J=8 Hz,1H), 8.15(d,J=9 Hz,1H), 8.58(d, J=2 Hz,1H), 9.27(d,J=2 Hz,1H). C,H,N analysis calculated for C$_{29}$H$_{37}$N$_3$O$_3$: C 73.23, H 7.84, N 8.83; found: C 73.23, H 7.89, N 8.76.

EXAMPLE 45

N-(3'-Quinolylcarbonyl)-(O-bisulfatyl)-R-tyrosine di-n-pentylamide ammonium salt The product of example 44 (59 mg, 0.12 mmol) was dissolved in 2 mL DMF and treated with freshly prepared pyridine-sulfur trioxide complex (H. C. Reitz et al J. Amer. Chem. Soc. 68, 1031–5, 1946) overnight at room temperature. The pyridine was evaporated in vacuo and the DMF solution was poured into water and the pH adjusted to 7 with 1 N NaOH. The homogeneous solution was then frozen and lyophilized. Preparative C-18 chromatography of the residue eluted with a gradient from 100% aqueous buffer (0.05M ammonium acetate, pH 6.2) to 50% acetonitrile/aqueous buffer over 10 minutes provided product fractions which were pooled, frozen and lyophilized to yield 48 mg, 0.08 mmol (67%). mp=113°–6° C. $[\alpha]_D$= +12.2° (c=0.88, MeOH). MS(FAB) m/e 554(m-H)$^+$, 368, 302, 298. $^1$H NMR(D$_2$O, 300 MHz) δ 0.68–0.75(m,6H), 0.98–1.43(m,12H), 2.98–3.28(m,6H), 5.22(t,J=7 Hz,1H), 7.24(d,J=8 Hz,2H), 7.30(d,J=8 Hz,2H), 7.44(t,J=8 Hz, 1H), 7.62(d,J=8 Hz,1H), 7.69(t,J=8 Hz,1H), 7.82(d,J=8 Hz, 1H), 8.36(s, 1H), 8.78(s,1H). C,H,N analysis calculated for C$_{29}$H$_{40}$ N$_4$O$_6$S, 0.50 H$_2$O: C 59.88, H 7.10, N 9.63; found: C 59.77, H 6.82, N 9.11.

EXAMPLE 46

3,5-Di-iodo-N-(3'-quinolylcarbonyl)-R-Tyr-di-n-pentylamide and
3-Iodo-N-(3'-quinolylcarbonyl)-R-Tyr-di-n-pentylamide

Example 46a.
3.5-Di-iodo-N-(3'-quinolylcarbonyl)-R-Tyr-di-npentylamide

Iodine (27 mg, 0.11 mmol) was mixed with morpholine (40 μL, 0.46 mmol) in 5 mL MeOH and added to the product of example 46 (50 mg, 0.11 mmol) in 15 mL MeOH at room temperature. The reaction was stirred until tlc indicated complete reaction. After evaporation of the solvent, chromatography of the residue on silica gel eluted with a step gradient of CHCl$_3$ to 1% EtOH in CHCl$_3$ provided first the diiodo product followed by the monoiodo compound. Diiodo product (a): $[\alpha]_D$= +18° (c=0.11, MeOH). MS(CI) m/e 728(m+H)$^+$, 602. $^1$H NMR(CDCl$_3$,300 MHz) δ 0.92 (apparent q,J=7 Hz,6H), 1.2–1.45(m,12H), 2.92–3.13(m,5H), 3.53–3.67(m,1H), 5.22–5.28(m,1H), 5.72(s,1H), 7.27(d,J=7 Hz,1H), 7.56(s, 2H), 7.63(dt,J=1,8 Hz,1H), 7.83(dt,J=18 Hz,1H), 7.93(d,J=8 Hz,1H), 8.18(d,J=1,8 Hz,1H), 8.55(d,J=2 Hz,1H), 9.33(d,J=2 Hz,1H). C,H,N analysis calculated for C$_{29}$H$_{35}$I$_2$N$_3$O$_3$, 0.4 EtOAc: C 48.19, H 5.05, N 5.51; found: C 48.43, H 5.03, N 5.79.

Example 46b.
3-Iodo-N-(3'-quinolylcarbonyl)-R-Tyr-di-n-pentylamide

Monoiodo product (b): mp=75°–85° C. MS(CI) m/e 602(m+H)$^+$. $^1$H NMR(CDCl$_3$,500 MHz) δ 0.84(apparent q,J=7 Hz,6H), 1.13–1.35 (m,9H), 1.37–1.53(m,3H), 2.90–2.98(m,3H), 3.02–3.08(m,2H), 3.48–3.55(m,1H), 5.18–5.23(m,1H), 6.83(d,J=8 Hz,1H), 7.05(dd,J=1,8 Hz, 1H), 7.22(d,J=8 Hz,1H), 7.46(d,J=2 Hz,1H), 7.57(dt,J=1,8 Hz,1H), 7.76 (dt,J=1,8 Hz,1H), 7.84(d,J=8 Hz,1H), 8.10(d,J=8 Hz,1H), 8.48(d,J=2

Hz, 1H), 9.24(d,J=2 Hz,1H). C,H,N analysis calculated for $C_{29}H_{36}IN_3O_3$, 1.5 $H_2O$: C 55.42, H 6.25, N 6.69; found: C 55.19, H 5.95, N 6.17.

EXAMPLE 47

N-(3'-Quinolylcarbonyl)-(O-methyl)-R-tyrosine-di-n-pentylamide

The product of example 44 (25 mg, 0.053 mmol) was dissolved in 1 mL acetone and $K_2CO_3$ (8 mg, 0.058 mmol) and methyl iodide (5 μL 0.08 mmol) were added. After 3 hours at reflux, additional methyl iodide (5 mL) and acetone (2 mL) were added. After 2 days, the volatiles were evaporated and the residue, in EtOAc, was extracted with 0.1% aqueous citric acid, water; then dried over $MgSO_4$, filtered and concentrated in vacuo. MS(CI) m/e 490(m+H)+, 476, 361,347, 317. $^1$H NMR(CDCl$_3$,300 MHz) δ 0.86–0.93(m,6H), 1.2–1.56(m,12H), 2.42–3.15(m,5H), 3.49–3.59(m,1H), 3.78(s,3H), 5.27–5.34(m,1H), 6.77(d,J=8 Hz,1H), 6.82(d,J=8 Hz,1H), 7.08(d,J=8 Hz,1H), 7.16(d,J=8 Hz,1H), 7.41–7.46(m,1H), 7.56–7.63 (m,1H), 7.76–7.82(m,1H), 7.83–7.88(m,1H), 8.14(d,J=8 Hz,1H), 8.53(d,J=2 Hz, 1H), 9.29(t,J=2 Hz,1H).

EXAMPLE 48

Methyl N-(3'-quinolylcarbonyl)-(O-benzyl)-R-tyrosyl-S-phenylglycinate

Step 48a. Methyl N-t-Butyloxycarbonyl-(O-benzyl)-R-tyrosyl-S-phenylglycinate N-t-Butyloxycarbonyl-(O-benzyl)-R-tyrosine (1.0 g, 2.7 mmol), methyl S-phenylglycinate hydrochloride (540 mg, 2.7 mmol), HOBt (362 mg, 2.7 mmol) and TEA (374 μL, 2.7 mmol) were dissolved in 20 mL THF and treated with BOPCl (682 mg, 2.7 mmol). The reaction was followed by tlc (18:1 CHCl$_3$-EtOH) and additional BOPCl (200 mg) and TEA (374 μL) were added after 1,2 and 4 days. $CH_2Cl_2$ (20 mL) also was added after 2 days. After 1 week, the volatiles were evaporated in vacuo and the residue, in EtOAc, was extracted as in example 39a. Chromatography of the residue on silica gel eluted with a step gradient from 9:1 to 2:1 hexanes-EtOAc yielded 485 mg, 1.13 mmol (42%). mp=138°-39° C. [α]$_D$=+48.7° (c=1.0, MeOH). MS(CI) m/e 519(m+H)+, 463,419. $^1$H NMR(CDCl$_3$,300 MHz) δ 1.41(s,9H), 2.92–3.04(m,2H), 3.71(s,3H), 4.35(bs,1H), 5.01(s,3H), 5.43–5.46(m,1H), 6.78(d,J=7 Hz, 1H), 6.82(d,J=8 Hz,2H), 7.02(d,J=8 Hz,2H), 7.19–7.23(m,1H), 7.30–7.45(m,10H).

Step 48b. Methyl (O-Benzyl)-R-tyrosyl-S-phenylglycinate hydrochloride

The product of example 48a (450 mg, 1.05 mmol) was dissolved in 4 N HCl in dioxane (5 mL, 20 mmol) precooled to 4° C. After 1 hour, the excess reagent was evaporated in vacuo and the product used directly in the next step. mp=163°-6° C. [α]$_D$=+43.7° (c=0.76, MeOH). MS(FAB) m/e 419(m+H)+, 403,226. $^1$H NMR(DMSO$_{d6}$,300 MHz) δ 2.86–3.00(m,2H), 3.67(s,3H), 4.13(bt, J=5 Hz,1H), 5.03(s,2H), 5.45(d,J=7 Hz,1H), 6.88(d,J=8 Hz,2H), 7.05(d, J=8 Hz,2H), 7.22–7.25(m,2H), 7.33–7.46(m,8H), 8.28(s,3H), 9.35(d, J=7 Hz,1H).

Step 48c. Methyl N-(3'-quinolylcarbonyl)-(O-benzyl)-R-tyrosyl-S-phenylglycinate Quinoline-3-carboxylic acid (182 mg, 1.05 mmol), TEA (146 μL, 1.05 mmol) and the product of example 48b (1.05 mmol) were dissolved in 20 mL $CH_2Cl_2$ and EDCI (201 mg, 1.05 mmol) was added at ambient temperature. After 4 days, the volatiles were evaporated and the residue was extracted as in example 39a. The solvents were evaporated in vacuo to provide 407 mg, 0.71 mmol (68% yield). top=153°-8° C. [α]$_D$=+73.0° (c=1.2, CHCl$_3$-MeOH/1:1). MS(FAB) m/e 574(m+H)+, 419, 381. $^1$H NMR(CDCl$_3$, 300 MHz) δ 3.06(dd,1=8,14 Hz,1H), 3.20(dd,J=5,14 Hz,1H), 3.70(s,3H), 4.94–5.02(m,3H), 5.53(d,J=7 Hz,1H), 6.78(d,J=8 Hz, 2H), 6.83(d, J=7 Hz,1H), 7.01(d,J=8 Hz,2H), 7.14(d,J=7 Hz,1H), 7.20–7.23(m,2H), 7.33–7.36(m,4H), 7.39–7.44(m,4H), 7.62(dt,J=1,7 Hz, 1H), 7.82(dt, J=1,7 Hz,1H), 7.88(d,J=8 Hz,1H), 8.15(d,J=8 Hz,1H), 8.54(d,J=2 Hz,1H), 9.28(d,J=2 Hz,1H). C,H,N analysis calculated for $C_{35}H_{31}N_3O_5$, 0.5 $H_2O$: C 72.15, H 5.54, N 7.21; found: C 72.05, H 5.63, N 6.88.

EXAMPLE 49

Methyl N-(3'-quinolylcarbony)-R-tyrosy-S-phenylglycinate

The product of example 48c (200 mg, 0.35 mmol) was dissolved in 10 mL $CH_2Cl_2$ and treated with trimethylsilyliodide (TMSI, 198 μL, 1.39 mmol) at room temperature. Additional TMSI (198 μL) was added after 1 day. After 3 days, the reaction was quenched with MeOH for 5 minutes and then poured into 0.1M citric acid and extracted with EtOAc (3×). The combined EtOAc solution was washed with water; then dried over $MgSO_4$, filtered and concentrated in vacuo. The crude solid was purified by chromatography on silica gel eluted with a step gradient of 1 to 5% EtOH in $CH_2Cl_2$ and then crystallized from EtOAc and hexane to yield 51 mg (30%). mp=238°-40° C. [α]$_D$=+72.6° (c=0.23, MeOH). MS(CI) m/e 484(m+H)+, 319. $^1$H NMR(CDCl$_3$-CD$_3$OD,300 MHz) δ3.0–3.16(m,2H), 3.72(s,3H), 4.92–5.01(m,1H), 5.50(d,J=7 Hz,1H), 6.67(d,J=8 Hz,2H), 6.99(d,J=8 Hz,2H), 7.21–7.24(m,2H), 7.35–7.38(m,3H), 7.40(s,1H), 7.68(dt,J=1,7 Hz, 1H), 7.86(dt,J=1,7 Hz,1H), 7.98(d,J=8 Hz,1H), 8.12(d,J=8 Hz,1H), 8.14(d,J=6 Hz,1H), 8.22(d, J=8 Hz,1H), 8.68(d,J=2 Hz,1H), 9.21(d, J=2 Hz,1H). C,H,N analysis calculated for $C_{28}H_{25}N_3O_5$: C 69.55, H 5.21, N 8.69; found: C 69.20, H 5.29, N 8.60.

EXAMPLE 50

N-(2'-Quinolylcarbonyl)-homoserine-di-n-pentylamide

Step 50a. N'-Benzyloxycarbonyl-(2,R)-aminobutyrolactone

N-Benzyloxycarbonyl-R-methionine (283 mg, 1.0 mmol) and α-iodo acetamide (555 rag, 3.0 mmol) were dissolved in 6 mL of 50% aqueous EtOH and warmed to 4° C. for 4 days. Citric acid was added (3 mL of a 0.1M solution) and the mixture was refluxed for 4 hours. After evaporation of the volatiles, the residue was poured into water and extracted with EtOAc (3×). The combined EtOAc solution was extracted with 0.5 N HCl, water; then dried and concentrated vacuo. The resulting residue was chromatographed on silica gel eluted with 1:1 hexanes-EtOAc to yield 106 mg, 0.52 mmol (52%). (cf: Ozinskas, A. J., Rosenthal, G. A., J. Organic Chem. 51, 5047, 1986). mp=124°-5° C. [α]$_D$= +31.3° (c=1.2, MeOH). $^1$H NMR(CDCl$_3$, 300 MHz) δ 2.16-2.28 (m,1H), 2.76-2.86(m,1H), 4.2-4.31(m,1H), 4.37-4.50(m,2H), 5.13(s,2H), 5.32(bs,1H), 7.32-7.38(m,5H).

Step 50b.
N-Benzyloxycarbonyl-homoserine-di-n-pentylamide

The product of example 50a (620 mg, 2.8 mmol) and dipentylamine (1.4 mL, 7 mmol) were dissolved in 60 mL acetonitrile and then heated to reflux overnight. After evaporation of the volatiles, the residue was chromatographed on silica gel eluted with a step gradient from CHCl$_3$ to 1% EtOH in CHCl$_3$ to yield an oil, 580 mg, 1.6 mmol (56%). [α]$_D$= +0.31° (c=0.96, MeOH). MS(CI) m/e 393(m+H)$^+$, 253, 236, 192. $^1$H NMR(CDCl$_3$,300 MHz) δ 0.87-0.93(m,6H), 1.22-1.38 (m,8H), 1.47-1.63(m,4H), 1.86-1.97(m,1H), 3.01-3.20(m,2H), 3.34-3.43(m,2H), 3.52-3.72(m,4H), 4.76(dt,J=3,11 Hz,1H), 5.1(d,J=12 Hz, 1H), 5.13(d, J=12 Hz,1H), 5.93(d,J=8 Hz,1H), 7.31-7.38(m,5H).

Step 50c.
N-(2'-Quinolylcarbonyl)-homoserine-di-n-pentylamide

The product of example 50b is subjected to deprotection conditions as in example 44 and then subsequently coupled with 2-quinoline carboxylic acid in a manner as in example 1.

EXAMPLE 51

N-(2'-Indolylcarbonyl)-R,S-homoserine-di-n-pentylamide

Step 51a.
N'-(2'-Indolylcarbonyl)-(2,RS)-aminobutyrolactone

EDCI (191 mg, 1.0 mmol) was added to a solution of indole-2-carboxylic acid (161 mg, 1.0 mmol), α-aminobutyrolactone hydrobromide (182 mg, 1.0 mmol), HOBt (135 mg, 1.0 mmol), and TEA (279 μL, 2.0 mmol) in 15 mL CH$_2$Cl$_2$ at room temperature. Additional EDCI (120 mg) and TEA (56 μL) were added after 1 day. After 5 days, the volatiles were evaporated and the residue, in EtOAc, was extracted with 1M H$_3$PO$_4$, 0.1M Na$_2$CO$_3$, and brine. The solution was dried over MgSO$_4$, filtered and concentrated in vacuo. The product was crystallized from EtOAc to yield 147 mg, 0.6 mmol, 60%. R$_f$=0.17 (1:1 hexanes-EtOAc). mp=235°-6° C. MS(CI) m/e 245(m+H)+144. $^1$H NMR(CDCl$_3$-CD$_3$OD,300 MHz) δ 1.86-2.51(m,1H), 2.19-2.79(m,1H), 4.32-4.42 (m,1H), 4.56(dt,J=2,11 Hz,1H), 4.82(dd,J=8,11 Hz,1H), 7.1-7.15(m, 2H), 7.28(dt, J=1,8 Hz,1H), 7.40(s,0.5 H), 7.46(d,J=8 Hz,1H), 7.66(d, J=8 Hz,1H).

Step 51 b.
N-(2'-Indolylcarbonyl)-R,S-homoserine-di-n-pentylamide

The product of example 51a (25 mg, 0.1 mmol) and dipentylamine (50 μL, 0.25 mmol) were dissolved in 2 mL THF and warmed to 50° C. Additional dipentylamine (250 μL) was added after several hours. After 4 days, the volatiles were evaporated and the residue was chromatographed on silica eluted with 2:1 hexanes-EtOAc. Yield: 26 mg, 0.06 mmol, 60%. mp=128°-139° C. MS(CI) m/e 402(m+H)$^+$, 158. $^1$H NMR(CDCl$_3$, 300 MHz) δ 0.92(t,J=7 Hz,6H), 1.26-1.42(m,10H), 1.52-1.72(m,3H), 1.98-2.11(m,1H), 2.69(t,J=8 Hz,1H), 3.06-3.26(m,2H), 3.42-3.52(m, 1H), 3.60-3.77(m,3H), 5.12-5.20(m,1H), 7.03(d,J=1Hz,1H), 7.16(dt, J=1,8 Hz,1H), 7.31(dt,J=1,7 Hz,1H), 7.42(dd,J=1,8 Hz,1H), 7.48(d, J=8 Hz,1H), 7.67(d,J=8 Hz,1H), 9.13(s,1H). C,H,N analysis calculated for C$_{23}$H$_{35}$N$_3$O$_3$, 0.5 H$_2$O: C 67.28, H 8.84, N 10.24; found: C 67.42, H 8.64, N 10.10.

EXAMPLE 52

N-(3'-Quinolylcarbonyl)-R,S-homoserine-di-n-pentylamide

Step 52a.
N'-(3'-Quinolylcarbonyl)-(2,RS)-aminobutyrolactone

Quinoline-3-carboxylic acid (5.2 g, 30 mmol) was coupled to α-aminobutyrolactone (5.5 g, 30 mmol) in a manner similar to that in example 51a to provide 2.62 g, 10.2 mmol (34% yield). Additional extraction of the aqueous layer with EtOAc yielded another 820 mg, 3.2 mmol (10.7%). R$_f$=0.26 (18:1 CHCl$_3$-EtOH). mp=160°-63° C. MS(CI) m/e 257(m+H)$^+$. $^1$H NMR(CDCl$_3$,300 MHz) t5 2.32-2.46(m,1H), 2.91-3.01(m,1H), 4.35-4.43(m,1H), 4.56(dt, J=2,10 Hz,1H), 4.83-4.92(m,1H), 7.36(d,J=6 Hz,1H), 7.60(dt,J=1,8 Hz, 1H), 7.81(dt,J=2,8 Hz,1H), 7.86(d,J=8 Hz,1H), 8.12(dd,J=1,8 Hz,1H), 8.59(dd,J=1,2 Hz,1H), 9.28(d,J=2 Hz,1H). C,H,N analysis calculated for C$_{14}$H$_{12}$N$_3$: C 65.61, H 4.72, N 10.93; found: C 65.42, H 4.82, N 10.82.

Step 52b,
N-(3'-Quinolylcarbonyl)-R,S-homoserine-di-n-pentylamide

The product of example 52a (500 mg, 2.0 mmol) was treated with dipentylamine (1.5 mL, 7.4 mmol) in 25 mL of toluene and refluxed. After 2 days, an additional 1 mL of dipentylamine was added and the heating was continued. After 1 week, the volatiles were evaporated in vacuo and the excess amine was removed by Kugelrohr distillation. The residue was then chromatographed on silica gel eluted with a step gradient of CHCl$_3$ to 4% EtOH in CHCl$_3$ to yield an oil, 611 mg, 1.48 mmol (74%). MS(CI) m/e 414(m+H)$^+$. $^1$H NMR(CDCl$_3$,300 MHz) δ 0.88-0.95(m,6H), 1.25-1.42(m,7H), 1.52-1.75(m,5H), 2.04-2.15(m,1H), 3.06-3.28(m,2H), 3.46-3.57(m, 2H), 3.62-3.81(m,3H), 4.01(dd,J=5,9 Hz,1H), 5.21-5.28(m,1H), 7.63 (dt,J=1,8 Hz,1H), 7.72(d,J=7 Hz,1H), 7.83(dt,J=1,8 Hz,1H), 7.93(dd, J=1,7 Hz,1H), 8.18(d,J=8 Hz,1H), 8.62(d,J=2 Hz,1H), 9.37(d,J=3 Hz,1H). C,H,N analysis calculated for C$_{24}$H$_{35}$N$_3$O$_3$, 0.25 H$_2$O: C 68.95, H 8.56, N 10.05; found: C 69.26, H 8.45, N 10.06.

EXAMPLE 53

N-(3'-Quinolylcarbonyl)-R,S-homoserine-n-pentylamide

The product of example 52a (200 mg, 0.8 mmol) and n-pentylamine (232 μL, 2.0 mmol) were dissolved in 20 mL of 1:1 THF-acetonitrile and stirred at room temperature until starting material was consumed (tlc: R$_f$=0.15, 18:1 CHCl$_3$-EtOH). The volatiles were evaporated in vacuo. The residue was mixed with hexanes and the product filtered away to yield 273 mg, 0.79 mmol (99%). mp=181°-3° C. MS(CI) m/e 344(m+H)$^+$. $^1$H NMR (CDCl$_3$,300 MHz) δ 0.91(t,J=7 Hz,3H), 1.30-1.38(m,4H), 1.51-1.58(m, 2H), 1.95-2.04(m,1H), 2.12-2.21(m,1H), 3.25-3.36(m,2H), 3.80(bs, 2H), 4.26(bs,1H), 4.83-4.90(m,1H), 7.37(bt,J=3

Hz,1H), 7.64(dt, J=1,5 Hz,1H), 7.83(dt,J=1,6 Hz,1H), 7.93(d,J=6 Hz,1H), 8.10(d,J=6 Hz, 1H), 8.15(d,J=7 Hz,1H), 8.68(d,J=2 Hz,1H), 9.37(d,J=1Hz,1H). C,H,N analysis calculated for $C_{19}H_{25}N_3O_3$, 0.25 CHCl$_3$: C 61.13, H 6.82, N 11.26; found: C 60.82, H 6.88, N 11.16.

EXAMPLE 54

N-(3'-Quinolylcarbonyl)-R-methionine-di-n-pentylamide

Step 54a.
N-t-Butyloxycarbonyl-R-methionine-di-n-pentylamide

BOPCl (5.1 g, 20 mmol) was added to a cooled solution (4° C.) of N-t-Butyloxycarbonyl-R-methionine (5.0 g, 20 mmol), dipentylamine (8.0 mL, 40 mmol), in 60 mL of dry THF and the stirred reaction was allowed to attain room temperature overnight. The volatiles were evaporated in vacuo. The residue was dissolved in EtOAc and extracted successively with 1M $H_3PO_4$ (3×), 1M $Na_2CO_3$ (3×), brine (3×); then dried over MgSO$_4$, filtered and concentrated in vacuo to yield an oil: 4.6 g, 11.7 mmol (59%). R$_f$=0.81 (1:1 hexanes-EtOAc). $[α]_D$= +27.5° (c=2.7, MeOH). MS(CI) m/e 389(m+H)$^+$, 333, 311, 258, 219, 202, 158. $^1$H NMR(CDCl$_3$,300 MHz) δ 0.86–0.93(m,6H), 1.21–1.37(m,9H), 1.42(s, 9H), 1.43–1.66(m,3H), 1.76–1.96(m,2H), 2.11(s,3H), 2.54(t,J=7 Hz, 2H), 3.06–3.15(m,1H), 3.19–3.29(m,1H), 3.32–3.42(m,1H), 3.46–3.56(m,1H), 4.68–4.75(m,1H), 5.37(d,J=9 Hz,1H).

Step 54b. R-Methionine-di-n-pentylamide trifluoroacetate salt

The product of example 54a (4 g, 10.3 mmol) was dissolved in 30 mL TFA precooled to 4° C. After 2 hours, the excess reagent was evaporated and the residue was placed under high vacuum overnight. $[α]_D$=+5.1° (c=1.4, MeOH). MS(CI) m/e 289(m+H)$^+$. $^1$H NMR(DMSO$_{d6}$,300 MHz) δ 0.88(apparent q,J=8 Hz,6H), 1.18–1.35 (m,8H), 1.42–1.58(m,4H), 1.89–1.96(bm,2H), 2.08(s,3H), 2.43–2.67 (m,2H), 3.00–3.09(m,1H), 3.13–3.23(m,1H), 3.28–3.38(m,1H), 3.48–3.57(m,1H), 4.2–4.28(m,1H), 8.17(s,3H).

Step 54c,
N-(3'-Quinolylcarbonyl)-R-methionine-di-n-pentylamide

Quinoline-3-carboxylic acid (0.43 g, 2.5 mmol), the product of example 54b (1.0 g, 2.5 mmol), and TEA (697 μL, 5 mmol) were dissolved in 15 mL of CH$_2$Cl$_2$ cooled to 4° C. and EDCI (0.48 mg, 2.5 mmol) was added. The stirred reaction mixture was allowed to attain room temperature overnight. The volatiles were evaporated and the residue in EtOAc was extracted with 0.1M citric acid, 0.1M Na$_2$CO$_3$, water; then dried over MgSO$_4$, filtered and concentrated in vacuo. Silica gel chromatography of the residue eluted with a step gradient of CHCl$_3$ to 0.5% EtOH in CHCl$_3$ yielded an oil, 572 mg, 1.29 mmol (52%). R$_f$=0.19 (1:1 hexanes-EtOAc). $[α]_D$= +8.0° (c=0.85, MeOH). MS(CI) m/e 444(m+H)$^+$. $^1$H NMR(CDCl$_3$,300 MHz) δ 0.91(t,J=7 Hz, 3H), 0.93(t,J=7 Hz,3H), 1.23–1.42(m,8H), 1.52–1.62(m,2H), 1.63–1.75(m,2H), 2.02–2.17(m,5H), 2.56–2.72(m,2H), 3.10(t,J=8 Hz,0.5H), 3.14(t,J=8 Hz,0.5H), 3.25–3.35(m,1H), 3.46–3.55(m,1H), 3.59(t,J=8 Hz,0.5H), 3.63(t,J=8 Hz, 0.5H), 5.28–5.36(m,1H), 7.55(d,J=8 Hz, 1H), 7.12(dt,J=1,7 Hz,1H), 7.81(dt,J=1,8 Hz,1H), 7.88(dd,J=1,8 Hz,1H), 8.15(d,J=8 Hz,1H), 8.54(d, J=2 Hz,1H), 9.33(d,J=2 Hz,1H). C,H,N analysis calculated for $C_{25}H_{37}N_3O_2S$, 0.5 H$_2$O: C 66.33, H 8.46, N 9.28; found: C 66.33, H 8.19, N 9.25.

EXAMPLE 55

N-(3'-Quinolylcarbonyl)-R-methioninesulfoxide-di-n-pentylamide

The product of example 54c (100 mg, 0.23 mmol) was dissolved in 5 mL THF and m-chloroperbenzoic acid (47 mg, 0.23 mmol) was added at room temperature. The reaction was stirred overnight. The volatiles were evaporated and the residue, in EtOAc, was extracted with water until the aqueous extract was neutral (pH=7); then the solution was dried over MgSO$_4$, filtered and concentrated. The residue was purified by chromatography on silica gel eluted with CH$_2$Cl$_2$ and EtOH to provide the product as an oil. $[α]_D$=8.8° (c=0.73, MeOH). MS(CI) m/e 460(m+H)$^+$, 396. $^1$H NMR(CDCl$_3$,300 MHz) δ 0.92(apparent q,J=7 Hz,6H), 1.26–1.40(m,10H), 1.52–1.73(m,3H), 2.14–2.26(m,1H), 2.39–2.52(m,1H), 2.71–3.02(m,3H), 3.08–3.18(m,1H), 3.23–3.35(m,1H), 3.38–3.52(m, 1H), 3.58–3.68(m,1H), 5.20–5.34(m,1H), 7.62(tt,J=1,8 Hz,2H), 7.72 (d,J=7 Hz,1H), 7.83(tt,J=1,8 Hz,1H), 7.92(d,J=8 Hz,1H), 8.17(d,J=8 Hz, 1H), 8.62(dd,J=2,5 Hz,1H), 9.35(dd,J=2,3 Hz,1H). C,H,N analysis calculated for $C_{25}H_{37}N_3O_3S$,0.1 EtOAc: C 65.13, H 8.13, N 8.97; found: C 65.31, H 8.30, N 8.73.

EXAMPLE 56

N-(3'-Quinolylcarbonyl)-(O-methyl)-R,S-homoserine-di-pentylamide

The product of example 52b is methylated in a similar manner to that in example 22 to provide the title compound after purification by chromatography.

EXAMPLE 57

N-(3'-Quinolylcarbonyl)-(O-benzyl)-R,S-homoserine-di-n-pentylamide

The product of example 52b is benzylated in a manner similar to that in example 22 utilizing benzyl bromide as the alkylating agent. The title compound was provided after purification by chromatography.

EXAMPLE 58

N-(2'-Indolylcarbonyl )-R-Proline-di-n-pentylamide

Step 58a,
N-t-Butyloxycarbony-R-Proline-di-n-pentylamide

BOPCl (1.18 g, 4.64 mmol) was added to a cooled solution (4° C.) of N-t-Butyloxycarbonyl-R-Proline (1.0 g, 4.64 mmol), dipentylamine (2.5 mL, 12.5 mmol), in 50 mL of dry THF. The cooling bath was removed and the stirred reaction mixture was allowed to warm to ambient temperature gradually. After 5 hours, the volatiles were evaporated in vacuo. The residue was dissolved in EtOAc and extracted successively with 1M H$_3$PO$_4$ (3×), 1M Na$_2$CO$_3$ (3×), brine (3×); then dried over MgSO$_4$, filtered and concentrated in vacuo to yield an oil, 880 mg, 2.48 mmol (54%). R$_f$=0.28 (2:1 hexanes-EtOAc). $[α]_D$=+28.7° (c=1.0, MeOH). MS(CI) m/e 355m+H)$^+$, 299, 255. $^1$H NMR(CDCl$_3$,300 MHz) δ 0.84–0.94(m,6H), 1.23–1.38(m,8H), 1.41(s.,6H), 1.45(s,3H), 1.49–1.58(m,6H), 1.80–1.90(m,1H), 2.0–2.23(m,1H), 3.12–3.33(m,4H), 3.4–3.52(m,1H), 3.56–3.67(m,1H), 4.44(dd,J=4,8 Hz,0.6H), 4.58(dd,J=2,8 Hz,0.4H).

Step 58b, R-Proline-di-n-pentylamide hydrochloride

The product of example 58a (800 mg, 2.3 mmol) was mixed with HCl-Dioxane (12.5 mL, 50 mmol, precooled to 4° C.) under an $N_2$ atmosphere at ambient temperature. After 1 hour, the volatiles were evaporated in vacuo and the residue was mixed with toluene and concentrated (twice) then placed under high vacuum overnight. The residue was utilized directly.

Step 58c.
N-(2'-Indolylcarbonyl)-R-Proline-di-n-pentylamide

EDCI (440 mg, 2.3 mmol) was added to a cooled (4° C.) solution of indole-2-carboxylic acid (371 mg, 2.3 mmol), the product of example 58b (2.3 mmol assumed), HOBt (311 mg, 2.3 mmol), and TEA (321 µL, 2.3 mmol) in 10 mL $CH_2Cl_2$. The stirred reaction was allowed to attain ambient temperature overnight. The volatiles were evaporated and the residue was dissolved in EtOAc and extracted with 1 M $H_3PO_4$ (3×), 1M $Na_2CO_3$ (3×), brine (3×); then dried over $MgSO_4$, filtered and concentrated to an orange oil. The crude product was purified by chromatography on silica eluted with 2:1 hexanes-EtOAc to yield 0.92 g, 2.4 mmol (92%) as a slightly yellow glass. $R_f$=0.22 (2:1 hexanes-EtOAc). The glass was dissolved in hot hexanes-EtOAc, then cooled slowly to −20° C. An oil separated out and over 24 hours solidified. The solution was decanted and the solid was collected using hexanes to yield 769 mg (84%). mp=63°–7° C. $[\alpha]_D$=−20.4° (c=1.0, MeOH). MS(CI) m/e 398(m+H)+, 241, 213. $^1$H NMR(CDCl$_3$,300 MHz) δ 0.88(t, J=7 Hz,3H), 0.93(t,J=6 Hz,3H), 1.24–1.43(m,8H), 1.51–1.75(m,3H), 1.80–1.90(m,1H), 1.94–2.28(m,3H), 2.32–2.45(m,1H), 3.16–3.37(m, 2H), 3.43–3.54(m,2H), 4.0–4.08(m,1H), 4,12–4.2(m,1H), 5.02(dd, J=4,8 Hz,1H), 6.96(bs,1H), 7.12(dt,J=1,8 Hz,1H), 7.28(dt,J=1,7 Hz,1H), 7.48(dd,J=1,8 Hz,1H), 7.67(d,J=8 Hz,1H), 9.30(s,1H) C,H,N analysis calculated for $C_{24}H_{35}N_3O_2$: C 72.50, H 8.87, N 10.57; found: C 72.55, H 8.91, N 10.49.

EXAMPLE 59

N-(3'-Quinolylcarbonyl)-R-lysine-di-n-pentylamide hydrobromide

The product of example 35c (1.61 g, 2.64 mmol) was treated with 15 mL of HBr in HOAc (1.1 N, 16.5 mmol) for 2 hours under an inert atmosphere. The solvent was evaporated and the residue was purified by chromatography on silica gel eluted with a $CH_2Cl_2$ to 1% EtOH in $CH_2Cl_2$ step gradient to yield 1.25 g, 2.39 mmol (91%) as a yellow glass. mp=85°–95° C. $^1$H NMR(DMSO$_{d6}$,300 MHz) δ 0.85(t,J=7 Hz,6H), 1.23–1.83(m,18H), 2.78(t,J=7 Hz,2H), 3.06–3.17(m,1H), 3.28–3.44(m,3H), 4.86–4.93(m,1H), 7.57(bs,2H), 7.72(dt,J=1,7 Hz,1H), 7.88(dt,J=1,7 Hz,1H), 8.10(d,J=8 Hz,2H), 8.92(d, J=2 Hz,1H), 9.02(d,J=8 Hz,1H), 9.32(d,J=2 Hz,1H).

EXAMPLE 60

$N^\alpha$-(3'-Quinolylcarbonyl)-$N^\epsilon$-phenylthiolcarbonyl-R-lysine dipentylamide The product of example 59 (20 mg, 0.045 mmol) was treated with carbonyldiimidazole (8.1 mg, 0.05 mmol) in 10 mL $CH_2Cl_2$ at room temperature overnight. Thiophenol (10.3 µL, 0.10 mmol)and 10 mL THF were added and the mixture was heated to 60° C. After 1 day, the reaction was eluted on silica gel with 1% EtOH in $CH_2Cl_2$ to yield an oil. MS(CI) m/e 577(m+H)+, 467, 420. $^1$H NMR(CDCl$_3$,300 MHz) δ 0.88–0.96(m,6H), 1.23–1.86(m,18H), 3.12 (dt,J=7,13 Hz,1H), 3.22–3.44(m,4H), 3.59(dt,J=7,13 Hz,1H), 5.0–5.17 (m,1H), 5.70(t,J=5 Hz, 1H), 7.32–7.37(m,3H), 7.47–7.51(m,3H), 7.62 (dt,J=1,8 Hz,1H), 7.82(dt,J=1,7 Hz,1H), 7.91(dd,J=1,8 Hz,1H), 8.16(d, J=8 Hz,1H), 8.63(d,J=2 Hz,1H), 9.37(s,J=2 Hz,1H).

EXAMPLE 61

N-(3'-Quinolylcarbonyl)-R-phenylglycine-(2'-propylpiperidinyl)amide

Step 61a.
N-Benzyloxycarbonyl-R-Phenylglycine-(2'-propylpiperidinyl)amide

N-Benzyloxycarbonyl-R-phenylglycine (1.0 g, 3.5 mmol), 2-propylpiperidine (1 mL, 6.64 mmol), HOBt (475 mg, 3.5 mmol) and TEA (490 µL, 3.5 mmol) were dissolved in 25 mL of $CH_2Cl_2$ and treated with BOPCl (890 mg, 3.5 mmol). Additional TEA (490 µL) and BOPCl(890 mg) were added after 2 days. After 6 days, the solvent was evaporated and the crude reaction was purified by chromatography on silica gel eluted with a 9:1 to 4:1 hexane-EtOAc step gradient to yield 179 mg, 0.454 mmol (13%). mp=100°–115° C. $[\alpha]_D$=−13.5° (c=1.0, MeOH). MS(CI) m/e 395(m+H)+, 261. $^1$H NMR(CDCl$_3$,300 MHz) δ 0.52(t,J=7 Hz,1H), 0.92(t,J=7 Hz,2H), 1.18–1.70(m,10H), 2.56–2.67(m,0.33H), 3.01(dd,J=2,13 Hz,0.67H), 3.57(bd,J=12 Hz,0.67H), 3.80(bs,0.33H), 4.51(bd,J=13 Hz,0.33H), 4.78(bs,0.67H), 4.98(d,J=1 1 Hz,1H), 5.12(d,J=1 1 Hz,1H), 5.54(d, J=7 Hz,0.67H), 5.58(d,J=7 Hz,0.33H), 6.46–6.55(m,1H), 7.28-7.43 (m,10H).

Step 61 b. R-Phenylglycine-(2'-propylpiperidinyl)amide

The product of example 61a (150 mg, 0.38 mmol) was treated with 25 mg of 10% Pd on carbon in 5 mL of MeOH under one atmosphere of hydrogen for 24 hours. The catalyst was filtered away and the filtrate was evaporated to yield product.

Step 61c.
N-(3'-Quinolylcarbonyl)-R-phenylglycine-(2'-propylpiperidinyl)amide

Quinoline-3-carboxylic acid (38.1 mg, 0.22 mmol), the product of example 61b (31 mg, 0.22 mmol) and TEA (31 µL, 0.22 mmol) were dissolved in 4 mL of 1:1 DMF-$CH_2Cl_2$ and treated with EDCI (42.1 mg, 0.22 mmol) with stirring at room temperature overnight. The solvent was evaporated and the residue was extracted as in example 39a. $R_f$=0.4 (1:1 hexane-EtOAc). MS(CI) m/e 416(m+H)+, 261, 154, 128. $^1$H NMR(CDCl$_3$,300 MHz) a 0.55(t, J=7 Hz,1H), 0.94(t,J=7 Hz,2H), 1.23–1.72(m,10H), 2.71(dt,J=2,13 Hz, 0.33H), 3.08(dt,J=2,13 Hz,0.67H), 3.68(bd,J=13 Hz, 0.67H), 3.93(bs, 0.33H), 4.58(bd,J=13 Hz,0.33H), 4.85(bs,0.67H), 6.03(d,J=7 Hz, 0.67H), 6.07(d,J=7 Hz,0.33H), 7.3–7.42(m,3H), 7.52–7.63(m,3H), 7.80(dt,J=1,7 Hz,1H), 7.90(d,J=8 Hz,1H), 8.14(d,J=8 Hz,1H), 8.28(t, J=6 Hz,1H), 8.59(d,J=2 Hz,1H), 9.34(d,J=2 Hz,1H). C,H,N analysis calculated for $C_{26}H_{29}N_3O_2$,0.5 $H_2O$: C 73.56, H 7.12, N 9.90; found: C 73.60, H 7.10, N 9.61.

EXAMPLE. 62

N-(4',8 '-Dihydroxy-2'-quinolylcarbonyl)-R-phenylglycine-(2'-propylpiperidinyl)amide 4,8-Dihydroxyquinoline-2-carboxylic acid (45 mg, 0.22 mmol), the product of example 61b (52 mg, 0.20 mmol) and TEA (31 μL, 0.22 mmol) were dissolved in 4 mL of 1:1 DMF-$CH_2Cl_2$ and treated with EDCI (42 mg, 0.22 mmol) with stirring overnight. The reaction was then poured into EtOAc and extracted as in example 39a. The resulting residue was purified by chromatography on silica gel eluted with a 1% to 9% EtOH in $CH_2Cl_2$ step gradient. MS(CI) m/e 448(m+H)+, 293. $^1$H NMR (DMSO$_{d6}$,300 MHz) δ 0.71(t,J=7 Hz,1H), 0.81-0.90(m,2H), 1.15-1.70(m,10H), 3.07(bt,J=13 Hz,0.67H), 3.33(s,$H_2O$), 3.68(bd, J=12 Hz,0.67H), 4.02(bs,0.33H), 4.36(d,J=8 Hz,0.33H), 4.68(bs, 0.67H), 6.12-6.17(m,1H), 7.09(d,J=7 Hz,1H), 7.32-7.56(m,8H), 9.84(d,J=8 Hz,0.67H), 10.08(d,J=8 Hz,0.33H), 10.23(s,0.67H), 10.24(s,0.33H), 11.73(bs,1H).

EXAMPLE 63

N-(3'-Quinolylcarbonyl)-R-phenylglycine(N-benzyl,N-2'-cyanoethyl)amide

Step 63a.

$N^\alpha$-Benzyloxycarbonyl-R-phenylglycine-(N-benzyl,-N-2'-cyanoethyl)amide

N-Benzyloxycarbonyl-R-phenylglycine (285 mg, 1.0 mmol), 3-(benzylamino)propionitrile (391 μL, 2.5 mmol) and TEA (139 μL, 1.0 mmol) were dissolved in 10 mL of $CH_2Cl_2$ and treated with BOPCl (256 mg, 1.0 mmol). After 1 day, another 139 μL of TEA was added. After 2 days, additional BOPCl (256 mg), amine (391 μL) and DMF (5 mL) were added. After 3 days, the solvents were evaporated and the residue was extracted as in example 39a. The crude residue was recrystallized from hexanes-EtOAc to yield 314 mg, 0.74 mmol (74%). R$_f$=0.75 (1:1 hexanes-EtOAc). mp=114°-150° C. [α]$_D$=-9.4° (c=0.67, 1:1 DMF-MeOH). MS(CI) m/e 428(m+H)+, 445, 384, 375. $^1$H NMR(CDCl$_3$,300 MHz) δ 2.45-2.66 (m,2H), 3.33-3.42(m,1H), 3.46-3.52(m,0.5H), 3.66-3.75(m,1H), 4.38(d,J=16 Hz,1H), 4.43-4.5(m,0.5H), 4.63(d,J=16 Hz,1H), 4.69(s, 0.5H), 5.01-5.2(m,3H), 5.59(d,J=7 Hz,0.5H), 5.66(d,J=7 Hz,1H), 6.88 (s,0.5H), 6.18-6.27(m,1.5H), 6.82(bs,0.5H), 6.95(t,J=4 Hz,2H), 7.10-7.18(m,2H), 7.28-7.39(m,15H). C,H,N calculated for $C_{26}H_{25}N_3O_3$, 0.1 $H_2O$: C 72.74, H 5.92, N 9.79; found: C 72.79, H 5.99, N 9.40.

Step 63b.

R-Phenylglycine-(N-benzyl-N-2'-cyanoethyl)amide

The product of example 63a (225 mg, 0.53 mmol) was dissolved in 25 mL of EtOH and treated with 100 mg of 10% Pd/C at room temperature. After 1.5 hours, the catalyst was filtered and the filtrate was evaporated to yield 158 mg, 0.54 mmol(quantitative). MS(CI) m/e 294(m+H)+, 241.

Step 63.c,

N-(3'-Quinolylcarbonyl)-R-phenylglycine(N-benzyl,N-2'-cyanoethyl)amide

Quinoline-3-carboxylic acid (35 mg, 0.20 mmol) and the product of example 63b (53 mg, 0.18 mmol) were dissolved in 10 mL of $CH_2Cl_2$ and treated with EDCI (38 mg, 0.20 mmol). After 1 day, the solvent was evaporated and the residue was extracted as in example 39a to give 54 mg, 0.12 mmol (67%). [α9 $_D$=-0.42° (c=2.6, CHCl$_3$). mp=57°-63° C. MS(CI)m/e 449(m+H)+. $^1$H NMR (CDCl$_3$,300 MHz) δ 1.90-2.02(m,0.25H), 2.27-2.38(m,0.25H), 2.49-2.72(m,1.5H), 3.42(dt,J=7,13 Hz,1H), 3.81(dt,J=7,13 Hz,1H), 4.46(d, J=16 Hz,1H), 4.73(d,J=16 Hz,1H), 6.11(d,J=6 Hz,0.25H), 6.16(d,J=7 Hz, 0.75H), 6.98-7.02(m,2H), 7.19-7.22(m,0.5H), 7.30-7.33(m,2.5H), 7.38-7.46(m,3H), 7.53-7.64(m,3H), 7.82(dt,J=1,7H,1H), 7.85-7.94 (m,2H), 8.15(d,1H, J=8 Hz), 8.61(d,J=1Hz,1H), 9.33(d,J=1Hz,1H). C,H,N analysis calculated for $C_{28}H_{24}N_4O_2$, 0.7 $H_2O$: C 72.93, H 5.55, N 12.15; found: C 72.86, H 5.58, N 11.77.

EXAMPLE 64

N-(4',8'-Dihydroxy-2'-quinolylcarbonyl)-R-phenylglycine (N-benzyl,N-2'-cyanoethyl)amide 4,8-Dihydroxyquinoline-2-carboxylic acid (41 mg, 0.20 mmol), the product of example 65b (53 mg, 0.18 mmol), and TEA (28 μL, 0.20 mmol) were dissolved in 5 mL of DMF and treated with EDCI (38 mg, 0.20 mmol). Additional TEA (28 μL) and EDCI (38 mg) were added after 2 hours and 1 day. After 2 days HOBt (27 mg, 0.20 mmol) was added to the reaction mixture. After 3 days, the solvent was evaporated and the residue was extracted with 0.1 M citric acid, and water and the organic solution was dried over MgSO$_4$ then filtered and concentrated. The crude product was purified by silica get chromatography eluted with 1:1 hexanes-EtOAc to provide 22.6 mg, 0.05 mmol (26%). R$_f$=0.4 (1:1 hexane-EtOAc). mp=218°-222° C. [α]$_D$=-4.8° (c=0.42, MeOH). MS(CI) m/e 481(m+H)+, 428. $^1$H NMR(CD$_3$OD,300 MHz) δ 2.47-2.58(m,0.33H), 2.6-2.82(m,2H), 3.33-3.62(m,2.33H), 3.68-3.78(m,0.33H), 3.82-3.91(m,1H), 4.53(d,J=16 Hz,1H), 4.62(d, J=14 Hz,0.33H), 4.76(d, J=16 Hz,1H), 4.87(s,$H_2O$), 4.92(d,J=5 Hz, 0.33H), 6.18(s,1H), 7.10(dd, J=1,7 Hz,1H), 7.2-7.35(m,7H), 7.39-7.46(m,3H), 7.51-7.60(m,2H), 7.67(dd,J=1,8 Hz,1H).

EXAMPLE b 65

N-(3'-Quinolylcarbonyl)-R-tyrosine-di-n-pentylamide hydrochloride

The product of example 44 (1.5 g, 3.0 mmol) was treated with 1.4 N HCl in dioxane (11 mL, 15 mmol) for 10 minutes. The excess reagent was evaporated and the oily residue was triturated with diethylether and filtered to yield 1.3 g, 2.6 mmol (87%) of a pale yellow solid. MS(CI) m/e 476(m+H)+, 458. $^1$H NMR(DMSO$_{d6}$, 300 MHz) δ 0.84(t,J=7 Hz,6H), 1.15-1.62(m,12H), 2.87-3.22(m,3H), 3.29-3.40(m,3H), 5.02(apparent q,J=7 Hz,1H), 6.66(d,J=8 Hz,2H), 7.11(d,J=8 Hz,2H), 7.78(dt,J=1,8 Hz,1H), 7.96(dt,J=1,8 Hz,1H), 8.17(t,J=7 Hz,2H), 9.04(d,J=2 Hz,1H), 9.22(d,J=8 Hz,1H), 9.33(d, J=2 Hz,1H). C,H,N analysis calculated for $C_{29}H_{37}N_3O_3$, 1.3 HCl: C 66.60, H 7.38, N 8.03; found: C 66.43, H 7.38, N 7.99.

EXAMPLE 66

N-(3'-Quinolylcarbonyl)-R-histidine-di-n-pentylamide dihydrochloride

The product of example 29 (800mg, 1.78 mmol) was dissolved in 13 mL of 1.4 N HCl in acetic acid for 10 min and then the volatiles were evaporated to remove excess reagent. The oily residue was dissolved in a small amount of $CH_2Cl_2$ and the product was precipitated with hexanes. The solid was collected to yield 824 mg, 1.58 mmol (89%). MS(CI) m/e 450(m+H)+. $^1$H NMR(DMSO$_{d6}$,300 MHz) δ 0.74(t,J=7 Hz,3H), 0.85(t,J=7 Hz,3H), 1.12-1.32(m,8H), 1.41-1.52(m,4H), 3.08-3.43(m,6H), 5.24-5.31(m,1H), 7.45(s,1H), 7.77(dt,J=1,7 Hz,1H), 7.94(dt,J=1,7 Hz,1H), 8.15(dt,J=1,9 Hz,2H), 9.02(s,2H), 9.31-9.33(m,2H), 14.18(s,1H), 14.57(s,1H). C,H,N analysis calculated for $C_{26}H_{35}N_5O_2$, 2.6 HCl: C 57.36, H 6.96, N 12.87; found: C 57.30, H 6.96, N 12.86.

EXAMPLE 67

N-(4',8'-Dihydroxy-2'-quinolylcarbonyl)-R-(4'-hydroxyphenyl)-glycine-di-n-pentylamide The reaction was performed in a similar manner to that in example 5 utilizing 0.3 g of the compound of example 32b, 4',8'-dihydroxyquinoline-2-carboxylic acid (0.2 g), EDCI (0.21 g), HOBt (0.13 g) and NMM (0.22 mL). The product was isolated in 75% yield (0.37 g). MS(CI) m/e 494(m+H)+. $^1$H NMR(DMSO$_{d6}$,300 MHz) δ 0.85(m,6H), 1.1-1.35(m,10H), 1.38-1.45(m,4H), 3.0-3.5(m,4H), 5.95(d,J=9 Hz,1H), 6.76(d,J=9 Hz,2H), 7.08(d,J=9 Hz,1H), 7.23(d, J=9 Hz,2H), 7.4(t,J=9 Hz,1H), 7.55(m,2H), 9.5(bs,1H), 9.75(d,J=10 Hz, 1H). C,H,N calculated for $C_{28}H_{35}N_3O_5$, 0.5 $H_2O$: C 66.91, H 7.22, N 8.36; found: C 66.76, H 7.20, N 8.18.

EXAMPLE 68

N-(2'-Indolylcarbonyl)-glycine-di-n-pentylamide

Step 68a. N-Benzyloxycarbonyl-glycine-di-n-pentylamide

The compound was prepared in a manner similar to that in example 1a utilizing N-t-butyloxycarbonylglycine. MS(CI) m/e 349(m+1)+, 305, 241, 215, 184. $^1$H NMR(CDCl$_3$,300 MHz) δ 7.30-740(m,5H), 5.86(bs,1H), 5.12(bs,2H), 4.0(bd,J=4.5 Hz,2H), 3.32(t, J=7.5 Hz,2H), 3.15(t,J=7.5 Hz,2H), 1.50-1.70(m,4H), 1.20-1.40(m, 8H), 0.9(m,6H).

Step 68b. N-(2'-Indolylcarbonyl)-glycine-di-n-pentylamide

The product of example 68a was deprotected in a manner similar to that in example 44. The free amine product was then coupled with indole-2-carboxylic acid as in example 2. mp=98°-100° C. MS(EI) m/e 357(m)+, 287, 184. $^1$H NMR(CDCl$_3$,300 MHz) δ 9.27(s,1H), 7.67(d,J=6 Hz,1H), 7.45(bd,J=7 Hz,2H), 7.29(dt,J=1,6 Hz, 1H), 7.14(dt,J=1,6 Hz,1H), 6.98(s,1H), 4.27(d,J=4 Hz,2H), 3.39(bt, J=7 Hz,2H), 3.25(bt,J=7 Hz,2H), 1.55-1.70(m,4H), 1.25-1.40(m,8H), 0.93(t,J=6 Hz,3H), 0.91(t,J=6 Hz,3H). C,H,N analysis calculated for $C_{21}H_{31}N_3O_2$, 0.3 $H_2O$: C 69.51, H 8.78, N 11.58; found: C 69.45, H 8.58, N 11.47.

EXAMPLE 69

Ethyl N-(3'-quinolylcarbonyl)glycinyl-(N-benzyl)glycinate

Step 69a. Ethyl N-(t-Butyloxycarbony)glycinyl-(N-benzyl) glycinate

N-t-Butyloxycarbonylglycine and ethyl N-benzylglycinate were coupled in a manner similar to that in example 1a to provide product.

Step 69b. Ethyl N-(3'quinolylcarbonyl)glycinyl-(N-benzyl)glycinate

The product of example 69a was deprotected in a manner similar to that in example 1b and then coupled in a manner similar to that in example 1c to provide product. MS(CI) m/e 406(m+H)+, 334, 194. $^1$H NMR(CDCl$_3$,300 MHz) δ 9.37(d,J=2 Hz,0.33H), 9.35(d, J=2 Hz, 0.67H), 8.65(bm,1H), 8.18(bd,J=7 Hz,1H), 7.94(m,1H), 7.83 (m,1H), 7.63(m,1H), 7.43-7.55(m,1H), 7.30-7.40(m,3H), 7.25(m, 2H), 4.73(s,0.67H), 4.67(s,1.33H), 4.51(d,J=4 Hz, 1.33H), 4.33(d, J=4 Hz,0.33H), 4.16-4.25(m,2H), 4.13(s,1.33H), 4.00(s,0.67H), 1.28(m,3H).

EXAMPLE 70

N-(3'-Quinolylcarbonyl)-R-homophenylalanine-di-n-pentylamide

Step 70a. N-(t-Butyloxycarbonyl)-R-homophenylalanine-di-n-pentyamide

The product was prepared in an analogous manner to that in example 1a using t-Butyloxycarbonyl-R-homophenylalanine. MS(CI) m/e 419(m+H)+, 363, 345, 319. $^1$H NMR(CDCl$_3$,300 MHz) δ 7.85(m,1H), 7.48(m,1H), 7.18-7.32(m,5H), 5.39(bd,J=9 Hz,1H), 4.56 (m,1H), 3.48(dt,J=7,14 Hz,1H), 3.39(t,J=7 Hz,1H), 3.08(m,2H), 2.68 (m,2H), 1.88(m,2H), 1.45(s,9H), 1.20-1.35(m,8H), 1.13(m,2H), 0.88(m,6H).

Step 70b. N-(3'-Quinolylcarbonyl)-R-homophenylalanine-di-n-pentylamide

The product was prepared in analogous manner to those in examples 2 and 3 utilizing the product of example 70a as the starting material. MS(CI) m/e 474(m+H)+, 369, 319, 305, 289. $^1$H NMR(CDCl$_3$,300 MHz) δ 9.32(d,J=2 Hz,1H), 8.53(d,J=2 Hz,1H), 8.16(bd,J=8 Hz,1H), 7.90(dd,J=1,8 Hz,1H), 7.82(m,1H), 7.62(m,1H), 7.40(bd,J=8 Hz,1H), 7.30(m,4H), 7.20(m,1H), 5.19(m,1H), 3.55-3.70(m,1H), 3.05-3.20(m,3H), 2.78(bt,J=7.5 Hz,2H), 2.15(m,2H), 1.50-1.65(m,4H), 1.15-1.35(m,8H), 0.90(m,6H).

EXAMPLE 71

N-(3'-Quinolylcarbonyl)glycine-di-n-pentylamide

Step 71a. N-(3'-Quinolylcarbonyl)glycine

Quinoline-3-carboxylic acid and methyl glycinate hydrochloride were coupled in a manner similar to that in example 1c. The resulting product was subjected to saponification in MeOH with 1N NaOH. The desired product was extracted with EtOAc from the acidified solution or alternatively allowed to slowly precipitate from the acidified solution. MS(CI) m/e 231(m+H)+, 187. $^1$H NMR(DMSO$_{d6}$,300 MHz) δ 12.72(bs,1H), 9.32(d,J=4 Hz,1H), 9.11(t, J=6 Hz,1H), 8.87(d,J=3 Hz,1H), 8.12(t,J=7 Hz,2H), 7.89(t,J=7 Hz,1H), 7.71(t,J=7 Hz,1H), 4.03(bs,2H).

Step 71b. N-(3'-Quinolylcarbonyl)glycine-di-n-pentylamide

The product of example 71a and di-n-pentylamine were coupled in a manner similar to that in example 1a. The product was isolated by chromatography and solidifies upon concentration. mp=36°-37° C. MS(CI) m/e 370(m+H)+. $^1$H NMR(CDCl$_3$,300 MHz) δ 9.38(d,J=2

Hz,1H), 8.65(d,J=1.8 Hz,1H), 8.18(d,J=8.5 Hz,1H), 7.93(dd, J=1,8 Hz,1H), 7.83(m,1H), 7.64(m,2H), 4.32(d,J=3.7 Hz,2H), 3.41(bt, J=8 Hz,2H), 3.27(bt,J=8 Hz,2H), 1.62(m,4H), 1.30–1.45 (m,8H), 0.95 (t,J=7 Hz,3H), 0.92(t,J=7 Hz,3H). C,H,N analysis calculated: $C_{32}H_{31}N_3O_2$: C 71.49, H 8.46, N 11.37; found: C 71.28, H 8.42, N 11.36.

EXAMPLE 72

N-(3'-Quinolylcarbonyl)glycine-(4-propyl)piperidinylamide

The acid from example 71a and 4-propylpiperdine were coupled as in example 1a. mp=116°–117° C. MS(CI) m/e 340(m+H)+, 279, 254, 201. $^1$H NMR(CDCl$_3$,300 MHz) δ 9.36(d,J=2 Hz,1H), 8.63(d, J=2 Hz,1H, 8.16(d,J=8.5 Hz,1H), 7.93(dd,J=1,8 Hz,1H), 7.82(m,1H), 7.60(bs,1H), 7.63(m,1H), 4.61(dt,J=2,13 Hz,1H), 4.31(m,2H), 3.79(bd,J=10 Hz,1H), 3.07(dt,J=3,13 Hz,1H), 2.70(dt,J=3,13 Hz,1H), 1.81(bm,2H), 1.55(m, 1H), 1.05–1.40(m,6H), 0.92(t,J=7 Hz,3H). C,H,N analysis calculated for $C_{20}H_{25}N_3O_2$, 0.1 $H_2O$: C 70.40, H 7.44, N 12.31; found: C 70.19, H 7.44, N 12.15.

EXAMPLE 73

N-(3'Quinolylcarbonyl)-R-phenylglycine-di-n-pentylamide

Step 73a.
N-Benzyloxycarbonyl-R-phenylglycine-di-n-pentylamide

The product was obtained from the coupling of N-Benzyloxycarbonyl-R-phenylglycine and di-n-pentylamine as in example 1a. MS(CI) m/e 425(m+H)+, 333, 317, 291. $^1$H NMR(CDCl$_3$, 300 MHz) δ 7.27–7.45(m,10H), 6.48(bd,J=7.5 Hz,1H), 5.53(d,J=7.5 Hz, 1H), 5.12(d,J=12 Hz,1H), 5.01(d,J=12 Hz,1H), 3.48(m,1H), 3.18(m, 2H), 2.97(m,1H), 1.50(m,4H), 1.10–1.35(m,8H), 0.87(t,J=7.5 Hz,3H), 0.84(t,J=7.5 Hz,3H).

Step 73b, R-Phenylglycine-di-n-pentylamide

The product resulted from the hydrogenolysis of the product of example 73a. MS(CI) m/e 291(m+H)+, 158. $^1$H NMR(CDCl$_3$, 300 MHz) δ 7.25–7.40(m,5H), 4.65(bs,1H), 3.52(m,1H), 3.08–3.22(m,2H), 2.92(m,1H), 2.02(bs,2H), 1.50(m,3H), 1.10–1.35 (m,9H), 0.88(t,J=7 Hz,3H), 0.85(t,J=7 Hz,3H).

Step 73c.
N-(3'Quinolylcarbonyl)-R-phenylglycine-di-n-pentylamide

The product of example 73b was coupled in a similar manner to that in example 1c to provide product. MS(CI) m/e 446(m+H)+. $^1$H NMR(CDCl$_3$,300 MHz) δ 9.33(d,J=2 Hz,1H), 8.58(d,J=2 Hz,1H), 8.13(bt,J=8 Hz,2H), 7.88(bd,J=8 Hz,1H), 7.79(m,1H), 7.62(m,1H), 7.55(m,2H), 7.32–7.42(m,3H), 6.03(d,J=6 Hz,1H), 3.55(m,3H), 1.15–1.40(m,9H), 0.90(t,J=7 Hz,3H), 0.86(t,J=7 Hz,3H).

EXAMPLE 74

N-(4',8'-Dihydroxy-2'-quinolylcarbonyl)-R-Phenylglycine-di-n-pentylamide

The product of example 73b was coupled in a similar manner to that in example 5 to provide the title compound. mp=89°–91° C. MS(CI) m/e 478(m+H)+, 293, 190, 177. $^1$H NMR(DMSO$_{d6}$, 300 MHz) δ 9.91(bd,J=8 Hz,1H), 7.55(m,2H), 7.35–7.45(m,7H), 7.08(dd,J=1,7.5 Hz,1H), 6.11 (bd,J=8 Hz,1H), 3.05–3.30(m,4H), 1.60(m,1H), 1.48(m,2H), 1.13–1.35(m,9H), 0.85(t,J=7 Hz,3H), 0.78(t,J=7 Hz,3H). C,H,N analysis calculated for $C_{28}H_{35}N_3O_4$, 0.3 $H_2O$: C 69.63, H 7.43, N 8.70; found: C 69.61, H 7.40, N 8.65.

EXAMPLE 75

N-(3'-Chlorophenylaminocarbonyl)-R-phenylglycine-di-n-pentylamide

The product of example 73b was reacted with 3-chlorophenylisocyanate to provide the title compound. MS(CI) m/e 444(m+H)+, 425, 317, 291, 259, 242. $^1$H NMR(CDCl$_3$,300 MHz) δ 7.95(bs,1H), 7.42(m,1H), 7.22–7.34(m,5H), 7.13(d,J=7.5 Hz,1H), 7.08(m,2H), 6.89(m,1H), 5.92(d,J=8 Hz,1H), 3.50(m,1H), 3.00–3.30 (m,4H), 1.43–1.63(m,3H), 1.10–1.30(m,8H), 0.84(t,J=7 Hz,3H), 0.78 (t,J=7 Hz,3H).

EXAMPLE 76

N-(3'-Methylphenylaminocarbonyl)-R-phenylglycine-di-n-pentylamide

The product of example 73b was reacted with 3-methylphenylisocyanate to provide the title compound. MS(CI) m/e 424 (m+H)+, 374, 317, 291, 276, 239, 228. $^1$H NMR(CDCl$_3$, 300 MHz) δ 7.27–7.48(m,5H), 7.18(m,1H), 7.12(d,J=8 Hz,1H), 7.06(m,2H), 6.82 (bd,J=8 Hz,1H), 6.77(bd,J=8 Hz,1H), 5.87(d,J=8 Hz, 1H), 3.51(m,1H), 3.20(m,2H), 3.04(m,1H), 2.28(s,3H), 1.50(bm,4H), 1.10–1.30(m, 8H), 0.84(t,J=7 Hz,3H), 0.82(t,J=7 Hz,3H).

EXAMPLE 77

N-(5'-Fluoroindolylcarbonyl)-R-phenylglycine-di-n-pentylamide

The product of example 73b was reacted with 5-fluoroindole-2-carboxylic acid in a manner similar to that in example 2 to provide product. mp=94°-6° C. MS(CI) m/e 452 (m+H)+, 276, 267, 184. $^1$H NMR(CDCl$_3$,300 MHz) δ 9.36(bs,1H), 7.96(d,J=7 Hz,1H), 7.50(m,2H), 7.30–7.40(m,3H), 7.36(s,1H), 7.33 (m,1H), 6.98(dt, J=2.5,9 Hz,1H), 6.91(m,1H), 5.94(d,J=7 Hz,1H), 3.53 (m,1H), 3.13–3.30(m,2H), 3.04(m,1H), 1.45–1.65(m,4H), 1.10–1.40 (m,8H), 0.89 (t,J=7 Hz,3H), 0.85(t,J=7 Hz,3H). C,H,N analysis calculated: $C_{27}H_{34}FN_3O_2$: C 71.81, H 7.59, N 9.31; found: C 71.53, H 7.50, N 9.30.

EXAMPLE 78

N-(5'-Chloroindolylcarbonyl)-R-phenylglycine-di-n-pentylamide

The product of example 73b was reacted with 5-chloroindole-2-carboxylic acid in a manner similar to that in example 2 to provide the title compound. MS(CI) m/e 468(m+H)+, 434, 302, 276, 212. $^1$H NMR(CDCl$_3$,300 MHz) δ9.36(bs,1H), 7.97(d,J=7 Hz, 1H), 7.59(m,1H), 7.50(m,2H), 7.35(m,3H), 7.22(m,2H), 6.89(m,1H), 5.94(d,J=7 Hz,1H), 3.53(m,1H), 3.15–3.30(m,2H), 3.04(m,1H), 1.45–1.60(m,4H), 1.10–1.40(m,8H), 0,89(t,J=7 Hz,3H), 0.85(t,J=7 Hz,3H). C,H,N analysis calculated for $C_{27}H_{34}ClN_3O_2$: C 69.29, H 7.32, N 8.98; found: C 69.44, H 7.36, N 8.95.

EXAMPLE 79

N-(2'-Quinolylcarbonyl)-R-Phenylglycine-di-n-pentylamide

The product of example 73b was coupled in a similar manner to that in example 3 to provide the desired compound. mp=116°–7° C. MS(CI) m/e 446(m+H)+, 289, 277, 261, 246. $^1$H NMR(CDCl$_3$, 300 MHz) δ 9.62(d,J=8 Hz,1H), 8.24(bs,2H), 8.17(d,J=8 Hz,1H), 7.83(d,J=8 Hz,1H), 7.74(m,1H), 7.59(m,3H), 7.30–7.40(m,3H), 6.06(d,J=8 Hz,1H), 3.61(m,1H), 3.32(m,1H), 3.0–3.20(m,2H), 1.50–1.65(m,4H), 1.15–1.40(m,8H), 0.89(t,J=7 Hz,3H), 0.87(t,J=7 Hz,3H). C,H,N analysis calculated for C$_{28}$H$_{35}$N$_3$O$_2$: C 75.47, H 7.92, N 9.43; found: C 75.45, H 7.91, N 9.43.

EXAMPLE 80

N'-(3'-Quinolylcarbonyl)-1-amino-cyclohexane-(N-pentyl) carboxamide

Step 80a. N'-(t-Butyloxycarbonyl)-1-amino-cyclohexane(N-pentyl) carboxamide The product was prepared via coupling of N'-t-Butyloxycarbonyl-1-aminocyclohexane carboxylic acid and pentylamine as in example 1a. MS(CI) m/e 313(m+H)+, 257, 239, 213, 198. $^1$H NMR(CDCl$_3$,300 MHz) δ 6.70(s,1H), 4.52(bs,1H), 3.23(m,2H), 1.80–2.05(m,4H), 1.65(m,4H), 1.44(s,9H), 1.25–1.38(m,8H), 0.88 (t,J=7 Hz,3H).

Step 80b. N'-(3'-Quinolylcarbonyl)-1-amino-cyclohexane-(N-pentyl) carboxamide The product was obtained in a similar manner to that in examples 1b and 1c using the product of example 80a as the starting material. MS(CI) m/e 368(m+H)+. $^1$H NMR(CDCl$_3$, 300 MHz) δ 9.38(d,J=2 Hz, 1H), 8.58(d,J=2 Hz,1H), 8.18(d,J=8 Hz,1H), 7.94(bd,J=8 Hz,1H), 7.83 (m,1H), 7.65(m,1H), 7.12(bs,1H), 6.27(bs,1H), 3.38(m,2H), 2.34 (m,2H), 2.03(m,2H), 1.65–1.80(m, 4H), 1.50–1.60(m,4H), 1.25–1.40 (m,4H), 0.88(t,J=7 Hz,3H). C,H,N analysis calculated for C$_{22}$H$_{29}$N$_3$O$_2$: C 71.91, H 7.95, N 11.43; found: C 71.73, H 7.95, N 11.33.

EXAMPLE 81

N-(4',8'-Dihydroxy-2'-quinolylcarbonyl)glycine-di-n-pentylamide

The product of example 68a was deprotected in a manner similar to that in example 44 and the resulting amine was then coupled in a manner similar to that in example 5 to yield the title compound. mp=158.5°–159.5° C. MS(FAB) m/e 402(m+H)+, 386, 245, 217. $^1$H NMR(DMSO$_{d6}$,300 MHz) δ 9.90(bs,1H), 9.80(bs,1H), 7.55(bt,J=8 Hz,1H), 7.52(bs,1H), 7.42(m,1H), 7.11(bd,J=8 Hz,1H), 4.20(bd,J=6 Hz,2H), 3.36(bs,H$_2$O), 3.20–3.33(m,4H), 1.58(m,2H), 1.48(m,2H), 1.20–1.33(m,8H), 0.85(m,6H). C,H,N analysis calculated for C$_{22}$H$_{31}$N$_3$O$_4$, H$_2$O: C 62.99, H 7.93, N 10.02; found: C 63.12, H 8.02, N 10.01.

EXAMPLE 82

N-(2'-Naphthoyl)glycine-di-n-pentylamide

The product of example 68a was deprotected in a manner similar to that in example 44 and the resulting amine was then coupled in a manner similar to that in example 11 to yield the title compound. MS(CI) m/e 369(m+H)+, 200, 184, 172. $^1$H NMR (CDCl$_3$,300 MHz) δ 8.38(s,1H), 7.85–7.95(m,4H), 7.50–7.60 (m,3H), 4.30(d,J=4 Hz,2H), 3.40(t,J=7.5 Hz,2H), 3.26(t,J=7.5 Hz,2H), 1.60(m, 4H), 1.25–1.45(m,8H), 0.94(t,J=7 Hz,3H), 0.92(t,J=7 Hz,3H). C,H,N analysis calculated for C$_{23}$H$_{32}$N$_2$O$_2$: C 74.96, H 8.75, N 7.68; found: C 74.44, H 8.75, N 7.55.

EXAMPLE 83

N-(6'-Hydroxy-2'-naphthoyl)glycine-di-n-pentylamide

The product of example 68a was deprotected in a manner similar to that in example 44 and the resulting amine was then coupled with 6-hydroxy-2-naphthoic acid in a manner similar to that in example 11 to yield the title compound. MS(CI) m/e 385(m+H)+, 228, 200, 184. $^1$H NMR(DMSO$_{d6}$,300 MHz) δ 8.58(bt,J=6 Hz,1H), 8.36(bs,1H), 7.86(m,2H), 7.63(d,J=8 Hz,1H), 7.15(m,2H), 4.14(d, J=5 Hz,2H), 3.20–3.35(m,4H), 1.60(m,2H), 1.45(m,2H), 1.20–1.35 (m,8H), 0.89(t,J=7 Hz,3H), 0.86(t,J=7 Hz,3H). C,H,N analysis calculated for C$_{23}$H$_{32}$N$_2$O$_3$: C 71.84, H 8.39, N 7.29; found: C 71.73, H 8.36, N 7.21.

EXAMPLE 84

N-(3'-Methylphenylaminocarbonyl)glycine-di-n-pentylamide

The product of example 68a was deprotected in a manner similar to that in example 44 and the resulting amine was then coupled with 3-methylphenylisocyanate to yield the title compound. mp=66°–7° C. MS(CI) m/e 348(m+H)+, 241, 215, 200, 184. $^1$H NMR (CDCl$_3$,300 MHz) δ 7.08–7.20(m,3H), 7.03(bs,1H), 6.86(bd,J=7 Hz, 1H), 6.21(bs,1H), 4.13(bs,2H), 3.32(bt,J=7.5 Hz,2H), 3.21(bt, J=7.5 Hz,2H), 2.30(s,3H), 1.45–1.65(m,4H), 1.20–1.40(m,8H), 0.92(t, J=7 Hz,3H), 0.86(t,J=7 Hz,3H). C,H,N analysis calculated for C$_{20}$H$_{33}$N$_3$O$_2$: C 69.13, H 9.57, N 12.09; found: C 68.99, H 9.56, N 12.04.

EXAMPLE 85

N-(2'-Chlorophenylaminocarbonyl)-(2R,3S)-(O-benzyl)threonine-di-n-pentylamide The reaction was performed in a similar manner as in the above example utilizing 0.35 g of the hydrochloride salt of example 19b, 2-chlorophenylisocyanate (0.16 g), and TEA (0.135 mL). The product was purified using CHCl$_3$ and MeOH as the elutant mixture. The oily product was isolated in 83% yield (0.42 g). $[\alpha]_D = +21.8°$ (c=0.11, MeOH). MS(CI) m/e 502(m+H)+. $^1$H NMR (CDCl$_3$,300 MHz) δ 0.85(m,6H), 1.23(m,11H), 1.43–1.65(m,4H), 3.0–3.21(m,2H), 3.55(m,2H), 3.33(m,1H), 4.57(d,J=15 Hz,1H), 4.63 (d,J=15 Hz,1H), 4.98(m,1H), 6.48(d,J=9 Hz,1H), 6.95(t,J=7 Hz,1H), 7.2(m,2H), 7.3(m,6H), 8.11(d,J=9 Hz,1H). C,H,N analysis calculated for C$_{28}$H$_{40}$ClN$_3$O$_3$, 0.3 CHCl$_3$: C 63.19, H 7.55, N 7.81; found: C 63.21, H 7.34, N 7.82.

EXAMPLE 86

N-(4',8'-Dihydroxy-2'-quinolylcarbonyl)-(2R,3S)-(O-benzyl)-Threonine-di-n-pentylamide The reaction was performed in a similar manner as in example 5 utilizing 0.35 g of the hydrochloride salt of example 19b 4,8-dihydroxyquinoline-2-carboxylic acid (0.21 g), EDCI (0.22 g), HOBt (0.14 g), and NMM (0.22 g). The oily product was isolated in 60% yield (0.32 g).

[α]$_D$ = +8.0° (c=0.125, MeOH). MS(CI) m/e 536(m+H)+. $^1$H NMR(DMSO$_{d6}$,300 MHz) δ 0.82(m,6H), 1.15-1.3(m, 11H), 1.4-1.6(m,4H), 3.2-3.65(m,4H), 4.08(m,1H), 4.52(d, J=12 Hz,1H), 4.63(d,J=12 Hz,1H), 4.98(t,J=9 Hz,1H), 7.12(m,5H) 7.42 (t,J=9 Hz,1H), 7.55(m,2H), 9.8(d,J=9 Hz,1H), 10.4(bs,1H), 11.72(bs, 2H). C,H,N analysis calculated for C$_{31}$H$_{41}$N$_3$O$_5$, H$_2$O: C 67.25, H 7.83, N 7.59; found: C 67.19, H 7.60, N 7.38.

EXAMPLE 87

Methyl N-(3'-quinolylcarbonyl)-R-methionine-S-(p-hydroxy)-phenylglycinate

Step 87a. Methyl Boc-R-methionine-S-(p-hydroxy)-phenylglycinate

Boc-R-methionine (250 mg, 1 mmol), methyl p-hydroxyphenylglycinate hydrochloride (217 mg, 1 mmol) and TEA (139 μL, 1 mmol) were combined in 10 mL of dichloromethane at 0° C. and treated with BOPCl (254 mg, 1mmol). Additional BOPCl (254 mg) and TEA (134 μL) were added after one day. After two days, the reaction mixture was poured into EtOAc and extracted successively with 0.1% citric acid, 0.1M NaHCO$_3$ and water. The solution was then dried over MgSO$_4$, filtered and evaporated to yield 288 mg, 0.7 mmol (70%). Rf=0.56 (1:1 hexanes - EtOAc). mp=158° C. (dec). MS(CI) m/e 413(m+H)+, 357, 313. $^1$H NMR (CDCl$_3$,300 MHz) d 1.43(s,9H), 3.72(s,3H), 6.73(d,J=8 Hz,2H), 7.17(d,J=8 Hz,2H), 7.33(bs,1H).

Step 87b. Methyl R-methionine-S-(p-hydroxy)-phenylglycinate hydrochloride

The product of the example 87a (250 mg, 0.6 mmol) was treated with 5 mL of 4 N HCl in dioxane at room temperature under a nitrogen atmosphere. After 30 minutes, the excess reagent was evaporated to yield quantitatively the product.

Step 87c. Methyl N-(3'-quinolylcarbonyl)-R-methionine-S-(p-hydroxy)-phenylglycinate The hydrochloride salt of example 87b (50 mg, 0.14 mmol), 3-quinoline carboxylic acid (26 mg, 0.15 mmol) and TEA (21 μL, 0.15 mmol) were dissolved into 5 mL CH$_2$Cl$_2$ and treated with EDCI (29 mg, 0.15 mmol) for 4 hours. The reaction was poured into EtOAc and extracted with 0.1% citric acid and water followed by drying over MgSO4. The resultant filtrate was concentrated and chromatographed over silica gel eluting with a 2:1 to 1:2 hexane - EtOAc gradient to yield 29 mg, 0.06 mmol (44%). MS(CI) m/e 468(m+H)+, 393, 287. $^1$HNMR(CDCl$_3$,300 MHz) δ 2.04(s,3H), 2.12-2.20(m,2H), 2.42-2.52(m,1H), 2.57-2.67(m,1H), 3.65(s,3H), 5.05(q,J=7 Hz,1H), 5.41(d,J=6 Hz,1H), 6.77(d,J=8 Hz,2H), 7.16(d, J=8 Hz,2H), 7.59(dt,J=1,7 Hz,1H), 7.73-7.82(m,3H), 7.83(d,J=8 Hz, 1H), 8.12(d,J=8 Hz,1H), 8.61(d,J=2 Hz,1H), 9.30(d, J=2 Hz,1H). C,H,N analysis calculated for C$_{24}$H$_{25}$N$_3$O$_5$S 0.5 H$_2$O: C 60.49, H 5.60, N 8.81; found: C 60.64, H 5.63, N 8.35.

EXAMPLE 88

N-(3'-Quinolylcarbonyl)-R-serine-di-n-pentylamide

BTFA (trifluoroacetoxyboronate) 0.154 g, 0.4 mmol was added to the product of example 17c (71 mg, 0.145 mol) dissolved in 2 mL of CH$_2$Cl$_2$. Another mL of CH$_2$Cl$_2$ was added and the reaction was monitored by tlc. After 20 minutes of stirring at ambient temperature, the starting material was consumed and the solvents with MeOH were evaporated under vacuum. This evaporation sequence using MeOH was repeated several times. The residue was separated by chromatography using EtoAc-hexane (1:1) as the elutants. An oily product was isolated in 69% yield (40 mg). MS(CI) m/e 400 (m+H)+. $^1$HNMR(CD$_3$OD,300 MHz) δ 0.94 (m,6H), 1.26-1.44 (m,8H), 1.54-1.64(m,2H), 1.68-1.86(m,3H), 3.25-3.35(m,1H), 3.43-3.62(m,3H), 3.82-3.96(m,2H), 5.22(t,J=6 Hz, 1H), 7.73(t,J=6 Hz,1H), 7.91(t,J=6 Hz,1H), 8.07(d,J=9 Hz,1H), 8.12(d, J=9 Hz,1H), 8.9(s,1H), 9.28(s,1H).

EXAMPLE 89

N-(8'-Hydroxy-2-quinolylcarbonyl)-glycine-di-n-pentylalamide

Similar to example 68b, the product of example 68a was deprotected and coupled to 8-hydroxy-2-quinolinic carboxylic acid in a standard fashion utilizing EDCI etc. to provide the product. MS(CI) m/e 386 (m+H)+. $^1$HNMR(CDCl$_3$,300 MHz) δ 8.96(bs,1H), 8.23(s,2H), 8.02(s,1H), 7.53(t,J=7.5 Hz,1H), 7.36(dd, J=1,7.5 Hz,1H), 7.23(dd,J=1,7.5 Hz, 1H), 4.34(d,J=5 Hz,2H), 3.42(bt, J=8 hz,2H), 3.28(bt,J=8 Hz,2H), 1.55-1.70(m,4H), 1.25-1.40(m,8H), 0.93(apparent q,6H). C,H,N analysis calculated for C$_{22}$H$_{31}$N$_3$O$_3$ 0.2 H$_2$O: C 67.91, H 8.13, N 10.80; found: C 67.90, H 8.14, N 10.69.

EXAMPLE 90

N-Methyl-N-(3'quinolylcarbonyl)-glycine-di-n-pentylamide

The product of example 71b was methylated using bistrimethylsilylamide and methyl iodide in THF at −78° C. warming to ambient temperature to provide product after standard workup and purification. MS(DCI) m/e 384(m+H)+.

EXAMPLE 91

N-(3'-Iodo-2'-indolylcarbonyl)-glycine-di-n-pentylamide

The product of example 68b was iodinated with N-iodo-succinimide to provide product after chromatographic purification. MS(DCI) m/e 484(m+H)+. C,H,N analysis calculated for C$_{21}$H$_{30}$IN$_3$O$_2$: C 52.18, H 6.25, N 8.69; found: C 52.04, H 6.21, N 8.49.

EXAMPLE 92

N-(2'-Indolylcarbonyl)-R-alanine-di-n-pentylamide

In a similar fashion to example 1 the product was prepared from the corresponding R-alanyl-di-n-pentylamide hydrochloride and 3-quinoline carboxylic acid to yield product. MS(CI) m/e 372(m+H)+. C,H,N analysis calculated for titled product: C 71.1, H 8.95, N 11.31; found: C 70.76, H 9.03, N 11.17.

EXAMPLE 93

N-(2'-Indolylcarbonyl)-R-methioninesulfoxide-di-n-pentylamide

In a similar manner to examples 54 and 55 the product was prepared using the trifluoroacetate salt of example 54b and indolyl-2-carboxylic acid.

EXAMPLE 94

N-(m-Toluylaminocarbonyl)-(β-O-benzyl)-R-serine-4'-benzoylpiperidide

Step 94a,
N-(t-Butyloxycarbonyl)-(β-O-benzyl)-R-serine-4'-benzoylpiperidide

N-(t-Butyloxycarbonyl)-(β-O-benzyl)-R-serine (2.79 g, 9.45 mmol), 4-benzoylpiperidine hydrochloride (2.13 g, 9.45 mmol), HOBt (1.59 g, 10.40 mmol), and N-methylmorpholine (NMM) (1.56 mL, 14.18 mmol) were dissolved in 20 mL anhydrous $CH_2Cl_2$:DMF (1:1). The mixture was cooled to ice bath temperature and EDCI (1.99 g, 10.40 mmol) was added in portions over 15 min. The reaction was allowed to stir at ice bath temperature for 3 h and then allowed to warm to ambient temperature over an additional 3 h, whereupon ethyl acetate and saturated aqueous $NaHCO_3$ were added. The aqueous portion was extracted three times with ethyl acetate, and the combined organic extractions were washed twice with saturated aqueous $NaHCO_3$, twice with saturated aqueous $KHSO_4$, and once with brine. The solution was then dried over $Na_2SO_4$, filtered, and the volatile components were evaporated. Following silica gel chromatography, EtOAc: hexane (1:1), fractions judged to be pure were pooled, and the volatile components were evaporated to give the title compound as a white solid (4.14 g, 8.88 mmol) in 94% yield. MS(CI) m/e 467 $(M+H)^+$. NMR ($CDCl_3$,300 MHz) δ: 1.43 (s,9H), 1.49–1.97 (m,4H), 2.93 (m,1H), 3.18 (m,1H), 3.45 (m,1H), 3.46–3.68 (m,2H), 4.05 (m,1H), 4.46–4.61 (m,3H), 4.87 (m,1H), 5.51 (m,1H)7.27–7.36 (m,5H), 7.45–7.53 (m,2H), 7.57 (m,1H), 7.88–7.94 (m,2H).

Step 94b.
N-(m-Toluylaminocarbonyl)-(β-O-benzyl)-R-serine-4'-benzoylpiperidide The product of example 94a (235 mg, 0.50 mmol) was treated with 2 mL of 45% trifluoroacetic acid (TFA) in $CH_2Cl_2$ for approximately 2 h whereupon the solution was concentrated in vacuo. $CH_2Cl_2$ was added and evaporated several times to complete TFA removal. The resulting R-serine-4'-benzoylpiperidide trifluoroacetate was dissolved in anhydrous $CH_2Cl_2$ (1 mL) and NMM (0.083 mL, 0.76 mmol) and treated with m-tolyl isocyanate (0.065 mL, 0.50 mmol). After 0.5 h the reaction was subjected to extractive work-up and silica gel chromatography following procedures described in example 94a to give the title compound as a white solid (113 mg, 0.23 mmol) in a 45% yield. MS(CI) m/e 500 $(M+H)^+$. NMR ($CDCl_3$,300 MHz) δ:1.57–1.98 (m,4H), 2.28 (s,3H), 3.01 (m,1H), 3.28 (m,1H), 3.42–3.71 (m,3H), 4.11 (m,1H), 4.47 (s,2H), 4.58 (m,1H), 5.20 (m,1H), 6.49 (br s,1H), 6.82 (m,1H), 7.13 (m,3H), 7.18–7.32 (m,6H, obscured), 7.4 (m,1H), 7.45 (m,2H), 7.57 (m,1H), 7.92 (m,1H). C, H, N analysis calculated for $C_{30}H_{33}N_3O_4$: C 72.12, H 6.66, N 8.41; found: C 72.08, H 6.54, N 8.20.

EXAMPLE 95

N-(m-Toluylaminocarbonyl)-(β-O-benzyl)-R-Aspartyl-4'-benzoylpiperidide

Step 95a,
N-(t-Butyloxycarbonyl)-(β-O-benzyl)-R-Aspartyl-4'-benzoylpiperidide N-(t-Butyloxycarbonyl)-(β-O-benzyl)-R-aspartic acid was converted to the title compound using the procedure of example 94a. MS(CI) m/e 495 $(M+H)^+$, 512 $(M+NH_4)^+$. NMR ($CDCl_3$,300 MHz) $^A$c 1.43 (s,9H), 1.44–1.98 (m,4H), 2.65 (m,1H), 2.77–3.04 (m,2H), 3.23 (m,1H), 3.49 (m,1H), 4.14 (br t,J=18 Hz,1H), 4.47 (br dd,J=15 Hz,30 Hz,1H), 5.02 (m,1H), 5.11 (s,2H), 5.42 (m,1H), 7.31–7.38 (m,5H), 7.45–7.53 (m,2H), 7.57 (m,1H), 7.90–7.997 (m,2H).

Step 95b.
N-(m-Toluylaminocarbonyl)-(β-O-benzyl)-R-Aspartyl-4'-benzoylpiperidide The title compound was prepared from the product of example 95a using the procedure of example 94b. MS(CI) m/e 528 $(M+H)^+$. NMR ($CDCl_3$,300 MHz) $^A$c 1.54–1.79 (m,2H), 1.80–2.03 (m,2H), 2.29 (s,3H), 2.77 (m,1H), 2.83–3.07 (m,2H), 3.19–3.62 (m,2H), 4.23 (br d,J=15 Hz,1H), 4.44 (br t,J=12 Hz,1H), 5.04–5.17 (m,2H), 5.35 (m,1H), 6.24 (m,1H), 6.83 (d,J=7.5 Hz,1H), 7.07–7.34 (m,9H), 7.44–7.53 (m,2H), 7.57 (m,1H), 7.93 (dd,J=7.5,15 Hz,2H). C, H, N analysis calculated for $C_{31}H_{33}N_3O_5$: C 70.57, H 6.30, N 7.96; found: C 70.39, H 6.01, N 7.80.

EXAMPLE 96

N-(m-Toluylaminocarbonyl)-(Y-pyrrolidin-1-yl)-R-Glutamyl-4'-benzoylpiperidide

Step 96a
N-(t-Butyloxycarbonyl)-(Y-O-benzyl)-R-Glutamyl-4'-benzoylpiperidide N-(t-Butyloxycarbonyl)-(Y-O-benzyl)-R-glutamic acid was converted to the title compound using the procedure of example 94a. MS(CI) m/e 509 $(M+H)^+$. NMR ($CDCl_3$,300 MHz) δ: 1.43 (s,9H),1.60–1.87 (m,3H), 1.88–2.13 (m,3H), 2.37–2.64 (m,2H), 2.92 (br dd,J=12,18 Hz,1H), 3.24 (br t,J=13.5 Hz,1H), 3.51 (m,1H), 4.13 (br t,J=15 Hz,1H), 4.51 (br d,J=13.5 Hz,1H)4.24 (m,1H), 5.09–5.19 (m,2H), 5.48 (m,1H), 7.28–7.40 (m,5H), 7.45–7.53 (m,2H), 7.58 (m,1H), 7.94 (d,J=9 Hz, 1H).

Step 96b.
N-(m-Toluylaminocarbonyl)-(Y-O-benzyl)-R-Glutamyl-4'-benzoylpiperidide The title compound was prepared from the product of example 96a by the procedure of example 94b. MS(CI) m/e 542 $(M+H)^+$. NMR ($CDCl_3$,300 MHz) δ: 1.68–2.17 (m,6H), 2.30 (s,3H), 2.48 (m,1H), 2.60 (m,1H), 2.97 (br dd,J=13.5,19.5 Hz, 1H), 3.32 (m,1H), 3.53 (m,1H), 4.19 (br t,J=15 Hz, 1H), 4.49 (m,1H), 5.05 (m,1H), 5.14 (s,2H), 6.21 (d,J=9 Hz,1H), 6.84 (m,1H), 6.97 (d,J=18 Hz,1H), 7.05–7.22 (m,3H), 7.25–7.43 (m,5H), 7.47–7.53 (m,2H), 7.60 (m,1H), 7.89–7.98 (m,2H). C, H, N analysis calculated for $C_{32}H_{35}N_3O_5$: C 70.96, H 6.51, N 7.76; found: C 70.91, H 6.54, N 7.42.

Step 96c.
N-(m-Toluylaminocarbonyl)-(Y-pyrrolidin-1-yl)-R-Glutamyl-4'-benzoylpiperidide The product of example 96b (212 mg, 0.39 mmol) in MeOH (2 mL) was treated with 2N NaOH (0.25 mL, 0.5 mmol), and the mixture was stirred at ambient temperature overnight. The acidic component was isolated by standard extractive proceures to afford 150 mg of the carboxylic acid. A solution of the above acid, pyrrolidine (0.026 mL, 0.34 mmol), and triethylamine in $CH_2Cl_2$ (3 mL) at 0° C. was treated with BOP-Cl. The mixture was allowed to warm slowly to ambient temperature and stir for 2 days. The crude product from acid-base work-up was purified by chromatography (silica gel, 97:3 EtOH/CHCl$_3$) to afford 115 mg (74%) of the product as an oily residue which was lyophilized from EtOH/H$_2$0 to form a fluffy powder. $^1$H-NMR (CDCl$_3$, 300 MHz) δ: 1.7–2.0 (m, 8H), 2.15 (m, 2H), 2.30 (s, 3H), 2.35 (m, 1H), 2.51 (m, 1H), 2.96 (m, 1H), 3.30–3.60 (m, 6H), 4.30 (m, 1H), 4.40–4.60 (m, 2H), 4.98 (m, 1H, exchangeable), 6.29 (m, 1H, exchangeable), 6.80 (t, J=6 Hz, 1H), 7.05–7.21 (m, 3H), 7.49 (m, 2H), 7.58 (m, 1H), 7.92 (m, 2H). MS (CI) m/e 505 (M +H)+. CHN analysis calculated for: C$_{29}$H$_{36}$N$_4$.0.2 H$_2$O: C 68.54, H 7.21, N 11.02; found: C 68.50, H 7.04, N 10.80

EXAMPLE 97

N-(m-Methoxyphenylaminocarbonyl)-(Y-pyrrolidin-1-yl)-R-Glutamyl-4'-benzoylpiperidide Step 97a.
N-(m-Methoxyphenylaminocarbonyl)-(Y-O-benzyl)-R-Glutamyl-4'-benzoylpiperidide The title compound was prepared from the product of example 96a by the procedure of example 94b, substituting m-methoxyphenylisocyanate for m-toluylisocyanate. $^1$H-NMR (CDCl$_3$, 300 MHz) δ: 1.65–2.20 (m, 6H), 2.40–2.60 (m, 2H), 2.98 (m, 1H), 3.32 (m, 1H), 3.52 (m, 1H), 3.77 (s, 3H), 4.20 (m, 1H), 4.50 (m, 1H), 5.02 (m, 1H), 5.12 (s, 2H), 6.58 (m, 1H), 6.80 (m, 1H), 6.95–7.10 (m, 2H), 7.13 (m, 1H), 7.22–7.42 (m, 6H), 7.50 (m, 2H), 7.60 (m, 1H), 7.92 (m, 2H). MS (CI) m/e 558 (M+H+). CHN analysis calculated for: C$_{32}$H$_{35}$N$_3$O$_6$. 1.7 H$_2$O: C 65.34, H 6.58, N 7.14; found: C 65.27, H 5.98, N 6.99.

Step 97b,
N-(m-Methoxyphenylaminocarbonyl)-(γ-pyrrolidin-1yl)-R-Glutamyl-4'-benzoylpiperidide The title compound was prepared from the product of example 97a using the procedure of example 96c. 1H-NMR (CDCl$_3$, 300 MHz) δ: 1.70–2.05 (m, 8H), 2.15 (m, 2H), 2.35 (m, 1H), 2.51 (m, 1H), 2.96 (m, 1H), 3.30–3.60 (m, 6H), 3.79 (s, 3H), 4.30 (m, 1H), 4.44 (m, 1H), 4.52 (m, 1H), 4.97 (m, 1H), 6.25 (m, 1H), 6.55 (m, 1H), 6.81 (m, 1H), 7.12 (m, 2H), 7.49 (m, 2H), 7.59 (m, 1H), 7.91 (d, J=7.5 Hz, 1H). MS (CI) m/e 521 (M+H+). CHN analysis calculated for: C$_{29}$H$_{36}$N$_4$O$_5$.0.5 H$_2$O: C 65.77, H 7.04, N 10.58; found: C 65.88, H 6.71, N 10.58.

EXAMPLE 98

N-(2-Adamantyloxycarbonyl )-(γ-O-benzyl )-R-Glutamyl-4'-benzoylpiperidide

The title compound was prepared from the product of example 96a by the procedure of example 94b substituting 2-adamantyloxychloroformate for m-toluylisocyanate and anhydrous DMF for CH$_2$Cl$_2$. MS(CI) m/e 587 (M+H)+. NMR (CDCl$_3$,300 MHz) δ: 1.46–1.60 (m,3H), 1.65–1.87 (m,10H), 1.88–2.10 (m,7H), 2.38–2.64 (m,2H), 2.92 (m,1H), 3.24 (m,1H), 3.51 (m,1H), 4.12 (br t,J=13.5 Hz, 1H), 4.51 (m, 1H), 4.73–4.85 (m,2H), 5.13 (s,2H), 5.68 (br t,J=7.5 Hz, 1H), 7.26–7.38 (m,5H), 7.45–7.54 (m,2H), 7.59 (m, 1H), 7.90–7.97 (m,2H). C, H, N analysis calculated for C$_{35}$H$_{42}$N$_2$O$_6$: C 71.65, H 7.21, N 4.77; found: C 71.38, H 7.12, N 4.42.

EXAMPLE 99

N-(Phenylaminocarbonyl)-(β-O-benzyl )-R-serine-4'-benzoylpiperidide

The product of example 94a was converted to the title compound by the procedure of example 94b, substituting phenyl isocyanate for m-toluylisocyanate. MS(CI) m/e 486 (M+H)+. NMR (CDCl$_3$,300 MHz) δ: 1.55–1.98 (m,4H), 3.02 (m,1H), 3.29 (m, 1H), 3.47 (m,1H), 3.55–3.69 (m,2H), 4.11 (m,1H), 4.47 (s,2H), 4.52 (m,1H), 5.21 (m,1H), 6.51 (br s,1H), 7.0 (t,J=7.5 Hz,1H), 7.20–7.38 (m,9H), 7.44–7.55 (m,3H), 7.58 (m,1H), 7.91 (m,1H). C, H, N analysis calculated for C$_{29}$H$_{31}$N$_3$O$_4$: C 71.73, H 6.43, N 8.65; found: C 71.85, H 6.46, N 8.51.

EXAMPLE 100

N-(m-Methoxyphenylaminocarbonyl)-(β-O-benzyl)-R-serine-4'-benzoylpiperidide

The product of example 94a was converted to the title compound by the procedure of example 94b, substituting m-methoxyphenyl isocyanate for m-toluylisocyanate. MS(CI) m/e 516 (M+H)+. NMR (CDCl$_3$,300 MHz) δ:1.57–1.99 (m,4H), 3.02 (m, 1H), 3.28 (m, 1H), 3.43–3.68 (m,3H), 3.77 (s,3H), 4.11 (m,1H), 4.48 (s,2H), 4.57 (m, 1H), 5.21 (m, 1H), 6.54 (br d,J=9 Hz,2H), 6.78 (dd,J=3,9 Hz, 1H), 7.07–7.17 (m,2H), 7.21–7.31 (m,5H), 7.41–7.51 (m, 3H), 7.57 (m, 1H), 7.86–7.93 (m,2H). C, H, N analysis calculated for C$_{30}$H$_{33}$N$_3$O$_5$: C 69.88, H 6.45, N 8.15; found: C 69.58, H 6.43, N 8.00.

EXAMPLE 101

N-( m-chlorophenylaminocarbonyl)-(γ-O-benzyl )-R-serine-4'-benzoylpiperidide

The product of example 94a was converted to the title compound by the procedure of example 94b, substituting m-chlorophenyl isocyanate for m-toluylisocyanate. MS(CI) m/e 520, 522 (M+H)+. NMR (CDCl$_3$,300 MHz) δ: 1.63–2.05 (m,4H), 3.10 (m, 1H), 3.33 (m, 1H), 3.50 (m,1H), 3.55–3.67 (m,2H), 4.10 (m, 1H), 4.44 (s,2H), 4.55 (m,1H), 5.19 (m,1H), 6.68 (br s,1H), 6.92 (m, 1H), 7.07–7.20 (m,2H), 7.21–7.29 (m,5H), 7.37 (m, 1H), 7.43–7.51 (m,2H), 7.57 (m,1H), 7.75 (br d,J=25.5 Hz, 1H), 7.90 (t,J=7.5 Hz,2H). C, H, N analysis calculated for C$_{29}$H$_{30}$N$_3$O$_4$Cl: C 66.98, H 5.81, N 8.08; found: C 66.78, H 5.53, N 7.91.

EXAMPLE 102

N-(m-acetylphenylaminocarbonyl)-(β-O-benzyl)-R-serine-4'-benzoylpiperidide

The product of example 94a was converted to the title compound by the procedure of example 94b, substituting m-acetylphenyl isocyanate for m-toluylisocyanate. MS(CI) m/e 520, 522 (M+H)+. NMR (CDCl$_3$,300 MHz) δ: 1.57–2.05 (m,4H), 2.55 (s,3H), 3.11 (m, 1H), 3.31 (m, 1H), 3.53 (m, 1H), 3.57–3.71 (m,2H), 4.13 (m, 1H), 4.45 (s,2H), 4.53 (m, 1H), 5.21 (m, 1H), 7.18–7.37 (m,7H), 7.45–7.68 (m,5H), 7.85 (d,J=10.5 Hz,1H)), 7.90–7.98 (m,3H). C, H, N analysis calculated for C$_{31}$H$_{33}$N$_3$O$_5$: C 70.57, H 6.30, N 7.96; found: C 70.29, H 6.43, N 7.70.

EXAMPLE 103

N-(m-Toluylaminocarbonyl)-(S-benzyl)-S-Cysteine-4'-benzoylpiperidide

Step 103a.
N-(t-Butyloxycarbonyl)-(S-benzyl)-S-Cysteine-4'-benzoylpiperidide To a stirred solution of N-(t-Butyloxycarbonyl)-(S-benzyl)-S-cysteine (200 mg, 0.64 mmol), 4-benzoylpiperidine hydrochloride (145 mg, 0.64 mmol), and triethylamine (0.27 mL, 1.9 mmol) in methylene chloride (5 mL) at 0° C. was added BOP-Cl. The mixture was allowed to warm slowly to ambient temperature and stir for 2 days. Acid-base work-up followed by chromatography (silica gel, 2:1 hexane/EtOAc) afforded the title compound (193 mg, 59%). $^1$H-NMR (CDCl$_3$, 300 MHz) δ: 1.46 (s, 9H), 1.5–2.0 (m, 4H), 2.58 (m, 1H), 2.73 (m, 1H), 2.92 (m, 1H), 3.12 (m, 1H), 3.49 (m, 1H), 3.77 (m, 2H), 3.85 (m, 1H), 4.50 (d, J=13 Hz, 1H), 4.78 (m, 1H), 5.40 (m, 1H), 7.15–7.39 (m 5H), 7.50 (m, 2H), 7.59 (m, 1H), 7.92 (d, J=7.5 Hz, 1H). MS (CI) m/e 483 (M+H$^+$).

Step 103b. N-(m-Toluylaminocarbonyl)-(S-benzyl)-S-Cysteine-4'-benzoylpiperidide The title compound was prepared from the product of example 103a using the procedure of 94b. $^1$H-NMR (CDCl$_3$, 300 MHz) δ: 1.7–2.0 (m, 4H), 2.30 (s, 3H), 2.60–2.87 (m, 2H), 2.98 (m, 1H), 3.20 (m, 1H), 3.50 (m, 1H), 3.75 (dd, J=13.18 Hz, 1H), 3.95 (m, 1H), 4.48 (m, 1H), 5.12 (m, 1H), 6.32 (m, 1H), 6.81 (d, J=7.5 Hz, 1H), 7.06–7.36 (m, 5H}, 7.49 (m, 2H), 7.60 (m, 1H), 7.91 (m, 2H). MS (CI) m/e 516 (M+H$^+$). CHN analysis calculated for: C$_{30}$H$_{33}$N$_3$O$_3$S: C 69.88, H 6.45, N 8.01, S 6.22: found: C 69.73, H 6.70, N 8.01, S 6.25

EXAMPLE 104

N-(m-Toluylaminocarbonyl)-(S-benzyl-S,S-dioxo)-S-Cysteine-4'-benzoylpiperidide The product of example 103b (105 mg, 0.20 mmol) in HOAc (2 mL) was treated with 0.02 mL of 30% aq. H$_2$O$_2$. After stirring for 40 h, the mixture was subjected to standard acid-base work-up, and the crude product was chromatographed (silica gel, 97:3 CHCl$_3$/MeOH) to afford 11 mg of product. After combining with an additional 20 mg obtained similarly, crystallization from Et$_2$/hexane afforded 20 mg of the title compound. $^1$H-NMR (CDCl$_3$, 300 MHz) δ: 1.75 (m, 2H), 1.92 (m, 2H), 2.30 (s, 3H), 3.0 (m, 1H), 3.22–3.46 (m, 3H), 3.51 (m, 1H), 4.06 (m, 1H), 4.40 (s, 2H), 4.42 (m, 1H), 5.50 (m, 1 H), 6.18 (ra, 1H), 6.89 (d, J=7.5 Hz, 1H), 7.05–7.21 (m, 4H), 7.37 (m, 3H), 7.45 (m, 4H), 7.58 (m, 1H), 7.92 (m, 2H). MS (CI) m/e 547 (M+H$^+$). CHN analysis calculated for: C$_{30}$H$_{33}$N$_3$O$_5$S. H$_2$O: C 63.70, H 6.24, N 7.43; found: 63.81, 6.24, 7.43.

EXAMPLE 105

N-(m-Toluylaminocarbonyl)-(S-benzyl-S-oxo)-S-Cysteine-4'-benzoylpiperidide

Continued elution of the column from example 104 afforded 62 mg of the title compound. Trituration with EtOAc afforded 15 mg of the product as colorless crystals. 1H-NMR (DMSO-d6, 300 MHz) δ: 1.20–1.56 (m, 2H), 1.70–1.90 (m, 2H), 2.23 (s, 3H), 2.70–2.96 (m, 3H), 3.22 (m, 1H), 3.70 (m, 1H), 3.90 (m, 1 H), 4.02 (d, J=5 Hz, 0.5H), 4.06 (d, J=5 Hz, 0.5H), 4.20 (d, J=3 Hz, 0.5H), 4.25 (d, J=0.5H), 4.35 (m, 1H), 5.11 (m, 1H), 6.62 (m 1H, exchangeable), 6.72 (d, J=7 Hz, 1H), 7.11 (m, 2H), 7.22 (m, 2H), 7.35 (m, 4H), 7.55 (m, 2H), 7.65 (m, 1H; ;, 8.02 (m, 2H), 8.65 (s, 0.5 H, exchangeable), 8.70 (s, 0.5 H, exchangeable). MS (CI) m/e 532 (M+H$^+$). CHN analysis calculated for: C$_{30}$H$_{33}$N$_3$O$_4$S. 0.8 H$_2$O: C 65.99, H 6.39, N 7.69; found: C 65.79, H 6.00, N 7.58.

EXAMPLE 106

N-(m-Toluylaminocarbonyl)-(β-O-benzyl)-R-serine-4'-(4-fluorobenzoyl)piperidide

Step 106a.
N-(m-Toluylaminocarbonyl)-(β-O-benzyl)-R-serine.

To a suspension of serine(β-O-benzyl)-OH trifluoroacetate salt (2.0 g, 6.47 mmol) in CH$_2$Cl$_2$ (10 mL) and 5 mL of DMF were added NEt$_3$ (1 mL, 7.00 mmol), 4-(N,N-dimethylamino)pyridine (855 mg, 7.00 mmol) and m-toluyl isocyanate (0.9 mL, 7.00 mmol). The mixture was stirred overnight at ambient temperature, then diluted with EtOAc and washed with saturated aqueous KHSO$_4$, H$_2$O, and brine, then dried (Na$_2$SO4) and evaporated to 2.5 g of crude product. Chromatography (silica, 2:1 EtOAc/hexane with 3% HOAc) afforded 1.91 g (68%) of the title compound. MS (CI) m/e 329 (M+H)$^+$. 1HNMR (DMSO-d$_6$, 300 MHz) δ: 2.22 (s, 3H); 3.68 (q, 1H, J=4.5 Hz); 3.85 (q, 1H, J=4.5 Hz); 4.85 (m, 1H); 4.52 (d, 2H, J=3 Hz); 6.52 (d, 1H, J=9 Hz); 6.72 (d, 1H, J=9 Hz); 7.15 (m, 3H); 7.22 (s, 1H); 7.35 (m, 5H); 8.78 (s,1H).

Step 106b.
N-(m-Toluylaminocarbonyl)-(β-O-benzyl)-R-serine-4'-4-fluorobenzoyl)piperidide The product of example 106a was coupled to 4-(p-fluorobenzoyl)piperidine using the EDCI/HOBt procedure in 1:1 DMF/CH2Cl2 analogous to that described in example 94a. MS (CI) m/e 518 (M+H)$^+$. 1HNMR (DMSO-d$_6$, 300 MHz) δ: 1.35–1.45 (nt, 3H); 1.75–1.80 (m, 3H); 2.22 (s, 3H); 2.82 (m, 1H); 3.55 (s, 2H); 3.70 m, 1H); 4.02 (m, 1H); 4.40 (m, 1H); 4.50 (d, 2H, J=6 Hz); 4.92 (m, 1H); 6.60 (d, 1H, J=9 Hz); 6.70 (d, 1H, J=9 Hz); 7.10 (m, 2H, J=9 Hz); 7.20 (s, 1H); 7.30 (m, 6H); 8.06 (q, 2H, J=6 Hz); 8.75 (m, 1H). C, H, N analysis calculated for C$_{30}$H$_{32}$FN$_3$O$_4$.0.5 HOAc: C, 67.99; H, 6.26; N, 7.67. Found: C, 67.90; H, 6.17; N, 7.73.

EXAMPLE 107

N-(m-Toluylaminocarbonyl)-(β-O-benzyl)-R-Serine-piperidine-4'-anilide.

Step 107a.
N-(t-Butyloxycarbonyl)-(β-O-benzyl)-R-serine-4'-methoxycarbonylpiperidide.

Methyl isonipecotate hydrochloride (Carr, et al., J. Org Chem. 55, 1399, 1990) was coupled to N-(t-butyloxycarbonyl)-(β-O-benzyl)-R-serine using the procedure of example 94a. MS(CI) m/e 421 (M+H)$^+$. NMR (CDCl$_3$,300 MHz) δ: 1.37–1.75 (m,11H, includes 1.43 (s,9H)), 1.77–1.97 (m,2H), 2.5 (m, 1H), 2.75–3.16 (m,2H), 3.48–3.64 (m,2H), 3.67 (s,3H), 3.9 (m,1H), 4.35 (m,1H), 4.50 (dd,J=10.5,21 Hz,2H), 4.85 (dd,J=6,12 Hz, 1H), 5.51 (d,J=9 Hz, 1H), 7.25–7.45 (m,5H).

Step 107b.
N-(m-Toluylaminocarbonyl)-(β-O-benzyl)-R-serine-4'-methoxycarbonylpiperidide.

The title compound was prepared from the product of example 107a using the procedure of example 94b. MS(CI) m/e 454 (M+H)+. NMR (CDCl3,300 MHz) δ: 1.44–1.30 (m,2H), 1.31–1.98 (m,2H), 2.29 (s, 3H), 2.52 (m, 1H), 2.38 (m,0.66H), 2.98–3.24 (m, 1.33H), 3.51–3.66 (m,2H), 3.68 (s,3H), 3.96 (m,1H), 4.28 (m,0.SH), 4.40–4.48 (m,2.SH, includes 4.45 (s,2H)), 5.21 (m, 1H), 6.55 (br s,1H), 6.83 (d,J=6 Hz, 1H), 7.12 (m, 1H), 7.16 (m, 1H), 7.17–7.30 (m,6H), 7.44 (d,J=14 Hz, 1H). C, H, N analysis calculated for $C_{25}H_{31}N_3O_5$: C 66.21, H 6.89, N 9.26; found: C 66.06, H 6.59, N 9.04.

Step 107c,(m-Toluylaminocarbonyl)-(β-O-benzyl)-R-serine-piperidine-4'-anilide.

The product of example 107b (5.7 g, 12.6 mmol) was dissolved in 32 mL methanol and 6.3 mL of 2N aqueous NaOH. After 8 h the volatile components were removed in vacuo, ethyl acetate and aqueous saturated KHSO4 were added and the aqueous layer was extracted three times. The combined organic extracts were washed with brine, dried over Na2SO4, filtered and the volatile components evaporated. Fractions judged to be pure after silica gel chromatography, eluting first with ethyl acetate:hexane (1:1) then with ethyl acetate:acetic acid (97:3), were pooled, and the volatile components were evaporated to give (m-toluylaminocarbonyl)-(β-O-benzyl)-R-serine-piperidine-4'-carboxylic acid as a white solid (4.1 g, 9.3 mmol) in 74% yield. The carboxylic acid (2.0 g, 4.5 mmol), aniline (0.4 g, 4.5 mmol), and NMM (0.5 g, 5.0 mmol) were dissolved in CH2Cl2 and cooled to ice bath temperature. EDCI (1.0 g, 5.0 mmol) addition and extractive work-up were carried out as described in example 94a to give the crude title compound (2.3 g, 4.5 mmol) in quantitative yield. A portion (121 mg, 0.24 mmol) was subjected to silica gel chromatography in a manner similar to that described for example 94a, eluting with ethyl acetate: hexane (2:1) to give the title compound as a white powder (83 mg, 0.16 mmol) in 67% yield. MS(CI) m/e 515 (M+H)+. NMR (CDCl3,300 MHz) δ: 1.56–1.83 (m,2H), 1.83–2.99 (m,2H), 2.28 (s,3H), 2.46 (m,1H), 2.84 (m,1H), 3.13 (m,1H), 3.55–3.70 (m,2H), 4.13 (br d,J=13.5 Hz,1H), 4.48 (s,2H), 4.57 (m, 1H), 5.20 (m, 1H), 6.42 (br, 1H), 6.84 (d,J=7.5 Hz, 1H), 7.05–7.23 (m,5H). 7.23–7.43 (m,8H), 7.48 (d,J=7.5 Hz,2H). C, H, N analysis calculated for $C_{30}H_{34}N_4O_4$: C 70.02, H 6.66, N 10.89; found: C 69.82, H 6.78, N 10.73.

EXAMPLE 108

N-(m-Toluylaminocarbonyl)-(γ-pyrrolidin-1-yl)R-Glutamyl-piperidine-4'-anilide.

Step 108a. N-(t-Butyloxycarbonyl)-isonipecotanilide.

Isonipecotic acid (2.0 g, 15 mmol), di-tert-butyl dicarbonate (6.76 g, 30 mmol), and triethylamine (12 ml, 90 mmol) were dissolved in 10 ml of 1,4-dioxane and 10 ml of water. The mixture was stirred for 24 hours at ambient temperature, then diluted with EtOAc and washed with saturated aqueous KHSO4, and brine, dried over Na2SO4, and evaporated to 3.3 g of N-(t-Butyloxycarbonyl)-isonipecotic acid. The N-(t-butyloxycarbonyl)-isonipecotic acid was coupled to aniline by the procedure of example 94a to afford 431 mg of the title product. MS (CI) m/e 305 (M+H)+. 1HNMR (CDCl3, 300 MHz) δ: 1.45 (s, 9H); 1.55 (m, 1H); 1.65–1.72 (m, 2H); 1.82–1.96 (m, 2H); 2.38 (m, 1H); 2.80 (t, 2H); 4.2 (m, 2H); 7.12–7.55 (m, 5H).

Step 108b.
N-(t-Butyloxycarbonyl)-(γ-O-benzyl)-R-Glutamyl-piperidine-4'-anilide.

The product of example 108a (430 me, 1.41 mmol) was treated with 2 ml of 45% trifluoroacetic acid (TFA) in CH2Cl2 for approximately 2 hr, then the solution was concentrated in vacuo, and CH2Cl2 was added and evaporated several times. The resulting piperidine-4'-anilide trifluoroacetate was coupled to N-(t-Butyloxycarbonyl)-(γ-O-benzyl)-R-Glutamic acid using the procedure of example 94a to afford the title compound. MS (CI) m/e 524 (M+H)+. 1HNMR (DMSO-d6, 300 MHz) δ: 0.85 (m, 1H), 1.3 (m, 1H), 1.39 (s, 9H), 1.75–1.90 (br, 4H), 2.45 (m, 2H), 2.65 (m, 2H), 4.05 (m, 2H), 4.45 (m, 2H), 5.10 (s, 2H), 7.05 (m, 1H), 7.25–7.35 (m, 7H), 7.60 (br, d, 2H).

Step 108c.N-(m-Toluylaminocarbonyl)-(γ-O-benzyl)-R-Glutamyl-piperidine-4'-anilide.

The product of example 108b was converted to the title compound using the procedure of example 94b. MS (CI) m/e 557 (M+H)+. 1HNMR (DMSO-d6, 300 MHz) δ: 1.45–1.72 (m, 2H), 1.80–1.98 (m, 4H), 2.24 (s, 3H), 2.45 (br, d, 2H), 2.55–2.75 (m, 3H), 3.1 (m, 1H), 4.12 (br, d, 1H), 4.40 (br, d, 1H), 4.78 (m, 1H), 5.08 (s, 2H), 6.45 (t, 1H), 6.74 (d, 1H), 6.95–7.15 (m, 4H), 7.20 (s, 1H), 7.25–7.7.36 (m, 5H), 7.58 (m, 2H), 8.62 (d, 1H), 9.88 (d, 1H).

Step 108d, . N-(m-Toluylaminocarbonyl)-(γ-pyrrolidin-1-yl-)-R-Glutamyl-piperidine-4'-anilide.

A solution of the product of example 108c (200 mg, 0.359 mmol) in DMF (10 ml) was hydrogenated under one atmosphere of hydrogen at ambient temperature in the presence of 10% Pd/C (200 mg) for 4 hrs. The catalyst was removed by filtration and the filtrate was concerntrated in vacuo. The residue was triturated with ether to yield 180.3 mg of the N-(m-Toluylaminocarbonyl)-R-Glutamyl-piperidine-4'-anilide. The N-(m-Toluylaminocarbonyl)-R-Glutamyl-piperidine-4'-anilide was coupled to pyrrolidine using the EDCI/HOBt procedure in 1:1 CH2Cl2/DMF analogous to that described in example 94a, and afforded 50 mg of the title compound. MS (CI) m/e 520 (M+H)+. 1HNMR (DMSO-d6, 300 MHz) a: 1.65 (s, 16H), 1.75 (t, 1H, J=6 Hz), 1.85 (m, 4H), 2.25 (s, 3H), 4.25 (m, 1H), 4.75 (m, 1H): 6.72 (d, 1H, J=7.5 Hz), 7.05 (q, 2H, J=7.5 Hz), 7.18 (d, 1H, J=9 Hz), 7.38 (m, 3H), 7.62 (d, 2H, J=9 Hz), 9.18 (m, 1H), 10.0 (s, 1H). C, H, N analysis calculated for $C_{29}H_{37}N_5O_4$: C, 67.03; H, 7.77; N, 13.47. Found: C, 67.21; H, 7.06; N, 13.52.

EXAMPLE 109

N-(m-Toluylaminocarbonyl)-(β-O-pyrrolidinecarbamoyl)-R-Serine-piperidine-4'-anilide.

Step 109a.
N-(t-Butyloxycarbonyl)-R-serine-piperidine-4'-anilide.

The title compound is synthesized in a fashion analogous to that described in example 108b, using N-(t-butyloxycarbonyl)-R-serine in place of N-(t-butyloxycarbonyl)-(γ-O-benzyl)-R-glutamate. 1H-NMR (CDCl$_3$, 300 MHz) δ: 1.36 (s, 9H), 1.42–1.89 (m, 5H), 2.59 (m, 1H), 3.07 (m, 1H), 3.41 (m, 1H), 3.52 (m, 1H), 4.06 (m, 1H), 4.41 (m, 2H), 4.60–4.83 (m, 1H), 6.60–6.85 (m, 1H), 7.0 (m, 1H), 7.27 (t, J=7.5 Hz, H), 7.59 (d, J=7.5 Hz, 2H). MS (CI) m/e 392 (M+H)+.

Step 109b.
N-(m-Toluylaminocarbonyl)-R-serine-piperidine-4′-anilide,

The product of example 109a was convened to the title compound using a procedure analogous to that of example 94b. $^1$H-NMR (CDCl$_3$, 300 MHz) δ: 1.70–2.24 (m, 5H, obscured), 2.26 (s, 3H), 2.65 (m, 1H), 2.81 (m, 1H), 3.31 (m, 1H), 4.39 (m, 2H), 4.57 (m, 1H), 4.69 (m, 1H}, 5.37 (m, 1H), 6.76–7.75 (m, 11H). MS (CI) m/e 425 (M+H)+.

Step 109c.
N-(m-Toluylaminocarbonyl)-(β-O-pyrrolidinecarbamoyl)-R-serine-piperidine-4′-anilide.

To a solution of N-(t-Butyloxycarbonyl)-R-serine-piperidine-4′-anilide (105 mg, 0.247 mmol) in 1 ml of CH$_2$Cl$_2$ were added pyrrolidinecarbonyl chloride (99 mg 0.742 mmol), NEt$_3$ (0.043 nil, 0.309 mmol), and DMAP (38 mg, 0.309 mmol) and the mixture was allowed to stand at ambient temperature overnight. After 24 h of reaction, addtional pyrrolidinecarbonyl chloride (99 mg) was added. After 48 h, the mixture was subjected to standard acid-base workurn The crude product was chromatographed (silica gel, EtOAc) and the volatile components were evaporated to give the title compound as a white solid (20 mg) in 16% yield. $^1$H-NMR (CDCl$_3$, 300 MHz) δ: 1.82 (s, 5H), 1.90–2.29 (m, 4H), 2.30 (s, 3H), 2.57 (m, 1H), 2.76 (m, 1H), 3.35 (m, 5H), 4.17–4.36 (m, 3H), 4.57 (m, 1H), 5.21 (m, 1H), 6.13 1H), 6.83–7.61 m, 10H). MS (CI) m/e 522 (M+H)+. CHN analysis calculated for: C$_{28}$H$_{35}$N$_5$OS: C, 63.10, H, 6.91, N, 12.77; found: C, 63.10, H, 6.78, N, 12.69.

EXAMPLE 110

N-(m-Toluylaminocarbonyl)-(β-O-benzylcarbamoyl)-R-serine-piperidine-4′-anilide.

The product of example 107b (2.14 g, 4.16 mmol) in ethanol/acetic acid was stirred under a hydrogen atmosphere in the presence of 10% Pd/C for 2 days. The catalyst was removed by filtration and the solvents were evaporated. A solution of the resulting alcohol (120 mg, 0.28 mmol) in DMF (1 mL) was treated with benzyl isocyanate (0.105 mL, 0.849 mmol) and the mixture was allowed to stir at room temperature for 3 days. Following standard acid-base work-up, the crude product was purified by chromatography (silica gel, 18:5:2 EtOAc:hexane:HOAc) to give the title compound as a white solid (88 mg) in 56% yield, m.p. 109°–112° C. $^1$H-NMR (CDCl$_3$, 300 MHz) δ: 1.62–2.13 (m, 5H), 2.30 (s, 3H), 2.60 (m, 1H), 2.76 (m, 1H), 3.28 (m, 1H), 4.15–4.36 (m, 4H), 4.57 (m, 2H), 5.28 (m, 1H), 6.30 (m, 1H), 6.75–7.60 (m, 15H). MS (CI) m/e 558 (M+H)+. CHN analysis calculated for: C$_{31}$H$_{35}$N$_5$O$_5$. 0.40 AcOH: C, 65.66, H, 6.34, N, 12.04; found: C, 65.53, H, 6.37, N, 11.96.

EXAMPLE 111

N-(m-Toluylaminocarbonyl)-(β-O-(N,N-dimethylaminocarbamoyl)-R-serine-piperidine-4′-anilide.

N-(m-Toluylaminocarbonyl)-R-serine-piperidine-4′-anilide, obtained as described in example 111,(93 mg, 0.219 mmol) in 1 ml of anhydrous CH$_2$Cl$_2$ was treated with NEt$_3$ (0.039 ml, 0.274 mmol), DMAP (34 mg, 0.274 mmol), and N,N-dimethylaminocarbamoyl chloride (0.052 mL, 0.548 mmol) and the mixture was allowed to stand at ambient temperature overnight. After 24 h of reacticn, addtional N,N-dimethylaminocarbonyl chloride (0.052 mL) added. After 48 h, the mixture was subjected to standard acid-base workup. The crude product was chromatographed (silica gel, EtOAc) and the volatile components were evaporated to give the title compound as a white solid (52 mg) in 48% yield, m.p. 113°–1150° C. $^1$H-NMR (CDCl$_3$, 300 MHz) δ: 1.70–2.20 (m, 5H), 2.30 (s, 3H), 2.58 (m, 1H), 2.78 (m, 1H, obscured), 2.90 (s, 6H), 3.23 (m, lit), 4.27 (m, 2H), 4.45 (m, 1H), 4.57 (m, 1H), 5.20 (m, 1H), 6.20 (m, 1H), 6.81–7.60 (m, 10H). MS (CI) m/e 496 (M+H)+. CHN analysis calculated for: C$_{26}$H$_{33}$N$_5$O$_5$. 0.20 H$_2$O: C, 62.56, H, 6.74, N, 14.03; found: C, 62.48, H, 6.72, N, 13.98.

EXAMPLE 112

N-(m-Toluylaminocarbonyl)-(β-O-(N,N-diethylaminocarbamoyl))-R-Serine-piperidine-4′-anilide.

The title compound was prepared in 38% yield as described for example 111 substituting N,N-diethylaminocarbonyl chloride for N,N-dimethylaminocarbonyl chloride. m.p. 107°–110° C. $^1$H-NMR (CDCl$_3$, 300 MHz) 6:1.09 (t, J=7.5 Hz, 6H), 1.62–2.20 (m, 5H), 2.33 (s., 3H), 2.58 (m, 1H), 2.78 (m, 1H), 3.26 (br s, 6H), 4.10–4.34 (m, 3H), 4.54 (m, 1H), 5.21 (m, 1H), 6.05 (m, 1H), 6.82–7.62 (m, 10H). MS (CI) m/e 524 (M+H)+. CHN analysis calculated for: C$_{28}$H$_{37}$N$_5$O$_5$.0.20 EtOAc: C, 63.91, H, 7.19 N, 12.94; found: C, 63.89, H, 7.13, N, 13.03.

EXAMPLE 113

N,(m-Toluylaminocarbonyl)-(β-O-pyrrolidinecarbamoyl)-R-Serine-4′-benzoylpiperidide Step 113a.
N-(t-Butyloxycarbonyl)-R-serine-4′-benzoylpiperidide The title compound was prepared from N-(t-Butyloxycarbonyl)-R-serine and 4-benzoylpiperidine using the procedure of example 94a.$^1$H-NMR (CDCl$_3$, 300 MHz) δ: 1.45 (s, 9H), 1.61–2.02 (m, 4H). 2.80–3.05 (m, 1H), 3.25 (m, 1H), 3.55 (m, 1H), 3.73 (m, 1H), 3.82 (m, 1H), 4.12 m, 1H), 4.40–4.71 (m, 2H), 5.69 m, 1H), 7.46–7.63 (m, 3E), 7.95 (d, J=9 Hz, 2H). MS (CI) m/e 377 (M+H)+.

Step 113b.
N-(m-Toluylaminocarbonyl)-R-serine-4′-benzoylpiperidide

The product of example 113a was converted to the title compound using the procedure of example 94b. $^1$H-NMR (CDCl$_3$, 300 MHz) δ: 1.65–2.01 (m, 4H), 2.30 (s, 3H), 2.99 (m, 1H), 3.32 (m, 1H), 3.55 (m, 1H), 3.83 (m, 2H), 4.15 (m, 1H, obscured), 4.51 (m, 1H), 4.99 (m, 1H), 6.39 (m, 1H), 6.86 (d, J=9 Hz, 1H), 7.14 (m, 4H), 7.43–7.65 (m. 3H), 7.92 (d, J=9 Hz, 2H). MS (CI) m/e 410 (M+H)+.

Step 113c.
N-(m-Toluylaminocarbonyl)-(β-O-pyrrolidinecarbamoyl)-R-serine-4′-benzoylpiperidide The product of example 113b was converted to the title compound using a procedure analogous to that of example 109c. m.p. 101°–103° C., $^1$H-NMR (CDCl$_3$, 300

MHz) δ: 1.64–2.11 (m, 8H), 2.30 (s, 3I-D, 2.99 (m, 1H), 3.34 (m, 5H), 3.53 (m, 1H), 4.18–4.56 (m, 4H), 5.26 (ra, 1H), 6.19 (m, 1H), 6.86 (d, J=9 Hz, 1H), 6.99 (d, J=10.5 Hz, 1H), 7.15 (m, 3H), 7.49 (m, 2H), 7.58 (m, 1H), 7.92 (d, J=9 Hz, 2H). MS (CI) m/e 507 (M+H)+. CHN analysis calculated for: $C_{28}H_{34}N_4O_5$. 0.30 $H_2O$: C, 65.68, H, 6.81, N, 10.94; found: C, 65.65, H, 6.66, N, 10.68.

EXAMPLE 114

N-(m-Toluylaminocarbonyl)-(β-O-morpholinecarbamoyl)-R-Serine-4'-benzoylpiperidide The product of example 113b was converted to the title compound using a procedure analogous to that of example 109c, using morpholinecarbamoyl chloride in place of pyrrolidinecarbamoyl chloride. m.p. 104°–106° C. $^1$H-NMR (CDCl$_3$, 300 MHz) δ: 1.60–2.11 (m, 5H), 2.30 (s, 3H), 3.0 (m, 2H), 3.44 (s, 4H), 3.61 (s, 4H), 4.04–4.56 (m, 4H), 5.28 (m, 1H), 6.16 (m, 1H), 6.88 (m, 2H), 7.15 (m, 3H), 7.49 (m, 2H), 7.58 (m, 1H), 7.92 (m, 2H). MS (CI) m/e 523 (M+H)+. CHN analysis calculated for: $C_{28}H_{34}N_4O_6$.0.20 $H_2O$: C, 63.91, H, 6.59, N, 10.65; found: C, 64.01, H, 6.51, N, 10.55.

EXAMPLE 115

N-(m-Toluylaminocarbonyl)-(β-O-anilinecarbamoyl)-R-serine-4'-benzoylpiperidide

Step 115a.
N-(t-Butyloxycarbonyl)-(β-O-phenylaminocarbamoyl)-R-serine.

N-(t-Butyloxycarbonyl)-R-serine (1.4 g, 6.82 mmol), in 5 ml of anhydrous DMF was treated with phenyl isocyanate (1.48 ml, 13.65 mmol) and the mixture was allowed to stand at ambient temperature overnight. After 24 h of reaction, saturated aqueous NaHCO$_3$ was added. The aqueous portion was extracted three times with ethyl acetate, then the aqueous phase was acidified with solid KHSO$_4$ and further extracted with EtOAc. The combined organic extracts were washed with brine, dried over Na$_2$SO$_4$, then concentrated to give the title compound as a pale yellow solid (2.3g). $^1$H-NMR (CDCl$_3$, 300 MHz) δ: 1.47 (s, 9H), 4.55 (m, 2H), 4.60 (m, 1H), 5.47 (m, 1H), 7.07 (m, 1H), 7.24–7.42 (m, 5H). MS (CI) m/e 342 (M+NH4)+.

Step 115b,
N-(t-Butyloxycarbonyl)-(β-O-phenylaminocarbamoyl)-R-serine-4'-benzoylpiperidide.

The product of example 115a (300 mg, 0.925 mmol), 4-benzoylpiperidine hydrochloride (251 mg, 1.11 mmol), and N-methylmorpholine (NMM) (0.195 ml, 2.78 mmol) were dissolved in 10 ml of anhydrous CH$_2$Cl$_2$:DMF (1:1). The mixture was cooled to ice bath temperature and EDCI (213 mg, 1.11 mmol) was added. The reaction was allowed to stir at ice bath temperature for 2 h and then allowed to warm to ambient temperature overnight. Standard acid-base work-up, followed by trituration of the crude product with CH$_2$Cl$_2$ afforded 201 mg (44%) of a fine white solid. m.p. 215°–216° C. $^1$H-NMR (CDCl$_3$, 300 MHz) δ: 1.44 (s, 9H), 1.54 (s, 2H), 1.97 (m, 3H), 2.94 (m, 1H), 3.35 (m, 1H), 3.59 (m, 1H), 4.07–4.61 (m, 4H), 5.0 (m. 1H), 6.97–8.01 (m, 11H). MS (CI) m/e 496 (M+H)+.

Step 115c.
N-(m-Toluylaminocarbonyl)-(β-O-phenylaminocarbamoyl)-R-serine-4'-benzoylpiperidide.

The product of example 115b was converted to the title compound using the procedure of example 94b. m.p. 108°–110° C. $^1$H-NMR (CDCl$_3$, 300 MHz) δ: 1.70–2.15 (m, 5H), 2.29 (s, 3H), 3.02 (m, 1H), 3.42 (m, 1H), 3.58 (m, 1H), 4.09–4.62 (m, 4H), 5.32 (m, 1H), 6.80–8.0 (m, 16H). MS (CI)m/e 529 (M+H)+. CHN analysis calculated for: $C_{30}H_{32}N_4O_5$.0.30 EtOAc: C, 67.52, H, 6.25, N, 10.09; found: C, 67.44, H, 6.23, N, 10.09.

EXAMPLE 116

(m-Toluylaminocarbonyl)-(β-O-benzyl)-R-Serine-piperidine-4'-m-bromocarboxanilide.

The title compound was prepared from the product of example 107b by a procedure analogous to example 107c, substituting m-bromoaniline for aniline.m.p. 111°–113° C, $^1$H-NMR (CDCl$_3$, 300 MHz) δ: 1.56–2.01 (m, 4H), 2.30 (s, 3H), 2.45 (m, 1H), 2.85 (m, 1H), 3.13 (m, 1H), 3.60 (m, 1H), 3.67 (m, 1H), 4.12 (m, 1H), 4.50 (s, 2H), 4.58 (rn, 1H), 5.18 (m, 1H), 6.15 (d, J=9 Hz, 1H), 6.82–7.80 (m, 15H). MS (CI) m/e 595 (M+H)+. CHN analysis calculated for: $C_{30}H_{33}N_4O_4Br$. 0.10 EtOAc: C, 60.62, H, 5.66, N, 9.30; found: C, 60.41, H, 5.65, N, 934.

EXAMPLE 117

N-(3'-Quinolylcarbonyl)-2-allyl-R,S-phenylalanine-n-pentylamide

Step 117a.
N-(Trifluoroacetyl)-2-allyl-R,S-phenylalanine-n-pentylamide.

A solution of (R,S)-5-allyl-5-benzyl-2-trifluoromethyloxazol-4-one (ca. 3.5 mmol), generated from N-trifluoroacetyl-R-phenylalanine allyl ester according to the literature procedure (Holladay and Nadzan, J. Org. Chem. 56, 3900, 1991), in THF (50 mL) was treated with N-pentylamine (2 mL, 17 mmol), and the mixture was allowed to stand at ambient temperature overnight. After standard acid-base work-up, the crude product was chromatographed over silica gel to afford 1.47 g product, which was crystallized from Et2O/hexane to afford 969 mg (79%) of colorless crystals. $^1$HNMR (CDCl$_3$) δ: 0.9 (t, J=4 Hz, 3H), 1.32 (m, 4H), 1.55 (m, 2H), 2.52 (dd, J=3, 9 Hz, 1H), 3.11 (d, J=9 Hz, 1H), 3.28 (m, 1H), 3.36 (m, 1H), 3.42 (dd, J=4, 9 Hz), 3.67 (d, J=9 Hz, 1H), 5.17 (m, 2H), 5.59 (m, 1H), 5.72 (br t, 1H), 7.09 (m, 2H), 7.29 (m, 3H), 7.84 (s, 1H).

Step 117b,
N-(3'-Quinolylcarbonyl)-2-allyl-R,S-phenylalanine-n-pentylamide.

A solution of the product of Example 117a (280 mg, 0.76 mmol) in 10 mL of MeOH was treated with 10 mL of saturated aqueous Ba(OH)2 and heated at 90° C. for 24h. The solvent was evaporated and the residue was extracted twice with EtOAc. The organic fraction was washed with water and brine, then dried (Na$_2$SO$_4$) and concentrated to 201 mg of free amine. A solution of the amine. quinoline-3-carboxylic acid (152 mg, 0.87 mmol), 4-(N,N-dimethylamino)pyridine (106 mg, 0.87 mmol) and NEt$_3$ (0.2 mL, 1.4 mmol) in CH$_2$Cl$_2$ was treated with 1-cyclohexyl-3-(2-morpholinoethyl)carbodiimide metho-p-toluenesulfonate (CMC, 368 mg, 0.87 mmol). After several days of reaction, additional quinoline-3-carboxylic acid (152 mg) and CMC (368 mg) were added. After several more days, the mixture was subjected to standard acid-base work-up. The crude product was chromatographed (silica gel, 2:1 hexane/EtOAc) then crystallized from $CH_2Cl_2$/hexane to afford 66 mg of the title compound, m.p. 157°–159° C. $^1$H-NMR ($CDCl_3$) δ: 0.92 (t, J=7 Hz, 3H), 1.32 (m, 4H), 1.60 (m, 2H), 2.70 (dd, J=7, 15 Hz, 1H), 3.28 (d, J=15 Hz, 1H), 3.37 (m, 2H), 3.54 (dd, J=7.5, 9 Hz, 1H), 3.83 (d, J=15 Hz, 1H),5.18 (m, 2H), 5.72 (m, 1H), 6.13 (br t, 1H), 7.12 (m, 2H), 7.21 (m, 2H), 7.60 (m, 2H), 7.80 (m, m, 1H), 7.88 (d, J=8 Hz, 1H), 8.15 (d, J=8 Hz, 1H), 8.41 (d, J=2 Hz, 1H), 9.22 (d, J=2 Hz, 1HL MS (CI) m/e 430 (M+H)+. Anal. Calcd for $C_{27}H_{31}N_3O_2.0.25 H_2O$: C, 74.74, H, 7.34, N, 9.69. Found: C, 74.34, H, 7.44, N, 9.71.

EXAMPLE 118

1-n-pentyl-2-oxo-3-benzyl-3-quinoline-3'-carbonylaminopyrrolidine

Step 118a.
1-n-pentyl-2-oxo-3-benzyl-3-trifluoroacetylaminopyrrolidine.

The product of Example 117a (20 mg, 0.54 mmol), and 4-methylmorpholine N-oxide monohydrate ($NMMO.H_2O$) (81 mg, 0.60 retool) were dissolved in acetonitrile (8.6 mL) and $H_2O$ (4.3 mL) at ambient temperature. Osmium tetraoxide ($OsO_4$) (0.072 mL, 0.006 mmol) and sodium periodate ($NaIO_4$) (462 mg, 2.16 mmol) were added sequentially and the mixture was stirred for 48 h whereupon $H_2O$ (10 mL) was added and residual $OsO_4$ and $CH_3CN$ removed in vacuo. Ethyl acetate was added, and extractive work-up was performed as described in example 94a to give a clear oil which was then dissolved in anhydrous $CH_2Cl_2$ (2 mL) under nitrogen atmosphere and treated with triethylsilane (0.173 mL, 1.1 mmol), followed by trifluoroacetic acid (0.21 mL, 2.7 mmol). After 2 h the volatile components were removed in vacuo, ethyl acetate was added, and the organic layer was washed twice with 10% aqueous $Na_2CO_3$ and twice with brine. The solution was dried, filtered, evaporated and the residue subjected to silica gel purification eluting with hexane:ethyl acetate:acetic acid (60:10:2) as in example 94a to give the title compound (145 mg, 0.41 mmol) in 76% yield. MS(CI) m/e 357 (M+H)+, 374 (M+$NH_4$)+. NMR ($CDCl_3$,300 MHz) δ: 0.88 (t,J=7.5 Hz,3H), 1.12–1.42 (m,6H), 2.17–2.36 (m,2H), 2.77 (m, 1H), 2.97–3.26 (m,5H), 7.03 (s,1H), 7.18–7,23 (m,2H), 7.25–7.32 (m,3H).

Step 118b.
1-n-pentyl-2-oxo-3-benzyl-3-quinoline-3'-carbonylaminopyrrolidine

The product example 118a (127 mg, 0.36 mmol) was combined with methanol (5 mL) and aqueous saturated Ba(OH)2 (4 mL)and allowed to stir overnight at ambient temperature whereupon the volatile components were removed in vacuo. $CHCl_3$ and brine were added and the aqueous layer was extracted four times with $CHCl_3$, and the combined organic extracts were dried with $Na_2SO_4$, filtered, and the volatile components were evaporated. The resulting 1-n-pentyl-2-oxo-3-benzyl-3-aminopyrrolidine (94 mg) was then coupled to 3-quinoline-3-carboxylic acid (62 mg, 0.36 mmol) using HOBt (61 mg, 0.40 mmol) and EDCI (77 mg, 0.40 mmol) in a manner similar to that described for example 94a substituting diisopropylethylamine (NEtiPr2) (2 drops) for NMM. The reaction proceeded slowly for 12 days at ambient temperature and additional EDCI (0.12 mmol), HOBt (0.12 mmol), NEtiPr2 (7–9 mmol) and N,N-dimethylaminopyridine (DMAP) (0.07 mmol) were added to the reaction during this time. Extractive work-up was carried out as described in example 94a and the crude product was subjected to radial thin layer chromatography eluting with ethyl acetate:hexane:acetic acid (16:16:1) followed by two successive recrystallizations from ethanol/hexane to give the title compound (90 mg, 0.22 mmol) in 60% yield. MS(CI) m/e 4 15 (M+H)+. NMR ($CDCl_3$,300 MHz) δ: 0.9 (t,J=7.5 Hz,3H), 1.17–1.45 (m,6H), 2.35 (m, 1H), 2.52 (m, 1H), 2.92 (m, 1H), 3.05–3.29 (m,3H), 3.42 (s,0.66H), 3.47 (s,0.33H), 3.5 (br s, 1H), 7.07 (s, 1H), 7.27 (s,5H), 7.63 (m,1H), 7.84 (m,1H), 7.92 (dd,J=1.5,7.5 Hz, 1H), 8.28 (d,J=8.4 Hz, 1H), 8.55 (d,J=1.8 Hz, 1H), 9.32 (d,J=2.5 Hz, 1H). C, H, N analysis calculated for $C_{26}H_{29}N_3O_2$, 1.5 $H_2O$: C 70.56, H 7.29, N 9.49; found: C 70.55, H 6.78, N 9.44.

The ability of the compounds of Formula I to interact with CCK receptors and to antagonize CCK can be demonstrated in vitro using the following protocols.
Pharmacological Methods $CCK_8$ [Asp-Tyr($SO_3$H)-Met-Gly-Trp-Met-Asp-Phe-NH2] was purchased from Peptide International (Louisville, Ky.) or Cambridge Research Biochemicals (Atlantic Beach, N.Y.) EGTA, HEPES and BSA were purchased from Sigma Chemical Co. (St. Louis, Mo.). [$^{125}$I]BH-$CCK_8$ (specific activity, 2200 Ci/mmol) and Aquasol-2 scintillation cocktail were obtained from New England Nuclear (Boston, Mass.). Bestatin and phosphoramidon were purchased from Peptide International. Male guinea pigs, 250 to 325 g, were obtained from Scientific Small Animal Laboratory and Farm (Arlington Heights, Ill.).
Protocol for Radioligand Binding Experiment8

1. Guinea Pig Cerebral Cortical and Pancreatic Membrane Preparations

Cortical and pancreatic membranes were prepared as described (Lin and Miller; *J. Pharmacol. Exp. Ther.* 232, 775–780, 1985). In brief, cortex and pancreas were removed and rinsed with ice-cold saline. Visible fat and connective tissues were removed from the pancreas. Tissues were weighed and homogenized separately in approximately 25 mL of ice-cold 50 mM Tris-HCl buffer, pH 7.4 at 4° C., with a Brinkman Poloytron for 30 sec, setting 7. The homogenates were centrifuged for 10 min at 1075×g and pellets discarded. The supernatants were saved and centrifuged at 38,730×g for 20 min. The resultant pellets were rehomogenized in 25 mL of 50 mM Tris-HCl buffer with Teflon-glass homogenizer, 5 up and down strokes. The homogenates were centrifuged again at 38,730×g for 20 min. Pellets were then resuspended in 20 mM HEPES, containing 1 mM EGTA, 118 mM NaCl, 4.7 mM KCl, 5 mM $MgCl_2$, 100 μM bestatin, 3 μM phosphoramidon, pH 7.4 at 22° C., with a Teflon-glass homogenizer, 15 up and down strokes. Resuspension volume was 15–18 mL per gram of original wet weight for the cortex and 60 mL per gram for the pancreas.

Incubation Conditions
[$^{125}$I]Bolton-Hunter $CCK_8$ ([$^{125}$I]BH-$CCK_8$), and the test compounds were diluted with HEPES-EGTA-salt buffer (see above) containing 0.5% bovine serum albumin (BSA). To 1 mL Skatron polystyrene tubes were added 25 μL of [$^{125}$I]BH-CCK$_8$, and 200 μL of membrane suspension. The final BSA concentration was 0.1%. The cortical tissues were incubated at 30° C. for 150 min and pancreatic; tissues were incubated at 37° C. for 30 min. Incubations were terminated by filtration using Skatron Cell Harvester and SS32 microfiber filter mats. The specific binding of [$^{125}$I]BH-CCK$_8$, defined as the difference between binding in the absence and presence of 1 μM CCK$_8$, was 85–90% of total binding in cortex and 90–95% in pancreas. IC$_{50}$'s were determined from the Hill analysis. The results of these binding assays are shown in Table 1.

Protocol for Amylase Release

This assay was performed using the modified protocol of Lin et al., *J. Pharmacol. Exp. Ther.* 236, 729–734, 1986.

1. Guinea Pig Acini Preparation

Guinea pig acini were prepared by the method of Bruzzone et al. (*Biochem. J.* 226, 621–624, 1985) as follows. The pancreas was dissected and connective tissues and blood vessels were removed. The pancreas was cut into small pieces (2 mm) by a seizure and placed in a 15 mL conical plastic tube containing 2.5 mL of Krebs-Ringer HEPES (KRH) buffer plus 400 units per mL of collagenase. The composition of the KRH buffer was: HEPES, 12.5 mM; NaCl, 118 mM; KCl, 4.8 mM; CaCl$_2$, mM; KH$_2$PO$_4$, 1.2 raM; MgSO$_4$, 1.2 mM; NaHCO$_3$, 5 mM; glucose, 10 mM at pH 7.4. The buffer was supplemented with 1% MEM vitamins, 1% MEM amino acids and 0.001% aprotinin. The tube was shaken by hand until the suspension appeared homogeneous, usually 5–6 min. Five mL of the KRH, without collagenase and with 0.1% BSA, was added and the tube was centrifuged at 50×g for 35 sec. The supernatant was discarded and 6 mL of the KRH was added to the cell pellet. Cells were triturated by a glass pipette and centrifuged at 50×g for 35 sec. This wash procedure was repeated once. The cell pellet from the last centrifugation step was then resuspended in 15 mL of KRH containing 0.1% BSA. The contents were filtered through a dual nylon mesh, size 275 and 75 μM. The tiltrate, containing the acini, was centrifuged at 50×g for 3 min. The acini were then resuspended in 5 mL of KRH-BSA buffer for 30 min at 37° C., under 100% oxygen atmosphere (O$_2$), with a change of fresh buffer at 15 min.

2. Amylase Assay

After the 30 min incubation time, the acini were resuspended in 100 volumes of KRH-BSA buffer, containing 3 μM phosphoramidon and 100 μM bestatin. While stirring, 400 μL of acini were added to 1.5 mL microcentrifuge tubes containing 50 μL of CCK$_8$, buffer, or test compounds. The final assay volume was 500 μL. Tubes were vortexed and placed in a 37° C. water bath, under 100% O$_2$, for 30 min. Afterward, tubes were centrifuged at 10,000 g for 1 min. Amylase activity in the supernatant and the cell pellet were separately determined after appropriate dilutions in 0.1% Triton X-100, 10 mM NaH$_2$PO$_4$, pH 7.4 by Abbott Amylase A-gent test using the Abbott Bichromatic Analyzer 200. The reference concentration for CCK$_8$ in determining the IC$_{50}$'s of the compounds of Formula I was 3×10$^{-10}$M. The results of this assay are shown in Table 2. These results indicate that compounds of the invention are CCK antagonists.

In Vitro Results

The preferred compounds of Formula I are those which inhibited specific [$^{125}$I]-BH-CCK$_8$ binding in a concentration dependent manner. Analysis of [$^{125}$I]-BH-CCK$_8$ receptor binding in the absence and presence of the compounds of formula I indicated the compounds of formula I inhibited specific [$^{125}$I]-BH-CCK$_8$ receptor binding. The IC$_{50}$ values of the compounds of Formula I are presented in Table 1.

TABLE 1

| | [$^{125}$I]-BH-CCK$_8$ Binding | |
|---|---|---|
| Compound of Example | Pancreas IC$_{50}$ (nM) | Cortex IC$_{50}$ (nM) |
| 1 | 40 | 17,000 |
| 2 | 100 | >10,000 |
| 3 | 27 | >10,000 |
| 4 | 290 | >10,000 |
| 5 | 12 | <10,000 |
| 6 | 1000 | >10,000 |
| 7 | 8200 | >10,000 |
| 8 | 4800 | >10,000 |
| 9 | 190 | 1–10,000 |
| 10 | 1100 | >10,000 |
| 11 | 200 | ~100,000 |
| 12 | 1300 | 55,000 |
| 13 | 1600 | >10,000 |
| 14 | 4400 | >10,000 |
| 15 | 87 | ~10,000 |
| 16 | 170 | >10,000 |
| 17 | 140 | 7,200 |
| 18 | 170 | ~10,000 |
| 19 | 73 | ~10,000 |
| 20 | 23 | ≧10,000 |
| 21 | 30 | ~10,000 |
| 22 | 9 | >10,000 |
| 23 | 210 | ~10,000 |
| 24 | 1100 | >10,000 |
| 25 | 48 | 1,400 |
| 26 | 24 | ~10,000 |
| 27 | 320 | ~10,000 |
| 28 | 1000 | >10,000 |
| 29 | 19 | 2,400 |
| 30 | 960 | >10,000 |
| 31 | 950 | >10,000 |
| 32 | 41 | <10,000 |
| 33 | 530 | >10,000 |
| 35 | 140 | 5,200 |
| 36 | 150 | 1–10,000 |
| 37 | 1800 | >10,000 |
| 38 | 260 | ~10,000 |
| 39 | 180 | >10,000 |
| 40 | 70 | ~10,000 |
| 41 | 160 | >10,000 |
| 42 | 92 | >10,000 |
| 43 | 1600 | >10,000 |
| 44 | 37 | ~10,000 |
| 45 | 120 | 5,300 |
| 46a | 250 | >30,000 |
| 46b | 800 | 9,100 |
| 49 | 29 | ≧10,000 |
| 51 | 120 | 3,000 |
| 52 | 145 | ~10,000 |
| 53 | >10,000 | >10,000 |
| 54 | 56 | ~10,000 |
| 55 | 63 | ~10,000 |
| 58 | 3100 | >10,000 |
| 61 | 820 | 4,900 |
| 63 | 1300 | >10,000 |
| 65 | 74 | 28,000 |
| 66 | 42 | 3,300 |
| 67 | 110 | 6,200 |
| 68 | 330 | ~10,000 |
| 69 | 640 | >10,000 |
| 70 | 160 | ~10,000 |
| 71 | 83 | >10,000 |
| 72 | 5500 | >10,000 |
| 73 | 9.3 | 1,600 |
| 74 | 3.1 | 1,700 |
| 75 | 210 | ~10,000 |
| 76 | 870 | ~10,000 |
| 77 | 69 | 6,000 |

TABLE 1-continued

[$^{125}$I]-BH-CCK$_8$ Binding

| Compound of Example | Pancreas IC$_{50}$ (nM) | Cortex IC$_{50}$ (nM) |
|---|---|---|
| 78 | 350 | ~10,000 |
| 79 | 1300 | <100,000 |
| 80 | 2600 | >10,000 |
| 81 | 160 | >10,000 |
| 82 | 130 | nd |
| 83 | 1–10,000 | nd |
| 84 | 100 | nd |
| 86 | 86 | 2,900 |
| 87 | 980 | >10,000 |
| 88 | 51 | nd |
| 89 | 520 | >10,000 |
| 90 | 1090 | >10,000 |
| 91 | 1000 | >10,000 |
| 92 | 230 | <10,000 |
| 93 | 60 | 5,300 |
| 94 | 2130 | 318 |
| 95 | 950 | 270 |
| 96 | 1610 | 53 |
| 97 | 1750 | 61 |
| 98 | 28 | >10,000 |
| 99 | 1900 | 595 |
| 100 | 2400 | 375 |
| 101 | 2400 | 375 |
| 102 | nd | 629 |
| 103 | 1300 | 290 |
| 104 | 951 | 400 |
| 105 | 533 | 77 |
| 106 | 350 | 190 |
| 107 | 430 | 110 |
| 108 | 1270 | 235 |
| 109 | 272 | 22 |
| 110 | 220 | 135 |
| 111 | 318 | 552 |
| 112 | 229 | 445 |
| 113 | 1010 | 40 |
| 114 | nd | 132 |
| 115 | 208 | 115 |
| 116 | 1280 | 728 |
| 117 | 87 | nd |
| 118 | 121 | nd |

The results herein also indicate that compounds of the invention possess selectivity for the pancreatic (type A) CCK receptors.

TABLE 2

Inhibition of CCK-8-induced Amylase Release

| Cmpd of Example | IC$_{50}$ (nM) |
|---|---|
| 1 | 290 |
| 2 | <100,000 |
| 4 | <100,000 |
| 5 | <10,000 |
| 6 | <100,000 |
| 7 | ~100,000 |
| 8 | <100,000 |
| 9 | <100,000 |
| 10 | <100,000 |
| 11 | <30,000 |
| 12 | <100,000 |
| 13 | <100,000 |
| 14 | <100,000 |
| 15 | <100,000 |
| 16 | <100,000 |
| 17 | <100,000 |
| 18 | <100,000 |
| 19 | <100,000 |
| 20 | 140 |
| 21 | <100,000 |
| 22 | <100,000 |
| 24 | <10,000 |
| 25 | 140 |
| 26 | <100,000 |
| 27 | <100,000 |
| 28 | ~100,000 |
| 29 | <100,000 |
| 30 | <100,000 |
| 32 | <100,000 |
| 33 | <100,000 |
| 39 | <100,000 |
| 40 | <100,000 |
| 41 | <100,000 |
| 42 | <100,000 |
| 43 | >10,000* |
| 44 | <10,000 |
| 45 | <10,000 |
| 46a | <100,000 |
| 51 | <10,000 |
| 52 | <100,000 |
| 54 | <10,000 |
| 58 | <10,000 |
| 65 | <1,000 |
| 66 | <1,000 |
| 70 | <100,000 |
| 71 | <100,000 |
| 72 | <100,000 |
| 73 | <100,000 |
| 74 | <100,000 |
| 75 | <100,000 |
| 77 | <100,000 |
| 80 | <10,000 |
| 88 | <1,000 |
| 92 | <100,000 |
| 93 | <10,000 |

*(37.5% inhibition)

Protocol for Calcium Release Assay

This protocol is as described in Lin, et al. Mol. Pharm. 36, 881–886, 1989. NCI-H345 cells were cultured according to Yoder,and Moody, Peptides 8, 103–107, 1987, except that the medium was modified to RPMI 1640 with 2.5% fetal bovine serum (heat inactivated), 5 mcg/L sodium selenite, 5 mg/L human transferrin, 5 mg/L, insulin, 100 units/mL penicillin and 100 µg/L streptomycin. Cells (ca. 200,000/mL) were loaded with 1 mcM indo-1/AM for 1h, washed, and resuspended in Dulbeco's phosphate buffered saline, pH 7.4, plus 0.1% BSA and 0.1% glucose. Intracellular Ca$^{2+}$ levels were monitored with a SLM 8000C spectrofluorimeter with settings of 350 nm excitation and 405 and 480 nm emissions. Calibrations of [Ca$^{2+}$]i were done as described in Grynkiewicz, et al, J. Biol. Chem. 260, 3440–3450, 1985:

$$[Ca^{2+}]_i = K_d (R-R_{min})/(R_{max}-R)$$

where $R_{min}$ and $R_{max}$ were the ratios (480/405) obtained in the presence of excess EGTA (10 mM) and digitonin (50 mcM), respectively. $K_d$ is assumed to be 240 nM, and R is the ratio in the presence and the absence of CCK. Basal calcium levels were 147±3 (n=3) and the maximum levels of calcium stimulated with 1 mcM CCK-8 were 357±3. Test compounds were incubated in varying concentrations with the cells prior to addition of CCK-8 to a final concentration of 10 nM. The IC$_{50}$ value represents the concentration that decreases the response elicited by CCK-8 by 50%.

Table 3 presents the data obtained in the calcium release assay for selected compounds of formula I. These data demonstrate that the activity of these compounds is as antagonistic agents.

TABLE 3

Calcium Release Assay

| Compound of Example No. | IC$_{50}$ (nM) |
|---|---|
| 96 | 251 |
| 109 | 220 |
| 113 | 115 |

In Vivo Results

The ability of the compounds of Formula I to interact with CCK receptors and to antagonize CCK in vivo can be demonstrated using the following protocols.

Inhibition of CCK Induced Gastric Emptying

Three fasted mice were dosed (p.o.) with the test compound. CCK$_8$ (80 μg/kg s.c.) was administered within 60 minutes and charcoal meal (0.1 mL of 10% suspension) was given orally 5 minutes later. The animals were sacrificed within an additional 5 minutes.

Gastric emptying, defined as the presence of charcoal within the intestine beyond the pyloric sphincter, is inhibited by CCK$_8$. Gastric emptying observed in 2 or 3 mice (greater than 1) indicates antagonism of CCK$_8$.

| Compound of example | Dose (p.o.) | Number of mice with Gastric Emptying |
|---|---|---|
| 66 | 100 mg/kg | 2 |

Measurement of Plasma Insulin Level Following Treatment with CCK$_8$ and a Compound of Formula I The ability of the compounds of Formula I to antagonize CCK induced hyperinsulinemia can be demonstrated in vivo using the following protocol.

Male mice, 20–30 g, were used in all experiments. The animals were fed with laboratory lab chow and water ad libitum. The compound of Formula I (1–100 mg/kg in 0.2 mL of 0.9% saline) was administered i.p. Ten minutes later CCK$_8$ (0,2 to 200 nmole/kg in 0,2 mL of 0,9% saline) or saline was injected into the tail vein. Two minutes later the animals were sacrificed and blood was collected into 1,5 mL heparinized polypropylene tubes, The tubes were centrifuged at 10,000×g for 2 minutes. Insulin levels were determined in the supernatant (plasma) by an RIA method using kits from Radioassay Systems Laboratory (Carson, Calif.) or Novo Biolabs (Mass.).

Antagonism of CCK Mediated Behavioral Effect in Mice with Compounds of Formula I Male Swiss CD-1 mice (Charles River) (22–27 g) are provided ample food (Purina Lab Chow) and water until the time of their injection with the test compounds.

ICV injections were given by a free-hand method similar to that previously described (Haley and McCormick, *Br. J. Pharmacol. Chemother.* 12, 12–15 1957). The animals were placed on a slightly elevated metal grid and restrained by the thumb and forefinger at the level of the shoulders, thus immobilizing their heads. Injections were made with a 30 gauge needle with a "stop" consisting of a piece of tygon tubing to limit penetration of the needle to about 4.5 mm below the surface of the skin. The needle was inserted perpendicular to the skull at a midline point equidistant from the eye and an equal distance posterior from the level of the eyes such that the injection site and the two eyes form an equilateral triangle. The injection volume (5 μL) was expelled smoothly over a period of approximately 1 second.

Immediately after the injections the mice were placed in their cages and allowed a 15 minute recovery period prior to the beginning of the behavioral observations.

For the behavioral observations, the mice were placed in clear plastic cages. Each cage measured 19×26×15 centimeters and contained a 60-tube polypropylene test tube rack (NALGENE #5970-0020) placed on end in the center of the cage to enhance exploratory activity. Observations were made every 30 seconds for a period of 30 minutes. Behavior was compared between drug and CCK$_8$ treated mice; CCK$_8$ treated mice; and mice treated with an equal volume of carrier (usually 0.9% saline or 5% dimethylsulfoxide in water). Locomotion as reported here consisted of either floor locomotion or active climbing on the rack. Differences among groups were analyzed by Newman-Kewels analysis and a probability level of $p < 0.05$ was accepted as significant. Each group tested consisted of 10 animals. The results of this test indicate that compounds of Formula I are antagonists of CCK in vivo. Minimally effective doses (MED) are defined as that dose at which a statistically significant reversal of CCK-induced inactivity was observed when the test compound of formula I and CCK$_8$ were coadministered.

| Compound of Example | Dose of CCK$_8$ | MED |
|---|---|---|
| 25 | 3 nmol | 3 nmol |

Protocol for Plus-Maze AsSay,

Male CD1 mice from Charles River weighing 25–30 g were used. They were housed in groups of 14 in Plexiglas cages and located in a temperature-regulated environment with lights on between 7:00 and 20:00 h. All animals used were naive to the apparatus. The elevated plus-maze was made of Plexiglas and consisted of two open arms (17×8.0 cm) and two enclosed arms (17×8×15 cm) extending from a central platform (8×8 cm)(Lister, *Psychophartnacology* 92: 180–185,1987). It was mounted on a Plexiglas base raised 39 cm above the floor. Light levels on the open and enclosed arms were similar. Animals received i.p. injections of the drug 15 min before the beginning of the test. At the beginning of the experiment, mice were placed in the center of the maze and the following variables scored: 1) the time spent in the open arms; 2) the total distance traveled by the mice. These variables were automatically recorded by a camera mounted above the apparatus and analyzed by computer software (Videomex, Columbus Instruments, Columbus, Ohio). The test lasted 5 minutes.

TABLE 4

Anxiolytic-like effect of selected compounds upon elevated plus-maze behavior of mice.

| Drug treatment mg/kg | Time in open arms (sec) |
|---|---|
| Cmpd of Ex. 109 | |
| 0 | 46.8 ± 4.6 |
| 0.001 | 54.1 ± 3.7 |
| 0.01 | 51.9 ± 4.5 |
| 0.1 | 71.5 ± 5.0* |
| 1.0 | 54.6 ± 6.0 |
| Cmpd of Ex 113 | |
| 0 | 31.7 ± 8.1 |
| 0.001 | 53.4 ± 4.9* |
| 0.01 | 38.1 ± 7.1 |
| 0.1 | 46.1 ± 5.5 |

TABLE 4-continued

| Anxiolytic-like effect of selected compounds upon elevated plus-maze behavior of mice. | |
|---|---|
| Drug treatment mg/kg | Time in open arms (sec) |
| 1.0 | 48.7 ± 5.9 |

*statistically significant difference from control

The compounds of Formula I antagonize CCK which makes the compounds useful in the treatment and prevention of disease states in mammals (especially humans) wherein CCK or gastrin may be involved, for example, gastrointestinal disorders such as irritable bowel syndrome, ulcers, excess pancreatic or gastric secretion, hyperinsulinemia, acute pancreatitis, GI cancers (especially cancers of the gall bladder and pancreas), motility disorders, pain (potentiation of opiate analgesia), central nervous system disorders such as anxiety, panic disorder, depression, neuroleptic disorders, tardive dyskinesia, Parkinson's disease, psychosis, including schizophrenia, or Gilles de la Tourette Syndrome; disorders of the appetite regulatory systems, bulimia, Zollinger-Ellison syndrome, and central G cell hyperplasia, and the treatment of substance abuse.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerphosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, pictate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates, long chain halides such as decyl, lauryl, myristyl, and stearyl chlorides, bromides and iodides, arylalkyl halides like benzyl and phenethyl bromides, and others. Water or oil-soluble or dispersible products are thereby obtained.

The pharmaceutically acceptable salts of the present invention can be synthesized from the compounds of Formula I which contain a basic or acidic moiety by conventional methods. Generally, the salts are prepared by reacting the free base or acid with stoichiometric amounts or with an excess of the desired salt forming inorganic or organic acid or base in a suitable solvent or various combinations of solvents.

Examples of acids which may be employed to form pharmaceutically acceptable acid addition salts include such inorganic acids as HCl and phosphoric acid and such organic acids such as oxalic acid, maleic acid, succinic acid and citric acid. Other salts include salts with alkali metals or alkaline earth metals, such as sodium, potassium, calcium, or magnesium or with organic bases.

The pharmaceutically acceptable salts of the acid of Formula I are also readily prepared by conventional procedures such as treating an acid of Formula I with an appropriate amount of base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, TEA, piperidine, pyrrolidine, benzylamine, and the like, or a quaterary ammonium hydroxide such as tetramethylammonium hydroxide and the like.

When a compound of Formula I is used as an antagonist of CCK or gastrin in a human subject, the total daily dose administered in single or divided doses may be in amounts, for exan-tple, from 0.001 to 1000 mga day and more usually 1 to 1000 mg. Dosage unit compositions may contain such amounts of submultiples thereof to make up the daily dose.

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, sex, diet, time of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butandiol. Among the acceptable vehicles and solvents that may be employed are water, Ringer's solution, isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsion, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposotnes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Vol, XIV. Academic Press, New York, N.Y. 1976, p.33 et seq.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

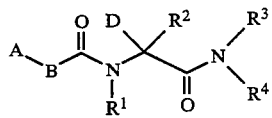

or a pharmaceutically-acceptable salt, ester or amide thereof, wherein:

A is heteroaryl or substituted heteroaryl;

B is absent, or is O, N, S, ethylene, or substituted ethylene;

$R^1$ is hydrogen or $C_1$-$C_3$-alkyl;

$R^2$ is:
  (1) hydrogen,
  (2) aryl-$C_1$-$C_3$-alkyl, or
  (3) when $R^3$ is hydrogen, additionally $C_1$-$C_6$-alkyl, $C_3$-$C_7$-cycloalkyl, or $C_2$-$C_6$-alkenyl; or $R^2$ and D are linked together with the atoms to which they are attached to form:
  (a) —$C_4$-$C_7$-alkylene, or
  (b) —$(CH_2)_q$-G-$(CH_2)_q$-, wherein q is independently 1, 2 or 3 at each occurrence and G is O or S;

D is selected from the group consisting of:
  (1) hydrogen,
  (2) $C_1$-$C_6$-alkyl,
  (3) $C_2$-$C_6$-alkenyl,
  (4) $C_3$-$C_7$-cycloalkyl,
  (5) aryl,
  (6) substituted aryl,
  (7) Het,
  (8) substituted Het,
  (9) aryl-$C_1$-$C_6$-alkyl-,
  (10) Het-$C_1$-$C_6$-alkyl-,
  (11) substituted Het-$C_1$-$C_6$-alkyl-,
  (12) aryl-(mono-substituted-$C_1$-$C_6$-alkyl)-,
  (13) Het-(mono-substituted-$C_1$-$C_6$-alkyl)-,
  (14) $R^6$-O-$C_1$-$C_6$-alkyl-, wherein: $R^6$ is:
    (i) hydrogen,
    (ii) $C_1$-$C_6$-alkyl,
    (iii) aryl-$C_1$-$C_6$-alkyl-,
    (iv) substituted aryl-$C_1$-$C_6$-alkyl-, or
    (v) $R^7$—N—$R^8$—C(O)—, wherein
    $R^7$ is:
      (a) $C_1$-$C_6$-alkyl,
      (b) aryl,
      (c) substituted aryl,
      (d) Het,
      (e) aryl-$C_1$-$C_6$-alkyl-,
      (f) substituted aryl-$C_1$-$C_6$-alkyl-, or
      (g) Het-$C_1$-$C_6$-alkyl-; and $R^8$ is:
      (a) hydrogen,
      (b) $C_1$-$C_6$ alkyl,
      (c) aryl,
      (d) substituted aryl, or
      (e) aryl-$C_1$-$C_6$-alkyl-; or
    $R^7$ and $R^8$ may be linked together with the atoms to which they are attached to form N—$C_4$-$C_7$-alkylene or N—$(CH_2)_q$-G-$(CH_2)_q$-, wherein q and G are as defined above;
  (15) $R^9$—S—$C_1$-$C_6$-alkyl-, wherein: $R^9$ is:
    (i) $C_1$-$C_6$-alkyl,
    (ii) $C_2$-$C_6$-alkenyl,
    (iii) aryl-$C_1$-$C_6$-alkyl-,
    (iv) substituted aryl-$C_1$-$C_6$-alkyl-, or
    (v) $R^7$—N—$R^8$—C(O)—, wherein $R^7$ and $R^8$ are as defined above;
  (16) $R^{10}$—S(O)$_n$-$C_1$-$C_6$-alkyl-, wherein:
    n is 1 or 2, and
    $R^{10}$ is $C_1$-$C_6$-alkyl-, aryl-$C_1$-$C_6$-alkyl-, or substituted aryl-$C_1$-$C_6$-alkyl-; and
  (17) $R^{11}$—NH—$C_1$-$C_6$-alkyl-, wherein: $R^{11}$ is:
    (i) hydrogen,
    (ii) N-protecting group, or
    (iii) $R^7$—J—CO—, wherein $R^7$ is as defined above, and J is:
      (a) absent,
      (b) ethylene,
      (c) substituted ethylene,
      (d) O,
      (e) O—$CH_2$,
      (f) s,
      (f) S—$CH_2$,
      (h) NH, or
      (i) N($C_1$-$C_3$-alkyl); or
  (18) D is linked together with $R^2$ and atoms to which they are attached to form $C_4$-$C_7$-alkylene or —$(CH_2)_q$-G-$(CH_2)_q$-, wherein q and G are as defined above; or
  (19) D is linked together with $R^3$ and atoms to which they are attached to form —CO—N—$C_3$-$C_6$-alkylene or —CO—N—$(CH_2)_q$-G-$(CH_2)_q$-, wherein q and G are as defined above;

$R^3$ is hydrogen or if $R^2$ or D is hydrogen, then additionally:
  (1) $C_1$-$C_6$-alkyl,
  (2) $C_1$-$C_3$-alkyl—O—$C_1$-$C_3$-alkyl,
  (3) $C_2$-$C_6$-alkenyl,
  (4) aryl-$C_1$-$C_6$-alkyl-,
  (5) $C_3$-$C_7$-cycloalkyl, or
  (6) $C_1$-$C_6$-alkylene-$CO_2$-$R^{14}$, wherein $R^{14}$ is $C_1$-$C_6$-alkyl or $C_3$-$C_7$-cycloalkyl; or R³ and D may be linked together to form —CO—N—C₃–C₅-alkylene or —CO—N—(CH₂)q—G—(CH₂)q—, wherein q and G are as defined above:

R⁴ is selected from the group consisting of:
(1) C₁–C₃-alkyl,
(2) C₁–C₃-alkyl-O—C₁–C₃-alkyl,
(3) C₂–C₄-alkenyl,
(4) aryl,
(5) aryl-C₁–C₆-alkyl-,
(6) C₃–C₇-cycloalkyl,
(7) cyano-C₁–C₆-alkyl, or
(8) —C₁–C₃-alkylene-CO₂-R¹⁴, wherein R¹⁴ is C₁–C₆-alkyl, C₃–C₇-cycloalkyl, aryl, or aryl-C₁–C₆-alkylene; or
if R² is hydrogen, then R³ and R⁴ may be additionally linked to form:

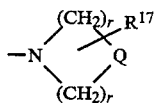

wherein:
r is independently at each occurrence 1 or 2, Q is CH₂ or O, and
R¹⁷ represents one or two substituents independently selected from the group consisting of:
(1) hydrogen,
(2) C₁–C₆-alkyl,
(3) aryl, and
(4) —C(O)—R¹⁸, wherein R¹⁸ is:
  (i) aryl,
  (ii) substituted aryl,
  (iii) heteroaryl,
  (iv) aryl-C₁–C₃-alkyl-,
  (v) substituted aryl-C₁–C₃-alkyl, or
  (vi) N-R¹⁹R²⁰, wherein:
    R¹⁹ is H or C₁–C₃ alkyl, and
    R²⁰ is aryl, aryl-C₁–C₆-alkyl-, or heteroaryl-C₁–C₆ alkyl-.

2. A compound according to claim 1, which is:
N-(3'-Quinolylcarbonyl)-R-valine-di-n-pentylamide;
N-(2'-Indolylcarbonyl)-R-valine-di-n-pentylamide;
N-(4',8'-Dihydroxy-2'-quinolylcarbonyl)-R-valine-di-n-pentylamide;
N-(4'-Hydroxy-2'-quinolylcarbonyl)-R-valine-di-n-pentylamide;
N-(3'-Quinolylcarbonyl )-R-norleucine-di-n-pentylamide;
N-(2'-Indolylcarbonyl )-R-norleucine-di-n-pentylamide;
N-(4',8'-Dihydroxy-2'-quinolylcarbonyl)-R-norleucine-di-n-pentylamide;
N-(3'-Quinolylcarbonyl)-R-(O-benzyl)serine-di-n-pentylamide;
N-(4'-Hydroxy-2'-quinolylcarbonyl)-R-(O-benzyl)serine-di-n-pentylamide;
N-(3'-Quinolylcarbonyl)-(2R,3S )-(O-benzyl)threonine-di-n-pentylamide;
N-(4'-Hydroxy-2'-quinolylcarbonyl )-(2R,3 S )-(O-benzyl)threonine-di-n-pentylamide;
N-(3'-Quinolylcarbonyl)-(2R,3 S )-threonine-di-n-pentylamide;
N-(4'-Hydroxy-2'-quinolylcarbonyl)-(2R,3S )-threonine-di-n-pentylamide;
N-(3'-Quinolylcarbonyl)-(2R,3 S )-(O-methyl)threonine-di-n-pentylamide;
N-(3'-Quinolylcarbonyl)-3-(2'-thienyl)-R-alanine-di-n-pentylamide;
N-(4'-Hydroxy-2'-quinolylcarbonyl)-3-(2'-thienyl)-R-alanine-di-n-pentylamide;
N-(2'-Indolylcarbonyl)-R-histidine-di-n-pentylamide;
N-(3'-Quinolylcarbonyl)-R-histidine-di-n-pentylamide;
N-(4'-Hydroxy-2'-quinolylcarbonyl)-R-histidine-di-n-pentylamide;
N$^a$-(3'-Quinolylcarbonyl)-N$^\xi$-(benzyloxycarbonyl)-R-lysine-di-n-pentylamide;
N-(3'-Quinolylcarbonyl)-R-phenylalanine-di-n-pentylamide;
N-(4'-Hydroxy-2'-quinolylcarbonyl)-R-phenylalanine-di-n-pentylamide;
N$^a$-(3'-Quinolylcarbonyl)-N$^\xi$-(2'-chlorobenzyloxycarbonyl)-R-lysine-di-n-pentylamide;
N-(3'-Quinolylcarbonyl)-R-(4'-hydroxyphenyl)glycine-di-n-pentylamide;
N$^\alpha$(3'-Quinolylcarbonyl)-N$^\xi$-(acetyl)-R-lysine-di-n-pentylamide:
N-(2'-Indolylcarbonyl)-R-tyrosine-di-n-pentylamide;
N-(3'-Quinolylcarbonyl)-R-tyrosine-di-n-pentylamide:
N-(4'-Hydroxy-2'-quinolylcarbonyl)-R-tyrosine-di-n-pentylamide;
Methyl N-(3'-quinolylcarbonyl)-R-tyrosyl-S-phenylglycinate;
Methyl N-(4'-Hydroxy-2'-quinolylcarbonyl)-R-tyrosyl-S-phenylglycinate;
N-(2'-Indolylcarbonyl)-R-homoserine-di-n-pentylamide;
N-(3-Quinolylcarbonyl)-R-homoserine-di-n-pentylamide;
N-(4 -Hydroxy-2'-quinolylcarbonyl)-R-homoserine-di-n-pentylamide;
N-(2-Indolylcarbonyl)-R-methionine-di-n-pentylamide;
N-(2-Indolylcarbonyl)-R-methioninesulfoxide-di-n-pentylamide:
N-(3-Quinolylcarbonyl)-R-methionine-di-n-pentylamide;
N-(4-Hydroxy-2'-quinolylcarbonyl)-R-methionine-di-n-pentylamide;
N-(3'-Quinolylcarbonyl)-R-methioninesulfoxide-di-n-pentylamide;
N$^a$-(3'-Quinolylcarbonyl)-N$^e$-phenylthiolcarbonyl-R-lysine-di-n-pentylamide;
N-(3'-Quinolylcarbonyl)-R-tyrosine-di-n-pentylamide hydrochloride;
N-(3'-Quinolylcarbonyl)-R-histidine-di-n-pentylamide dihydrochloride;
N-(2'-Indolylcarbonyl)-glycine-di-n-pentylamide;
N-(3'-Quinolylcarbonyl)-glycine-di-n-pentylamide;
N-(3'-Quinolylcarbonyl)-R-phenylglycine-di-n-pentylamide;
N-(4',8'-Dihydroxy-2'-quinolylcarbonyl)-R-Phenylglycine-di-n-pentylamide;
N-(5'-Fluoroindolylcarbonyl)-R-phenylglycine-di-n-pentylamide:
N-(5'-Chloroindolylcarbonyl)-R-phenylglycine-di-n-pentylamide:
N-(4',8'-Dihydroxy-2'-quinolylcarbonyl)-glycine-di-n-pentylamide;
N-(4',8'-Dihydroxy-2'-quinolylcarbonyl)-R-(4'-hydroxyphenyl)-glycine-di-n-pentylamide;
N-(4',8'-Dihydroxy-2'-quinolylcarbonyl)-(2R,3S )-(O-benzyl)-threonine-n-pentylamide;

Methyl N-(2'-Indolylcarbonyl)-R-methionine-S-(p-hydroxy)-phenylglycinate;
Methyl N-(3'-Quinolylcarbonyl)-R-methionine-S-(p-hydroxy)-phenylglycinate;
Methyl N-(4',8'-Dihydroxy-2'-quinolylcarbonyl)-R-methionine-S-(p-hydroxy)-phenylglycinate;
N-(3'-Quinolylcarbonyl)-R-serine-di-n-pentylamide;
N-(4',8'-Dihydroxy-2'-quinolylcarbonyl)-R-serine-di-n-pentylamide;
N-(8'-Hydroxy-2-quinolylcarbonyl)-glycine-di-n-pentylamide;
N-Methyl-N-(3'-quinolylcarbonyl)-glycine-di-n-pentylamide;
N-(3'-Iodo-2'-indolylcarbonyl)-glycine-di-n-pentylamide;
N-(3'-Quinolylcarbonyl)-R-alanine-di-n-pentylamide;
N-(2'-Indolylcarbonyl)-R-alanine-di-n-pentylamide;
N-(4',8'-Dihydroxy-2'-quinolylcarbonyl)-R-alanine-di-n-pentylamide; or
N-(3'-Quinolylcarbonyl)-2-allyl-R,S-phenylalanine-n-pentylamide.

3. A compound according to claim 2, which is:
N-(3'-Quinolylcarbonyl)-(2R,3S)-(O-methyl)threonine-di-n-pentylamide;
N-(3'-Quinolylcarbonyl)-(2R,3S)-threonine-di-n-pentylamide;
N-(3'-Quinolylcarbonyl)-R-histidine-di-n-pentylamide dihydrochloride;
N-(3'-Quinolylcarbonyl)-R-phenylglycine-di-n-pentylamide;
N-(4',8'-Dihydroxy-2'quinolylcarbonyl)-R-phenylglycine-di-n-pentylamide;
N-(3'-Quinolylcarbonyl)-R-serine-di-n-pentylamide;
Methyl N-(3'-quinolylcarbonyl)-R-tyrosyl-S-phenylglycinate;
N-(3'-Quinolylcarbonyl)-R-(4'-hydroxyphenyl)glycine-di-n-pentylamide;
N-(2'-Indolylcarbonyl)-R-histidine-di-n-pentylamide;
N-(4',8'-Dihydroxy-2'-quinolylcarbonyl)-R-valine-di-n-pentylamide;
N-(2'-Quinolylcarbonyl)-R-valine-di-n-pentylamide;
N-(3'-Quinolylcarbonyl)-R-valine-di-n-pentylamide or.

4. A pharmaceutical composition for antagonizing CCK comprising a pharmaceutical carrier and a therapeutically-effective amount of a compound of claim 1.

5. A pharmaceutical composition for treatment or prevention of anxiety, panic disorder, neuroleptic disorders, schizophrenia; or disorders of the gastrointestinal, appetite regulating or pain regulating systems comprising a pharmaceutical carrier and a therapeutically-effective amount of a compound of claim 1.

6. A method for treatment or prevention of anxiety, panic disorder, neuroleptic disorder, schizophrenia, or disorders of the gastrointestinal, appetite regulating or pain regulating systems comprising administering to a mammal in need of such treatment a therapeutically-effective amount of a compound of claim 1.

* * * * *